US007805252B2

(12) United States Patent
Gustafsson et al.

(10) Patent No.: US 7,805,252 B2
(45) Date of Patent: Sep. 28, 2010

(54) SYSTEMS AND METHODS FOR DESIGNING AND ORDERING POLYNUCLEOTIDES

(75) Inventors: Claes Gustafsson, Belmont, CA (US); Sridhar Govindarajan, Redwood City, CA (US); Jon E. Ness, Redwood City, CA (US); Alan Marco Villalobos, Mountain View, CA (US); Jeremy Minshull, Los Altos, CA (US)

(73) Assignee: DNA Twopointo, Inc., Menlo Park, CA (US)

( * ) Notice: Subject to any disclaimer, the term of this patent is extended or adjusted under 35 U.S.C. 154(b) by 1007 days.

(21) Appl. No.: 11/207,151

(22) Filed: Aug. 16, 2005

(65) Prior Publication Data

US 2007/0043516 A1 Feb. 22, 2007

(51) Int. Cl.
G06F 7/00 (2006.01)
(52) U.S. Cl. ............................. 702/19; 702/20; 703/11; 707/102
(58) Field of Classification Search ............. 702/19–20; 703/11; 707/102
See application file for complete search history.

(56) References Cited

U.S. PATENT DOCUMENTS

| 5,367,626 | A | 11/1994 | Morioka et al. | |
|---|---|---|---|---|
| 5,631,974 | A | 5/1997 | Lau-Kee et al. | |
| 2005/0064484 | A1* | 3/2005 | Kasai et al. | 435/6 |
| 2005/0227316 | A1 | 10/2005 | Santi et al. | |

OTHER PUBLICATIONS

Medigue, et al., 1999, "Imagene: an integrated computer environment for sequence annotation and analysis," Bioinformatics, 15, pp. 2-15.
Rastogi, Promilia, 2000, "MacVector, Integrated Sequence analysis for the Macintosh," Methods in Molecular Biology, 132, pp. 47-69.
International Search Report and Written Opinion dated Jul. 8, 2008 for PCT/US06/31976.
Altschul et al., 1997, "Gapped BLAST and PSI-BLAST: a new generation of protein database search programs," Nucleic Acids Research 25:3389-3402.
Billoud et al., 1996, "Palingol: a declarative programming language to describe nucleic acids' secondary structures and to scan sequence databases," Nucleic Acids Research 24:1395-1403.
Bisson et al., 1995, "APIC: A Generic Interface for Sequencing Projects," In Proceedings of the Third International Conference on Intelligent Systems for Molecular Biology, AAAI Press, Menlo Park, California, pp. 57-65.
Gribskov et al., 1987, "Profile analysis: Detection of distantly related proteins," Proc. Natl. Acad. Sci. USA 84:4355-4358.
Karp et al., 1998, "EcoCyc: Encyclopedia of *Escherichia coli* genes and metabolism," Nucleic Acids Research 26:50-53.
LeNovère, 2001, "MELTING, computing the melting temperature of nucleic acid duplex," Bioinformatics Applications Note 17:1226-1227.
Lowe et al., 1997, "tRNAscan-SE: a program for improved detection of transfer RNA genes in genomic sequence," Nucleic Acids Research 25:955-964.
Lukashin et al., 1998, "GeneMark.hmmm: new solutions for gene finding," Nucleic Acids Research 26:1107-1115.
Salzberg et al., 1998, "Microbial gene identification using interpolated Markov models," Nucleic Acids Research 26:544-548.
Gordon R.F., (1994), "End-User Object-Oriented Programming by Means of an Object-Oriented Interface," SIGPLAN OOPS Messenger, vol. 5, Issue 1, pp. 6-12.
Jayaraj et al., (2005) "GeMS: all advanced software package for designing synthetic genes," Nucleic Acids Research, 33, pp. 3011-3016.
Villalobos et al., (2006), "Gene Designer: a synthetic biology tool for constructing artificial DNA segments," BMC Bioinformatics 7:285(1-8).
Supplementary European Search Report dated Mar. 30, 2009 for European Application No. 06813483.2-1225 / 1934865.
Jayaraj et al. (2005), "GeMS: an advanced software package for designing synthetic genes," Nucleic Acids Research 33, 3011, Figures 1S through 8S.

* cited by examiner

*Primary Examiner*—Mary K Zeman
(74) *Attorney, Agent, or Firm*—Jones Day; Brett Lovejoy

(57) ABSTRACT

Computer systems, computer program products and methods for designing oligonucleotides are provided. A set of sequence elements is defined. Each sequence element represents an amino acid sequence segment or a nucleic acid sequence segment. The set of sequence elements collectively represent a design nucleic acid sequence. The set of sequence elements are displayed as a plurality icons in a linear or a near linear arrangement such that each respective icon in the plurality of icons uniquely represents a corresponding sequence element in the set of sequence elements. In this representation, neighboring icons in the plurality of icons represent neighboring sequence elements in the set of sequence elements. Each respective icon in the plurality of icons depicts a directional property for the corresponding sequence element in the set of sequence elements. An oligonucleotide selection module is used to identify oligonucleotides in the design nucleic acid sequence.

69 Claims, 32 Drawing Sheets

FIG. 10

Restriction sites — 1002

| Name | Sequence | 5' cut I | 3' cut I | 5' cut II | 3' cut II | Locally Av... | Globally A... |
|---|---|---|---|---|---|---|---|
| AseI | ATTAAT | 2 | 4 | | | ☐ | ☐ |
| AvaI | CYCGRG | 1 | 5 | | | ☐ | ☐ |
| AvaII | GGVVCC | 1 | 4 | | | ☐ | ☐ |
| AvrII | CCTAGG | 1 | 5 | | | ☑ | ☐ |
| BamHI | GGATCC | 1 | 5 | | | ☐ | ☐ |
| BbeI | GAAGAC | 8 | 12 | | | ☐ | ☐ |
| BbvI | GCAGC | 13 | 17 | | | ☐ | ☐ |
| BclI | TGATCA | 1 | 5 | | | ☐ | ☐ |
| BgII | GCCNNN... | 7 | 4 | | | ☐ | ☐ |
| BgIII | AGATCT | 1 | 5 | | | ☐ | ☑ |
| BlpI | GCYNAGC | 2 | 5 | | | ☐ | ☐ |
| BsaI | GGTCTC | 7 | 11 | | | ☐ | ☐ |
| BamAI | GTCTC | 8 | 10 | | | ☐ | ☐ |
| BamBI | CGTCTC | 7 | 11 | | | ☐ | ☐ |
| BstBI | GGTNACC | 1 | 8 | | | ☐ | ☐ |
| BatXI | CCANNNN... | 8 | 4 | | | ☐ | ☐ |
| ClaI | ATCGAT | 2 | 4 | | | ☐ | ☐ |
| DraIII | CACNNNG... | 6 | 3 | | | ☐ | ☐ |
| EagI | CGGCCG | 1 | 5 | | | ☐ | ☐ |
| EarI | CTCTTC | 7 | 10 | | | ☐ | ☐ |
| EcoRI | GAATTC | 1 | 5 | | | ☐ | ☐ |
| EcoRV | GATATC | 3 | 3 | | | ☐ | ☐ |
| FokI | GGATG | 14 | 18 | | | ☐ | ☐ |
| FseI | GGCCGGCC | 6 | 2 | | | ☐ | ☐ |
| HindIII | AAGCTT | 1 | 5 | | | ☐ | ☐ |
| KasI | GGCGCC | 1 | 5 | | | ☐ | ☐ |
| KpnI | GGTACC | 5 | 1 | | | ☐ | ☐ |

Add...
Delete
Show
Motifs...

FIG. 11C

| Name | Sequence | Dam(GATC) | Dcm(CCVVGG) |
|---|---|---|---|
| Acc65I | GGTACC | ☐ | ☑ |
| AlwNI | CAGNNNCTG | ☐ | ☑ |
| ApaI | GGGCCC | ☐ | ☑ |
| AvaII | GGVCC | ☐ | ☑ |
| BanI | GGYRCC | ☑ | ☐ |
| BcgI | CGANNNNNNTGC | ☐ | ☑ |
| BsaI | GGTCTC | ☑ | ☐ |
| BsaBI | GATNNNNATC | ☐ | ☑ |
| BsaHI | GRCGYC | ☐ | ☐ |
| BsII | CCNNNNNNNGG | ☑ | ☑ |
| BsmFI | GGGAC | ☑ | ☑ |
| BspDI | ATCGAT | ☑ | ☐ |
| BspEI | TCCGGA | ☐ | ☐ |
| BspHI | TCATGA | ☐ | ☐ |
| BssKI | CCNGG | ☐ | ☑ |
| BslX1 | CCANNNNNNTGG | ☐ | ☑ |

☑ Avoid methylation of restriction sites (1124)

Known restriction sites blockable by methylation (1126)

[Translate] (1132) [Cancel]

Tabs: General | Amino Acid Sequences | DNA Methyltransferases

Back Translate 1128, 1130

Summary Report

Please select the options to include in the report

- 2202 — ☑ Complete DNA sequence
- 2204 — ☐ DNA sequence of each object
- 2206 — ☐ General and object notes
- 2208 — ☐ Codon translation map
- 2210 — ☐ Restriction site summary
- 2212 — ☐ Codon usage frequencies
- 2214 — ☐ GC content
- 2216 — ☐ List of repeats

[OK] 2218   [Cancel] 2220

FIG. 22

Reports | Configure | Acti
Summary...
Oligos...
Repeats Dot Plot...

FIG. 21

SYSTEMS AND METHODS FOR DESIGNING AND ORDERING POLYNUCLEOTIDES

1. FIELD OF THE INVENTION

The field of this invention relates to computer systems and methods for designing gene constructs and for ordering polynucleotides that encode such gene constructs.

2. BACKGROUND OF THE INVENTION

Molecular genetics has advanced to the stage where polynucleotides can be designed using genetic engineering principles to perform one or more specified functions. However, in order to achieve satisfactory results, multiple design principles must often be considered simultaneously. One example is that for convenient manipulation the presence or absence of specific restriction sites may be required. Another example is that for protein expression, the protein-encoding region of the polynucleotide should favor codons used most abundantly by the desired expression host. Another example is that for expression of a protein fused to a peptide tag, the reading frame between the protein and the tag must be maintained. Another example is that for expression of a protein, it is often desirable to minimize RNA secondary structures within the translation initiation region. Another example is that it is often desirable to alter the order of sequence elements within a polynucleotide construct. Thus, there is a need in the art for systems and methods that can aid in and simplify the process of designing a target nucleic acid sequence

3. SUMMARY OF THE INVENTION

The present invention provides a suite of tools for designing a design nucleic acid sequence (polynucleotide) that encodes a genetic construct of choice and for providing tools to order such designs seamlessly across a network such as the Internet. One aspect of the present invention provides a computer program product for use in conjunction with a computer system, the computer program product comprising a computer readable storage medium and a computer program mechanism embedded therein. The computer program mechanism comprises instructions for representing a set of sequence elements. The set of sequence elements collectively represent a design nucleic acid sequence. The instructions for representing the set of sequence elements comprise instructions for displaying a plurality icons in a linear or a near linear arrangement (e.g., on a computer monitor), each respective icon in the plurality of icons uniquely representing a corresponding sequence element in the set of sequence elements such that neighboring icons in the plurality of icons represent neighboring sequence elements in the plurality of sequence elements. Each of the respective icons in the plurality of icons depicts a directional property for the corresponding sequence element in the set of sequence elements. In some embodiments, the directional property for a corresponding sequence element in the set of sequence elements is a translation direction or a transcription direction.

In some embodiments, the instructions for displaying a set of icons further comprise instructions for displaying an icon in the plurality of icons in an icon view or a sequence view. When the icon is displayed in the icon view, a graphical depiction of the sequence element represented by the icon is displayed. When the icon is displayed in the sequence view, a sequence represented by the icon is displayed. In some embodiments, when the icon is displayed in the sequence view, a name of the sequence element represented by the icon is displayed above the sequence. In some embodiments, when the icon is displayed in the sequence view, a start position and an end position of the sequence element that the icon represents in the nucleic acid sequence, the amino acid sequence, or the mixed sequence is displayed. In some embodiments, the sequence represented by the icon is an amino acid sequence and, for each respective amino acid in the amino acid sequence, each codon corresponding to the respective amino acid is displayed below the respective amino acid. In some embodiments, the sequence represented by said icon is an amino acid sequence or a nucleic acid sequence.

In some embodiments, the computer program mechanism further comprises instructions for depicting a library of sequence elements and instructions for permitting a user to drag a copy of a sequence element in the library of sequence elements onto a panel, thereby incorporating the sequence element into the set of sequence elements. In some embodiments, the library of sequence elements is organized in a hierarchical tree that is graphically displayed. In some embodiments, the library of sequence elements are organized in a hierarchical tree that is graphically displayed and this hierarchical tree is divided into a first portion representing regulatory elements, a second portion representing expressed elements, and a third portion representing cloning elements. In some embodiments, the portion of the hierarchical tree representing regulatory elements is further divided into a subportion representing sequence elements that are transcriptional elements and a subportion representing sequence elements that are translational elements. In some embodiments, the portion of the hierarchical tree representing transcriptional elements is further divided into one or more of the following subportions (i) a subportion representing sequence elements that are enhancers, (ii) a subportion representing sequence elements that are promoters, (iii) a subportion representing sequence elements that are operators, (iv) a subportion representing sequence elements that are terminators, (v) a subportion representing sequence elements that are polyadenylation signals. In some embodiments, the portion of the hierarchical tree representing translational elements is further divided into one or more of the following subportions (i) a subportion representing sequence elements that are 5' and 3' un-translated regions, (ii) a subportion representing sequence elements that are ribosome binding sites, (iii) a subportion representing sequence elements that are initiation AUG contexts, (iv) and a subportion representing sequence elements that are termination codons. In some embodiments, the portion of said hierarchical tree representing expressed elements is further divided into one or more of the following subportions (i) a subportion representing sequence elements that are peptide fusion tags, (ii) a subportion representing sequence elements that are protease cleavage sites, (iii) a subportion representing sequence elements that are solubility or fusion tags, (iv) and a subportion representing sequence elements that are secretion signals. In some embodiments, the portion of the hierarchical tree representing expressed elements is further divided according to organism of origin. In some embodiments, the portion of the hierarchical tree representing cloning elements is further divided into one or more of the following subportions (i) a subportion representing sequence elements that are recombinase recognition sequences, and (ii) a subportion representing sequence elements that are restriction enzyme recognition sequences.

In still another aspect of the present invention, the computer program mechanism further comprises instructions for depicting an empty sequence element and instructions for permitting a user to drag a copy of the empty sequence element onto a panel. When this is done, the empty sequence element is incorporated into the set of sequence elements and the user is prompted to populate the empty sequence element with amino acid sequence, a nucleic acid sequence, or an open reading frame.

In some embodiments, each sequence element in the set of sequence elements is an amino acid element, a DNA element, or an open reading frame element. In some embodiments, the computer program product further comprises instructions for back-translating a sequence element in the set of sequence elements that is an amino acid element or an open reading frame element into the design nucleic acid sequence. In some embodiments, the sequence element is an amino acid sequence and the instructions for back-translating produce the back-translation as a function of (i) the amino acid sequence and (ii) common codon use in a designated species. In some embodiments, the instructions for back-translating further comprise instructions for avoiding the generation of one or more restriction enzyme recognition sequences in the design nucleic acid sequence. Further, the computer program mechanism also comprises instructions for receiving an identity of the one or more restriction enzyme recognition sequences to be avoided from a user.

In some embodiments, the computer program product comprises instructions for back-translating that consider one or more criteria for back-translation. Such one or more criteria are selected from the group consisting of (i) minimization of a repeat element in the design nucleic acid sequence, (ii) avoidance of a predetermined nucleic acid sequence in the design nucleic acid sequence, (iii) minimization of a secondary structure in the design nucleic acid sequence, (iv) minimization of sequence identity with respect to a reference sequence or maximization of sequence identity with respect to the reference sequence, (v) avoidance of an enzyme recognition sequence in the design nucleic acid sequence, (vi) selection of a codon based on codon frequency specified by a codon table; (vii) elimination of a methylation site that would inhibit the action of an enzyme in the design nucleic acid sequence; and (viii) avoidance of a first subsequence in the design nucleic acid sequence that has an annealing temperature with a second subsequence in the design nucleic acid sequence that is above a predetermined value. In some embodiments, the computer program product further comprises instructions for fixing and unfixing the corresponding nucleic acid sequence. In such embodiments, when the corresponding nucleic acid is fixed, it cannot be subjected to back-translation optimization. Further, when the corresponding nucleic acid is unfixed, it can be further subjected to back-translation optimization. In some embodiments, the computer program mechanism further comprises instructions for independently toggling each open reading frame element in the set of sequence elements between a fixed state and an unfixed state and instructions for back-translating a sequence element in the set of sequence elements that is an open reading frame element in an unfixed state into a corresponding nucleic acid sequence.

In some embodiments, the computer program mechanism further comprises instructions for permitting a user to rearrange an order of the sequence elements in the linear or near linear arrangement thereby causing a corresponding change in the design nucleic acid sequence. In some embodiments, the computer program mechanism further comprises instructions for permitting a user to change an attribute of an icon in the plurality of icons. Examples of such attributes include, but are not limited to a name of the icon, a color of the icon, a size of the icon, or a resolution of the icon.

In some embodiments, a sequence element in the set of sequence elements is a DNA element and the instructions for displaying a set of icons further comprise instructions for displaying an icon in the plurality of icons representing the DNA element in an icon view or a sequence view. Further, when the icon is displayed in the icon view, a graphical depiction of the sequence element represented by the icon is displayed and when the icon is displayed in the sequence view, a sequence represented by the icon is displayed. Additionally, in sequence view, all six reading frames of the sequence represented by the icon are displayed. Here, the sequence is determined by a (i) nucleic acid sequence for the sequence and (ii) a reading frame of a second icon that precedes or follows said first icon in the linear or near linear arrangement, wherein said second icon represents an amino acid element.

In some embodiments, a sequence element in the set of sequence elements is an amino acid element and the computer program product further comprises instructions for back-translating the amino acid element to a corresponding nucleic acid sequence. The instructions for displaying a set of icons further comprise instructions for displaying an icon in the plurality of icons representing the amino acid element in an icon view or a sequence view. Further, when the icon is displayed in the icon view, a graphical depiction of the sequence element represented by the icon is displayed. When the icon is displayed in the sequence view, an amino acid sequence represented by the icon is displayed. For each respective amino acid in the amino acid sequence, each possible codon for the respective amino acid is displayed below the respective amino acid. In some embodiments, codons for each respective amino acid in the amino acid sequence are ranked in the sequence view in accordance with a codon bias table. Some embodiments of the present invention provide instructions for obtaining the codon bias table from among a plurality of codon bias tables. Such a codon bias table indicates a frequency for each possible codon encoding a naturally occurring amino acid. In some embodiments, the frequency for each possible codon encoding a naturally occurring amino acid is the frequency of occurrence of each possible codon encoding a naturally occurring amino acid in a species corresponding to the codon bias table.

Another aspect of the invention provides instructions for setting a back-translation threshold. The instructions for back-translating include instructions for excluding codons in the corresponding nucleic acid sequence that are below the back-translation threshold in a codon bias table. Still another aspect of the invention provides instructions for displaying codons that fall below the back-translation threshold in a first color and instructions for displaying codons that are above the back-translation threshold in a second color.

Some embodiments of the present invention provide instructions for displaying a restriction site analysis box comprising a plurality of restrictions site names and, for each restriction site name in the plurality of restriction site names, the corresponding restriction sequence. Still further, such embodiments provide instructions for indicating positions of one or more restriction sites in the plurality of restriction sites in the set of sequence elements that are displayed as a plurality of icons in the linear or said near linear arrangement. In some embodiments of the present invention, a sequence element in the set of sequence elements comprises an amino acid sequence or an open reading frame. Such instructions for indicating positions of one or more restriction sites comprises instructions for indicating a position where a restriction site could occur in the amino acid sequence or the open reading frame without changing the amino acid sequence or the open reading frame. Some embodiments provide instructions for adding or removing a restriction site name to the plurality of restriction site names as well as instructions for selecting and deselecting a restriction site name in the plurality of restriction site names. When the restriction site name is selected the position of each restriction site in the set of sequence elements corresponding to the restriction site name is displayed.

In some embodiments, a sequence element in the set of sequence elements is an open reading frame element and the computer program product further comprises instructions for setting a codon usage threshold. The instructions for displaying a set of icons further comprise instructions for displaying an icon in the plurality of icons representing the open reading frame element in an icon view or a sequence view. When the icon is displayed in the icon view, a graphical depiction of the sequence element represented by the icon is displayed. When the icon is displayed in the sequence view, an amino acid sequence represented by the icon is displayed. For each respective amino acid in this amino acid sequence, each possible codon for the respective amino acid is displayed. Further, the actual codons used by the open reading frame element are indicated in a first color when such codon appear with a frequency in a codon bias table that is above the codon usage threshold. The actual codon used by the open reading frame element is indicated in a second color when such codon appears with a frequency in the codon bias table that is below the codon usage threshold.

In some embodiments, the instructions for displaying a set of icons comprise instructions for displaying an icon in the plurality of icons in an icon view or a sequence view. When the icon is displayed in the icon view, a graphical depiction of the sequence element represented by the icon is displayed. When the icon is displayed in the sequence view, a first sequence represented by the icon is displayed. The first sequence is a nucleic acid sequence or an amino acid sequence represented by the icon. Further, when the icon is displayed in the sequence view, the design nucleic acid sequence is displayed above the first sequence. The design nucleic acid sequence corresponds to all or a portion of the amino acid sequence segments and/or the nucleic acid sequence segments of the set of sequence elements. In some embodiments, the first sequence is an amino acid sequence and the computer program mechanism further comprises instructions for back-translating all or a portion of the first sequence into the design nucleic acid sequence. In some embodiments, the first sequence is an amino acid sequence and the computer program mechanism further comprises instructions for positioning a graphic icon at a position in the first sequence where a restriction site can be introduced without changing the first sequence and instructions for placing the restriction site recognition sequence in the design nucleic acid sequence when a user selects the graphic icon to indicate that the restriction site is desired. In some embodiments, the computer program mechanism further comprises instructions for graphically displaying overhangs generated by cleavage of the restriction site recognition sequence and instructions for displaying the name of the restriction enzyme that recognizes the restriction site recognition sequence in the vicinity of the restriction site recognition sequence in the design nucleic acid sequence. In some embodiments, the instructions for displaying further comprise, for each respective amino acid in the first sequence, instructions for displaying each codon corresponding to the respective amino acid sequence below the first sequence. Furthermore, the instructions for placing further comprise instructions for highlighting each codon below the first sequence that is in the restriction site recognition sequence when a user selects the graphic icon to indicate that the restriction site is desired.

In some embodiments, the computer program mechanism further comprises a $T_m$ calculation module. The $T_m$ calculation module has instructions for selecting a start point and an end point in the design nucleic acid sequence, instructions for computing a $T_m$ of the nucleic acid defined by the start point and said end point in the design nucleic acid sequence, and instructions for displaying the $T_m$ of the oligonucleotide defined by the start and end point. In some embodiments, the instructions for displaying the $T_m$ of the nucleic acid comprise instructions for displaying the $T_m$ and a numeric representation of the start point and the end point. In some embodiments, the $T_m$ calculation module further comprises instructions for moving the start point and/or the end point and, for each new specified start point and/or end point, repeating the instructions for computing and the instructions for displaying.

In some embodiments, the computer program mechanism further comprises an oligonucleotide marker module. The oligonucleotide marker module comprises instructions for selecting a start point and an end point in the design nucleic acid sequence, instructions for defining a transcriptional direction of the oligonucleotide defined by the start point the end point, and instructions for displaying the oligonucleotide as a graphic above or below the design nucleic acid sequence.

In some embodiments, the computer program mechanism further comprises instructions for merging a first sequence element and a second sequence element in the set of sequence elements thereby forming a single sequence element in the set of sequence elements from the first sequence element and the second sequence element. In some embodiments, the computer program mechanism further comprises instructions for selecting a portion of a first sequence element in the set of sequence elements and splitting the portion of the first sequence element into a new second sequence element in the set of sequence elements. In some embodiments, the computer program mechanism further comprises instructions for selecting a contiguous sequence that is all or a portion of two or more adjacent sequence elements in the linear or near linear arrangement. In such embodiments, the computer program product comprises instructions for splitting the contiguous sequence into a new sequence element in the set of sequence elements and eliminating the contiguous sequence in the two or more adjacent sequence elements.

In some embodiments, the computer program mechanism further comprises instructions for saving the set of sequence elements as a project and instructions for permitting the selection of a project from among a plurality of projects. Each project in the plurality of projects comprises a set of sequence elements. In such embodiments, the computer program product further comprises instructions for linking a first sequence element in the set of sequence elements in one project with a corresponding second sequence element in a set of sequence elements in another project in the plurality of projects such that, when changes are made to a nucleic acid sequence associated with the first sequence element, the same changes are made to a nucleic acid sequence associated with the second sequence element. The invention accordingly provides instructions for removing such links. In some embodiments, there are instructions for locking the nucleic acid sequence associated with the first sequence element and the nucleic acid sequence associated with the second sequence element so that no change is allowed to either nucleic acid sequence.

In some embodiments, the computer program product further comprises instructions for generating a report. Such a report comprises any combination of (i) the sequence of the design nucleic acid sequence, (ii) a nucleic acid sequence associated with each sequence element in the set of sequence elements, (iii) a codon translation map for the design nucleic acid sequence, (iv) a restriction site summary for the design nucleic acid sequence, (v) a codon usage frequency analysis for the design nucleic acid sequence, (vi) a GC content for the design nucleic acid sequence, (vii) a list of repeats in the design nucleic acid sequence and/or (viii) a list of each oligonucleotide associated with design nucleic acid sequence.

Another aspect of the invention provides a computer system comprising a central processing unit and a memory, coupled to the central processing unit. The memory stores instructions for representing a set of sequence elements that collectively represent a design nucleic acid sequence. The instructions for representing the set of sequence elements comprise instructions for displaying a plurality of icons in a linear or a near linear arrangement. Each respective icon in said plurality of icons uniquely represents a corresponding sequence element in the set of sequence elements such that neighboring icons in the plurality of icons represent neighboring sequence elements in the plurality of sequence elements. Each said respective icon in the plurality of icons depicts a directional property for the corresponding sequence element in said set of sequence elements.

4. BRIEF DESCRIPTION OF THE DRAWINGS

FIG. 10 illustrates a restriction site panel that is used to select restriction sites in accordance with an embodiment of the present invention.

FIG. 11C illustrates a part of the interface for a back-translation module in accordance with an embodiment of the present invention.

Figure 16A:
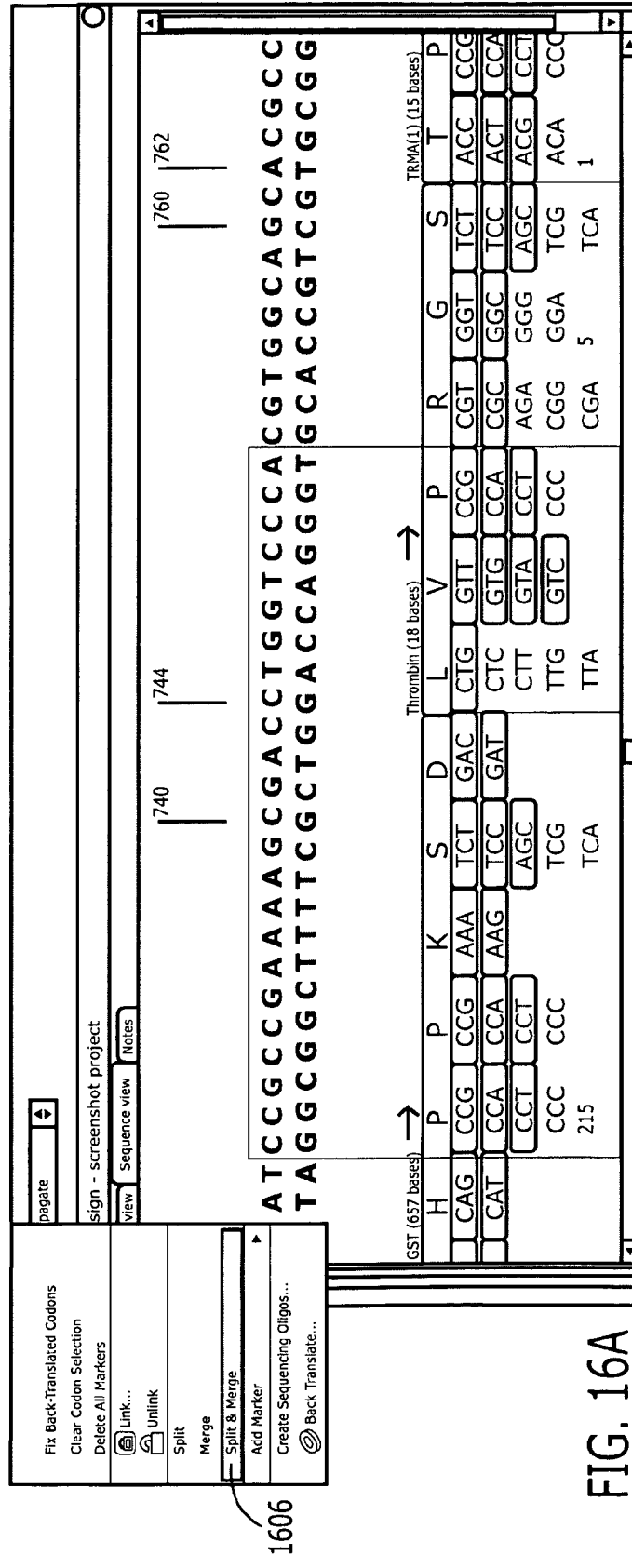

FIG. 16A highlights two partial sequence elements prior to a split and merge process in accordance with an embodiment of the present invention.

Figure 16B:
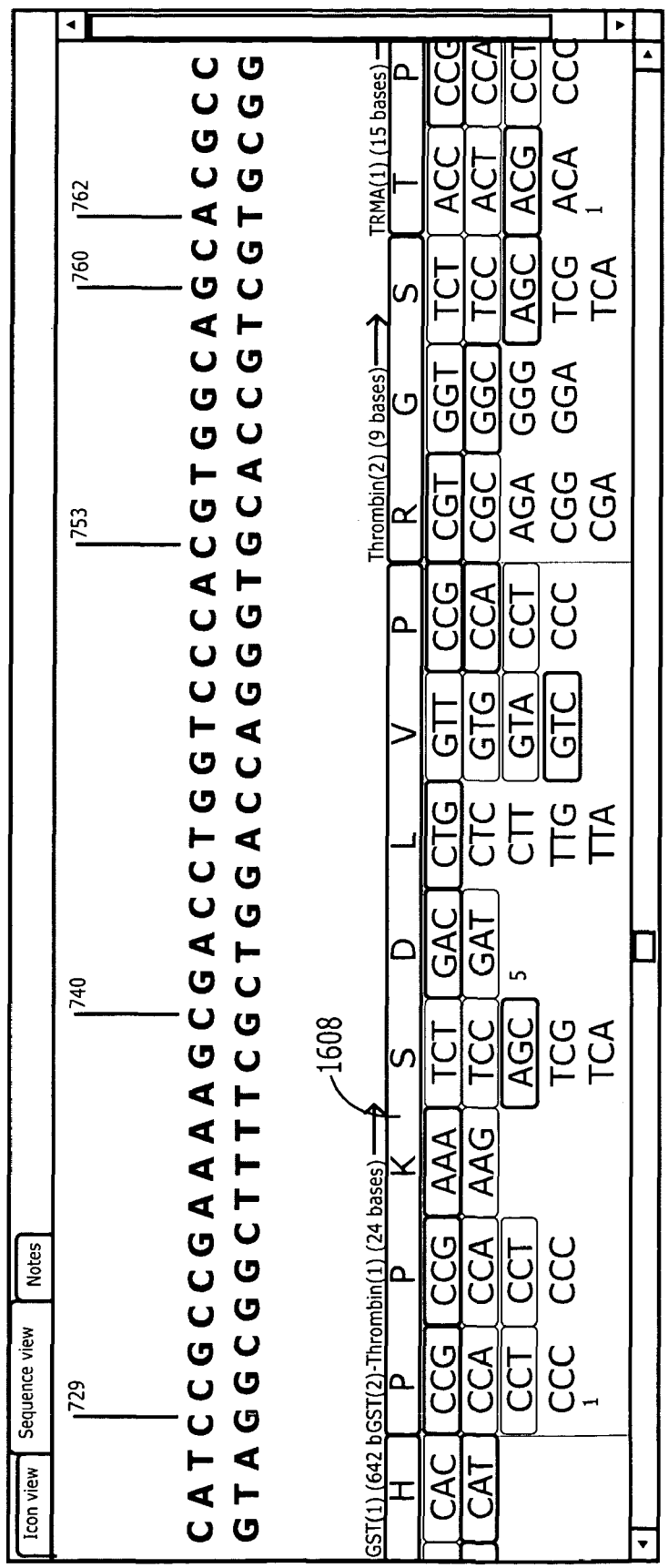

FIG. 16B illustrates the construction of a new sequence element, in sequence view, upon completion of a split and merge process in accordance with an embodiment of the present invention.

Figure 16C:
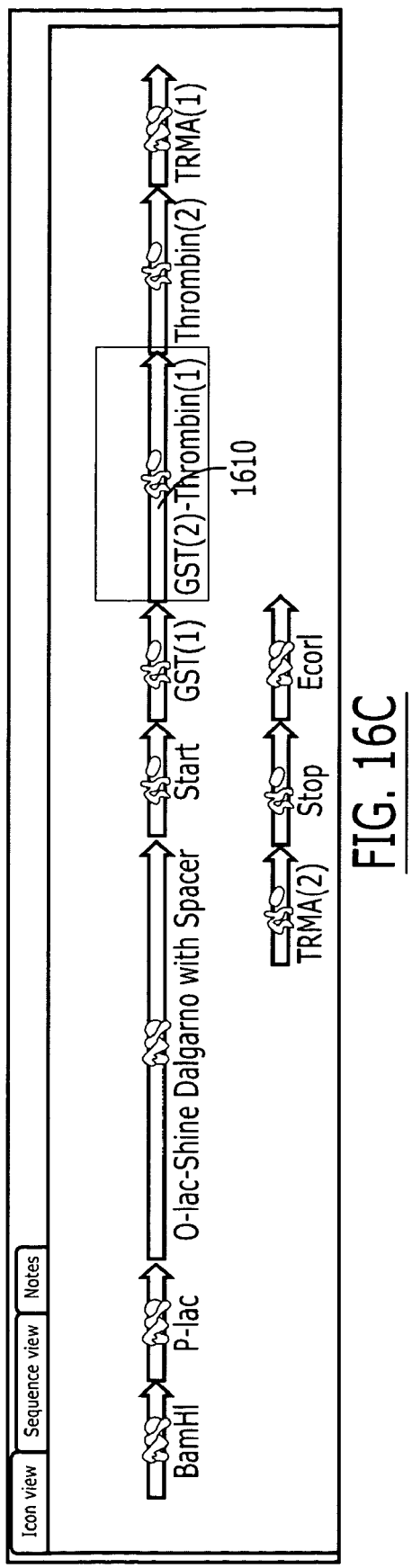

FIG. 16C illustrates the construction of a new sequence element, in icon view, upon completion of a split and merge process in accordance with an embodiment of the present invention.

Figure 17A:
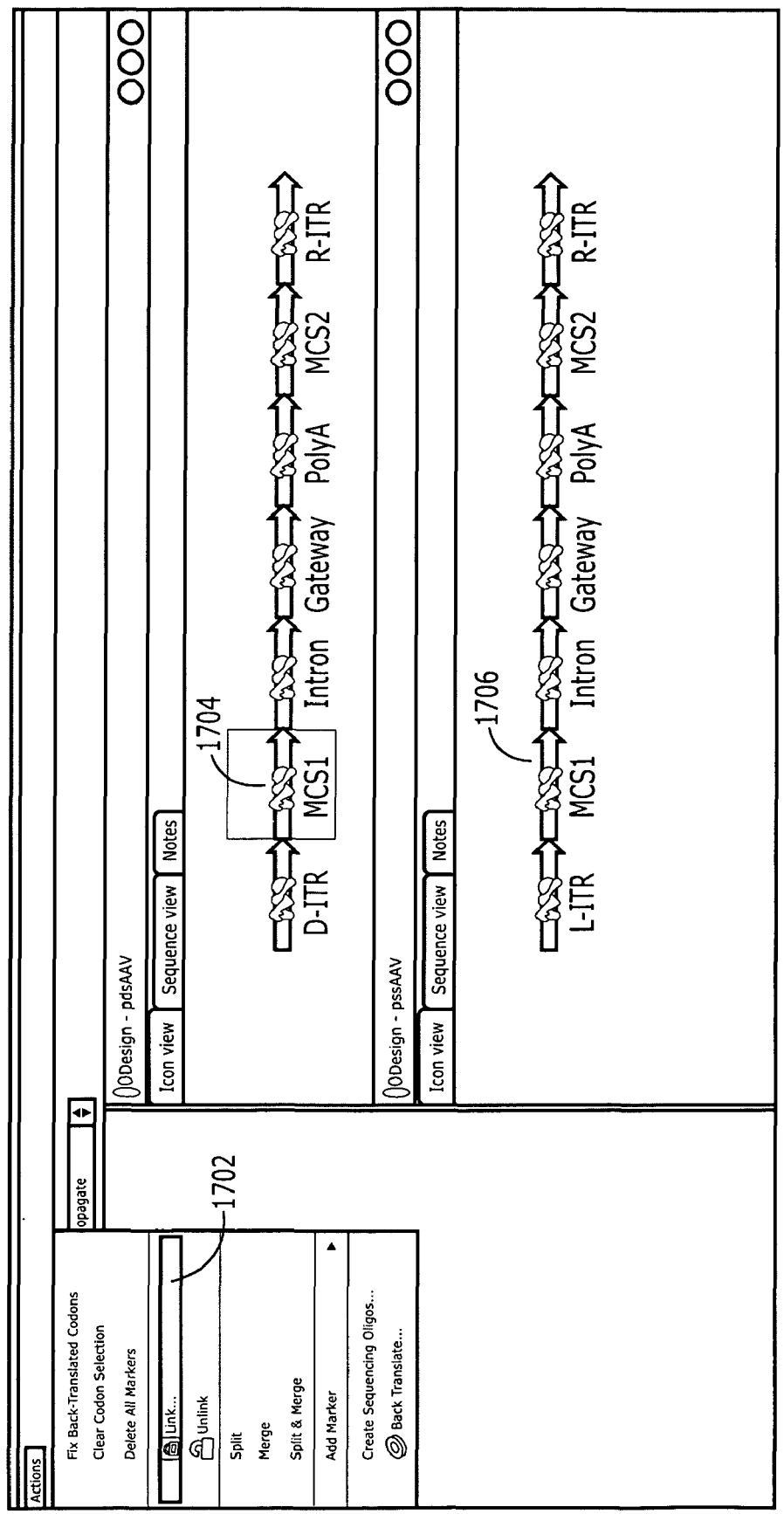

FIG. 17A highlights two sequence elements in icon view, prior to a link process in accordance with an embodiment of the present invention.

Figure 17B:
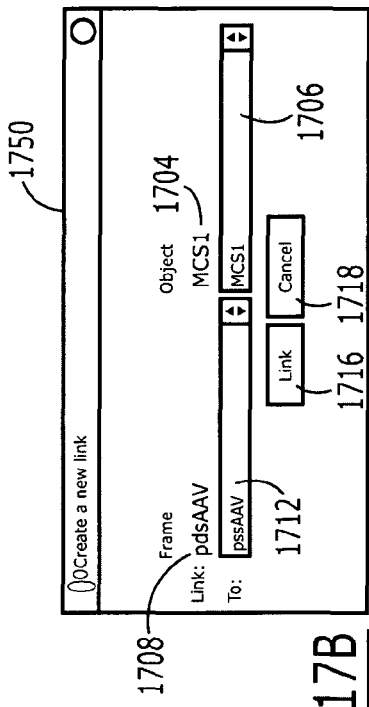

FIG. 17B illustrates a panel where a link can be specified between a target sequence element and any selected sequence element in accordance with an embodiment of the present invention.

Figure 17C:
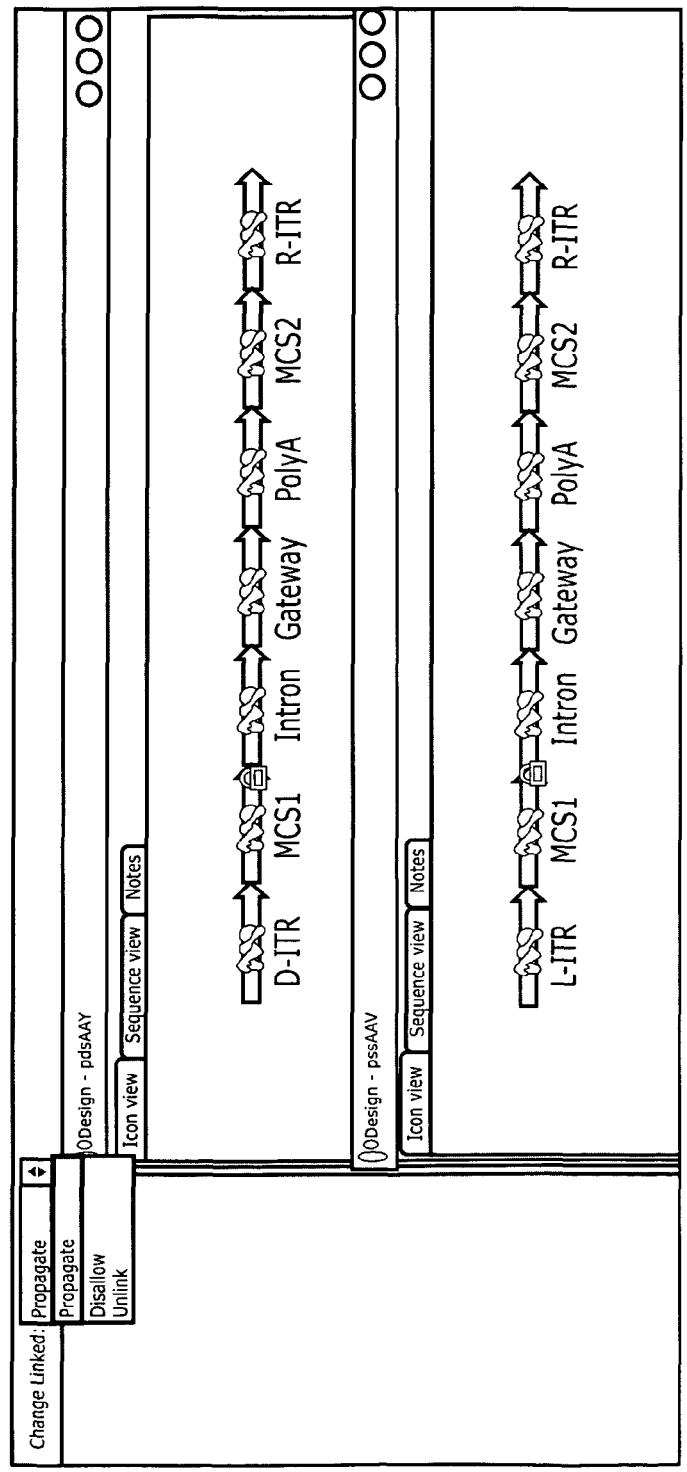

FIG. 17C illustrates how a link between two sequence elements is depicted in icon view in accordance with an embodiment of the present invention.

Figure 18A:
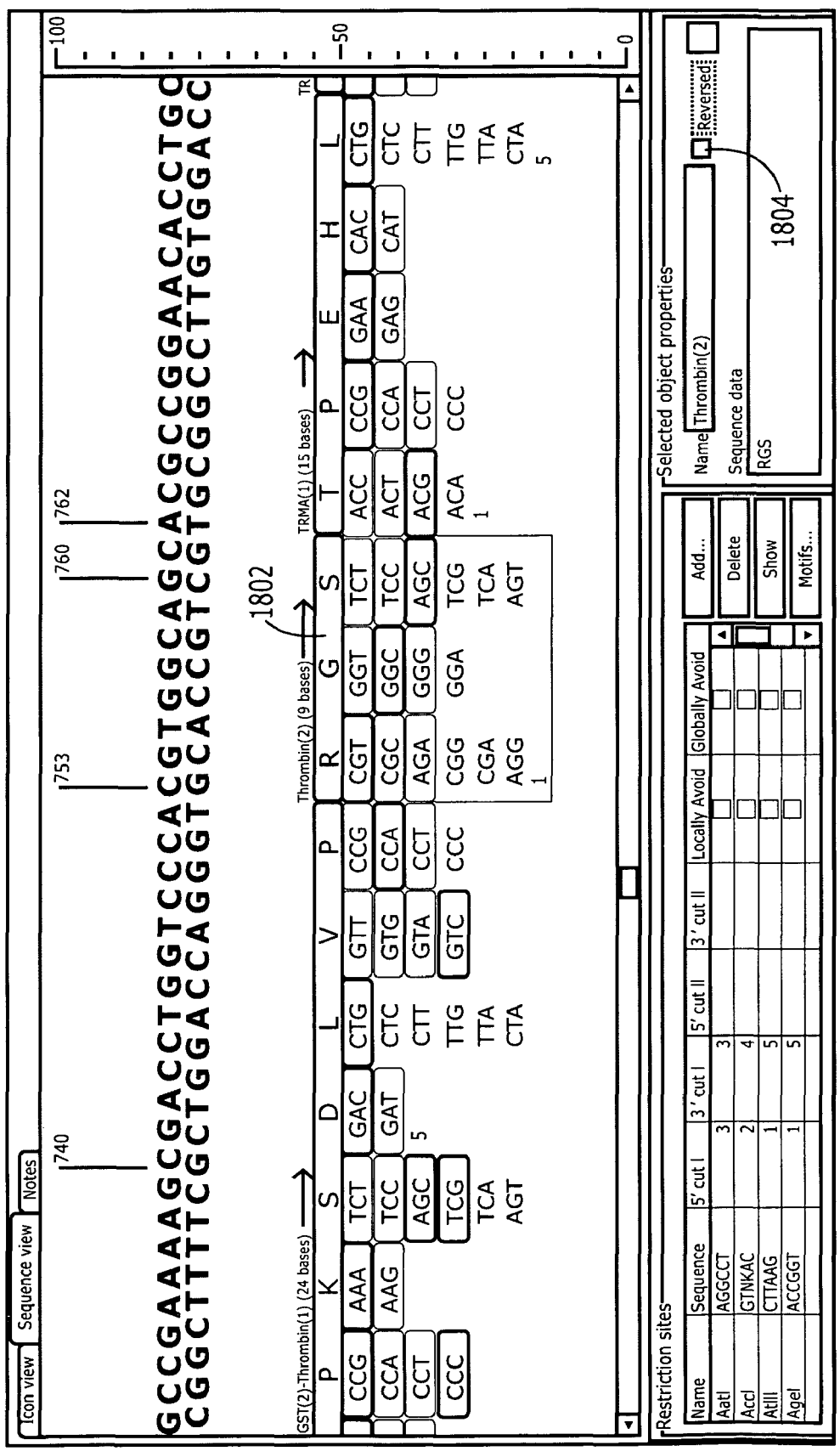

FIG. 18A highlights a sequence element in sequence view prior to a reverse direction process in accordance with an embodiment of the present invention.

Figure 18B:
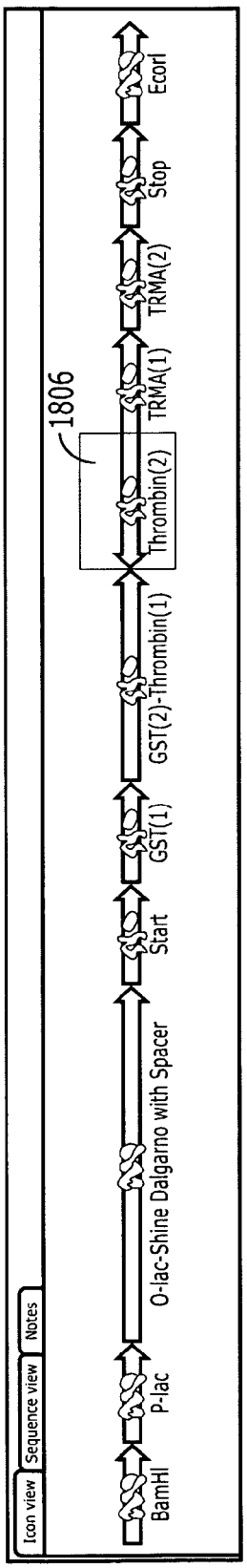

FIG. 18B displays the sequence element of FIG. 18A in its reversed form in icon view after application of the reverse process in accordance with an embodiment of the present invention.

Figure 18C:
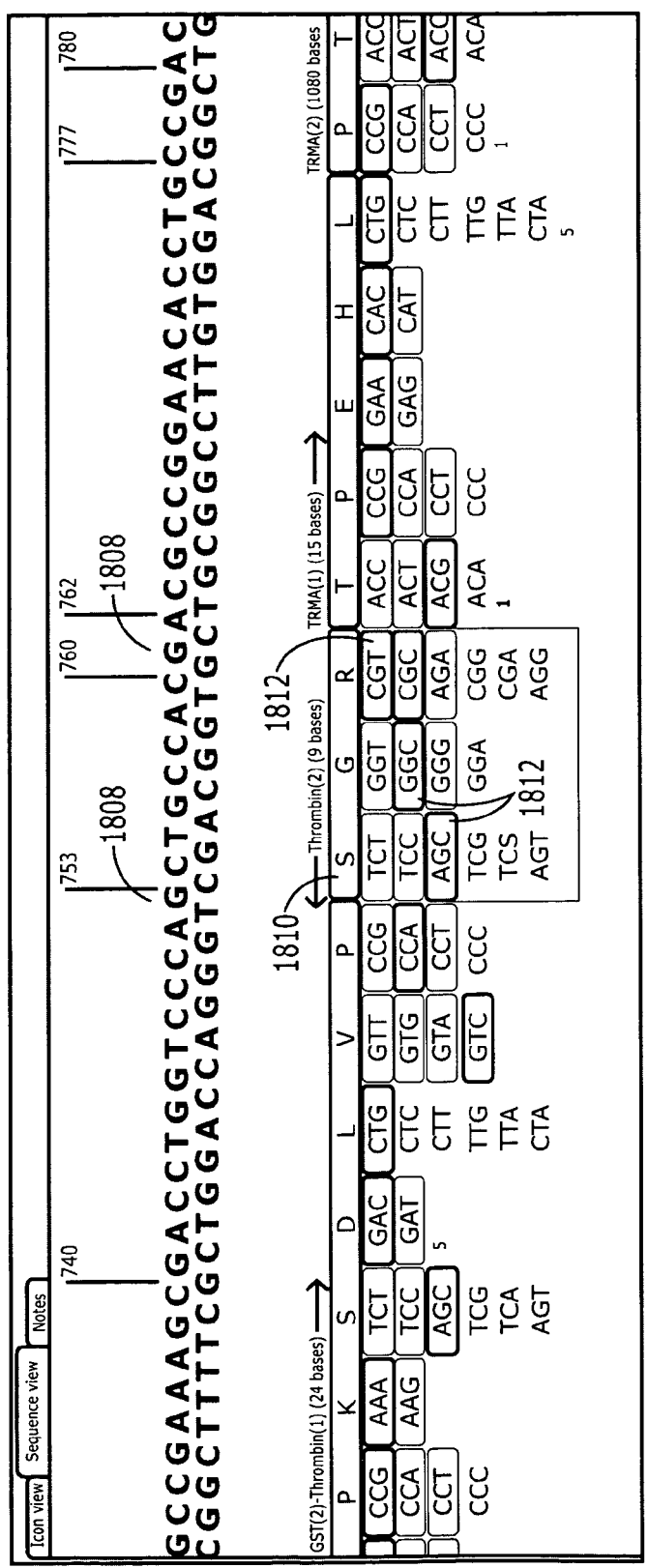

FIG. 18C displays the sequence element of FIG. 18A in its reversed form in sequence view after application of the reverse process in accordance with an embodiment of the present invention.

Figure 19A:
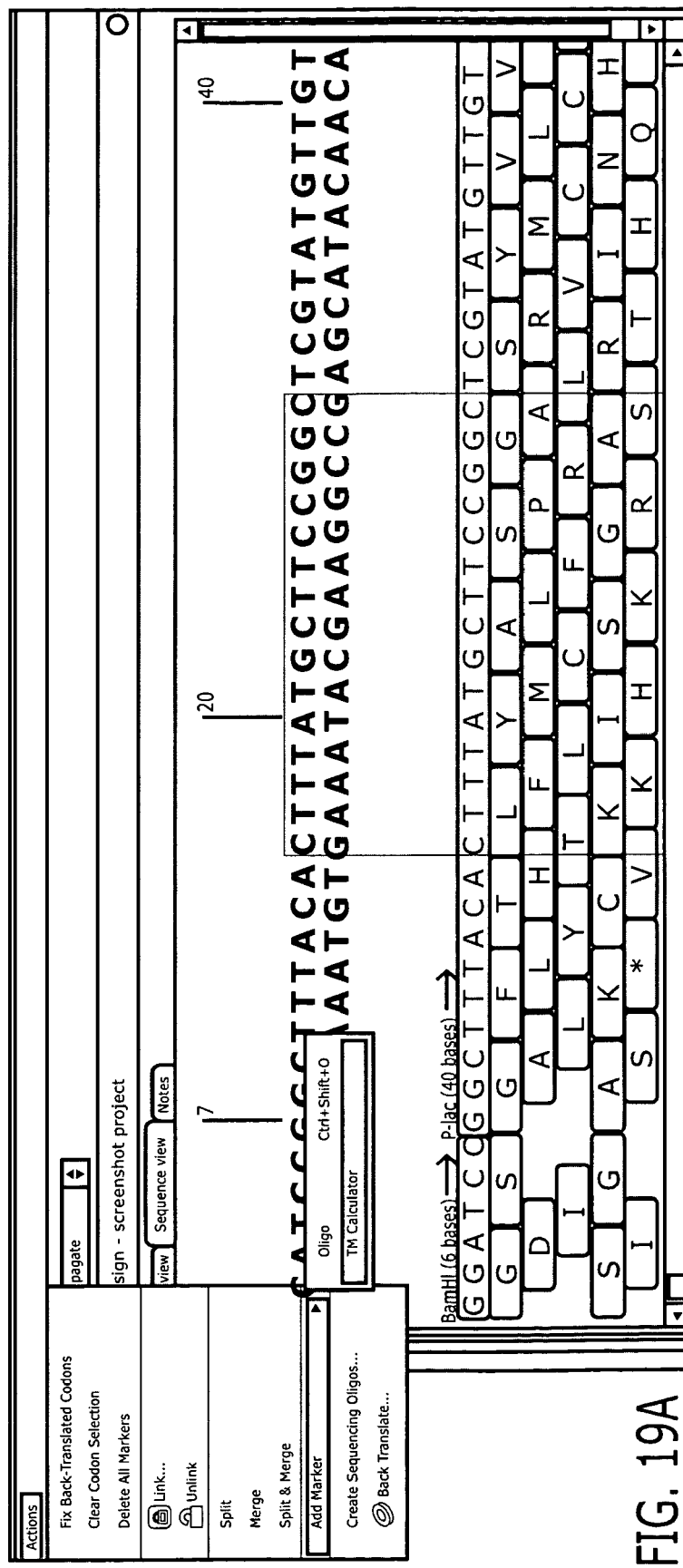

FIG. 19A illustrates how any portion of a design nucleic acid sequence can be selected in order to compute a melting temperature in accordance with an embodiment of the present invention.

Figure 19B:
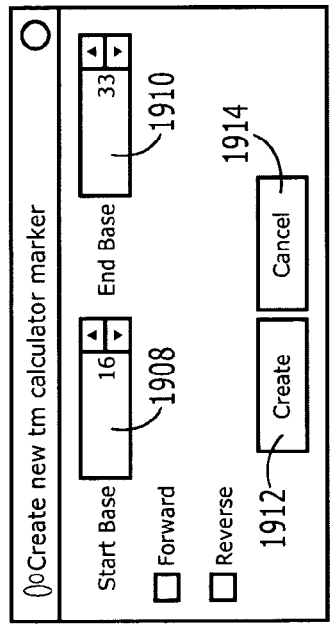

FIG. 19B illustrates a $T_m$ calculation window where the start and end bases in the design nucleic acid sequence are defined in order to compute a melting temperature in accordance with an embodiment of the present invention.

Figure 19C:
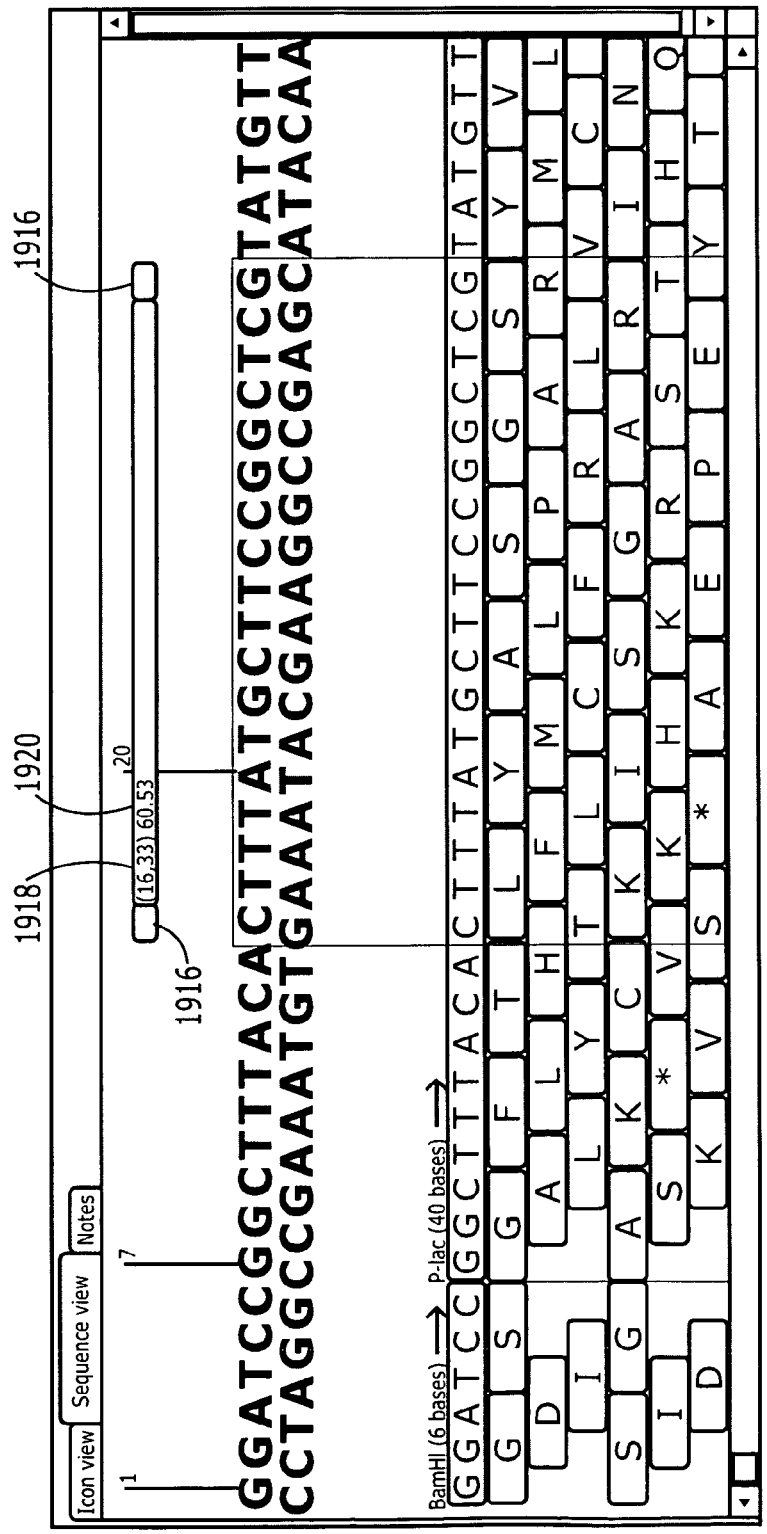

FIG. 19C illustrates how $T_m$ value can be calculated in real time for all or a portion of the design nucleic acid sequence interactively adjusting the positions of the start and end bases along the design nucleic acid sequence in accordance with an embodiment of the present invention.

Figure 20A:
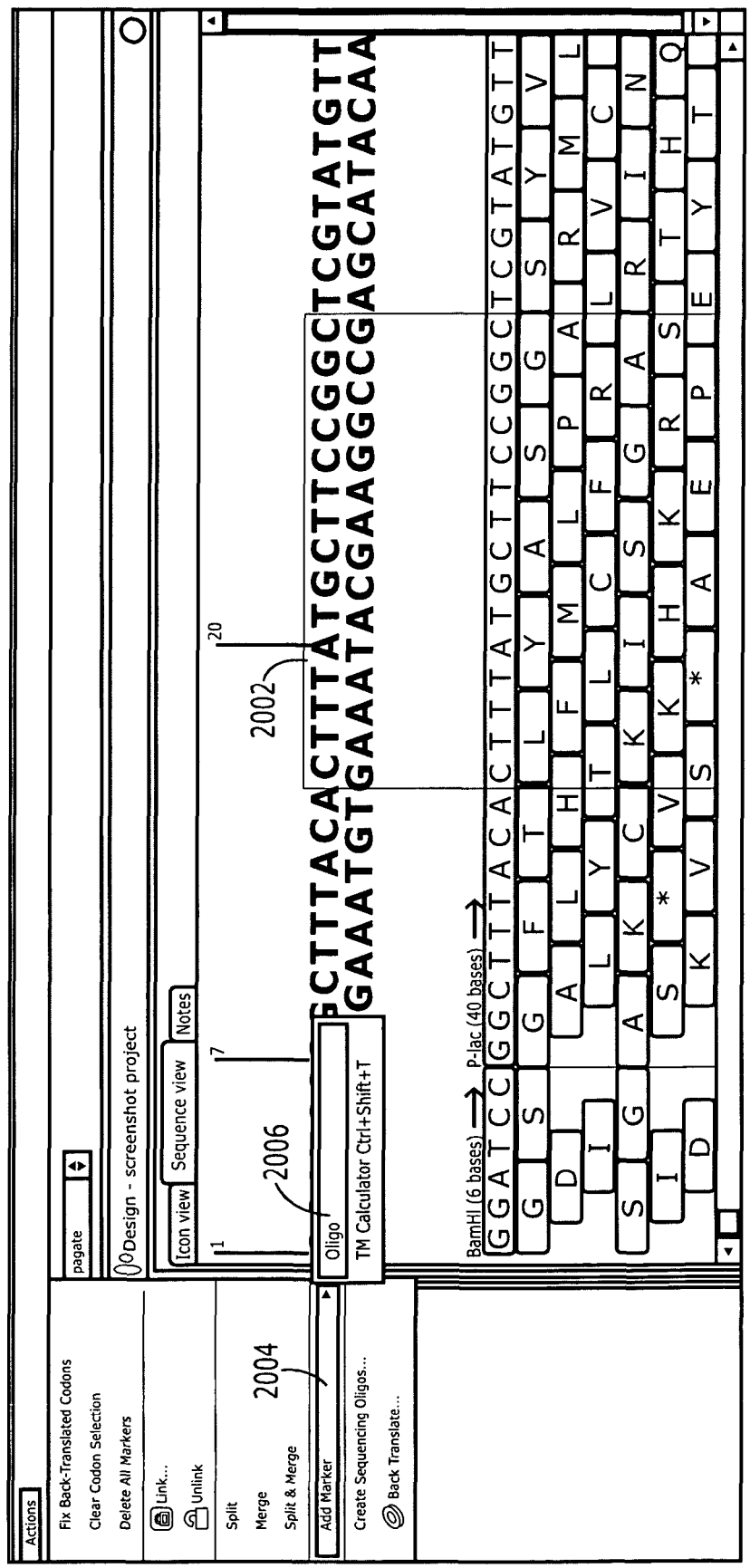

FIG. 20A illustrates how any portion of a design nucleic acid sequence can be selected in order to construct a corresponding oligonucleotide in accordance with an embodiment of the present invention.

Figure 20B:
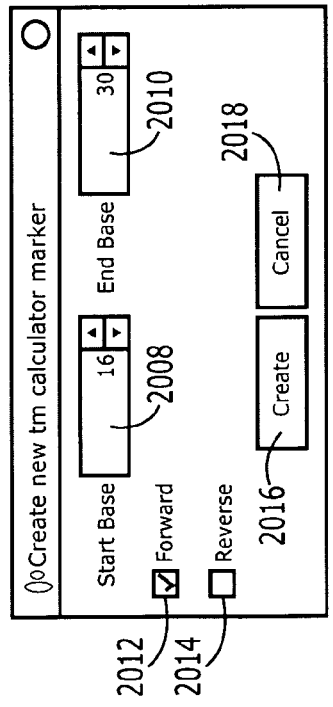

FIG. 20B illustrates an oligonucleotide calculation window where the start and end bases in the design nucleic acid sequence are defined in order to specify an oligonucleotide in accordance with an embodiment of the present invention.

Figure 20C:
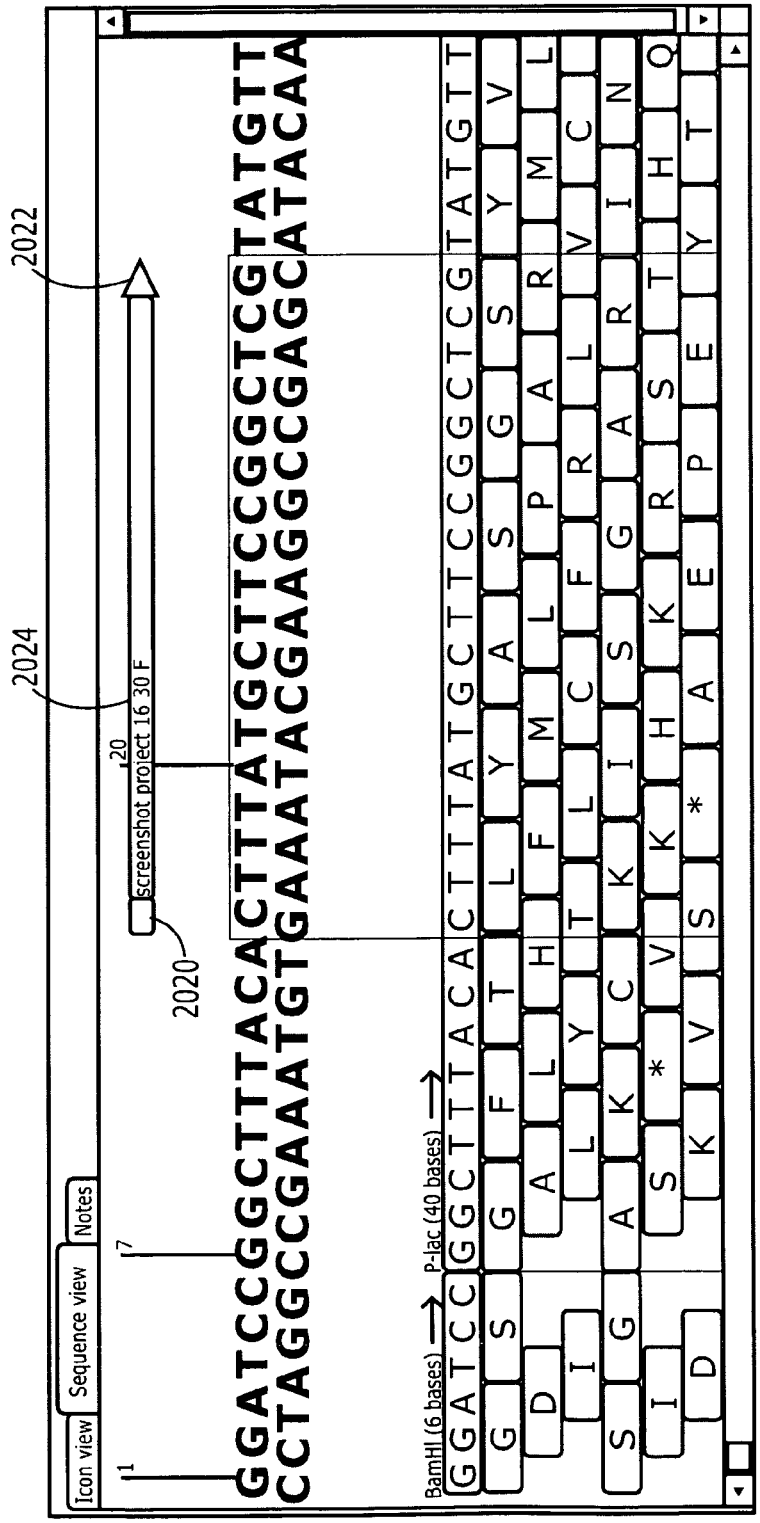

FIG. 20C illustrates how an oligonucleotide marker can be defined in real time by interactively adjusting the positions of the start and end bases along the design nucleic acid sequence in accordance with an embodiment of the present invention.

FIG. 21 illustrates a panel that provides options for providing a report in various formats in accordance with an embodiment of the present invention.

FIG. 22 illustrates options for a summary report in accordance with an embodiment of the present invention.

Figure 23:
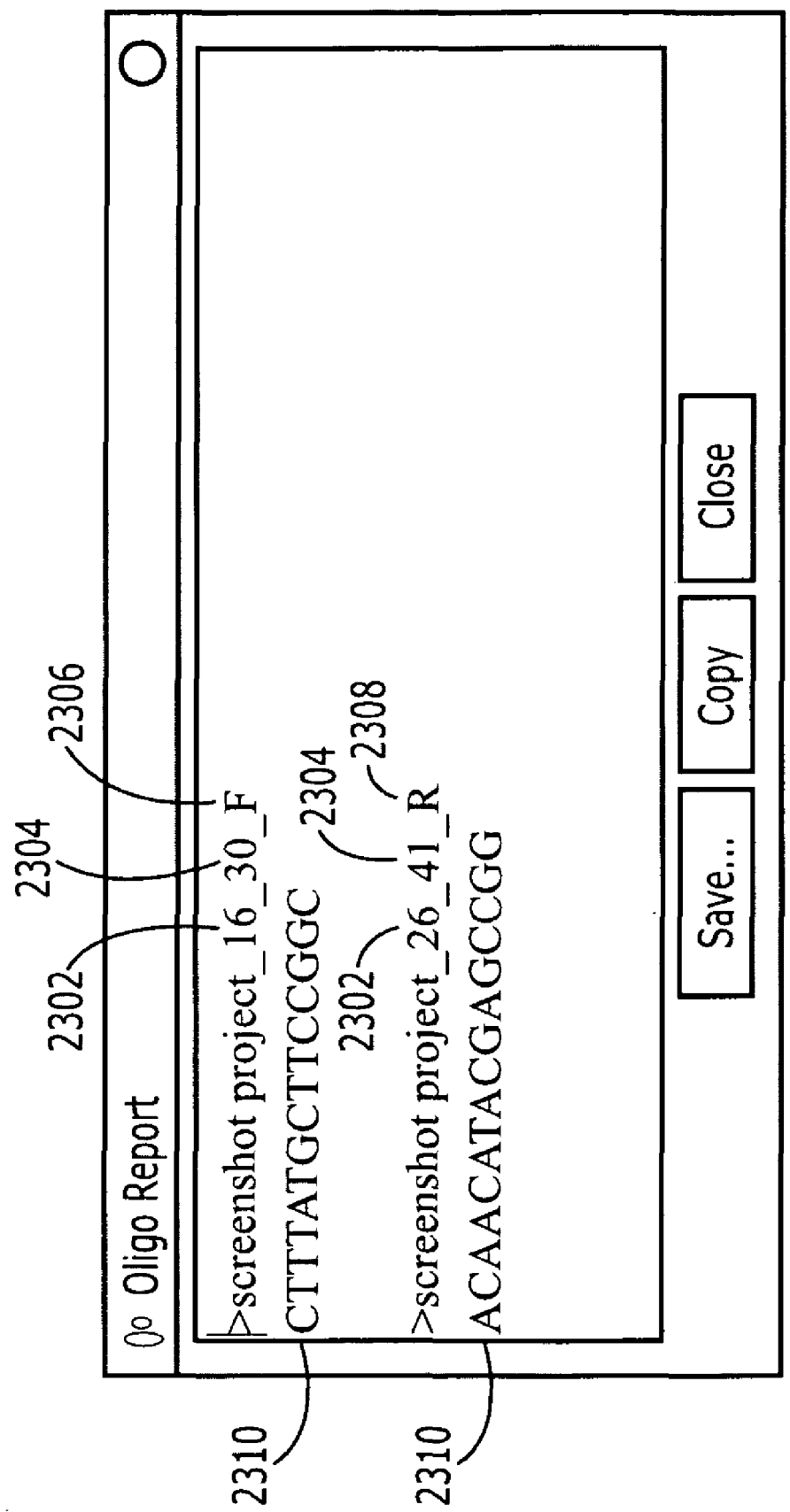

FIG. 23 illustrates an exemplary oligonucleotide report in accordance with an embodiment of the present invention.

5. DETAILED DESCRIPTION OF THE INVENTION

The present invention provides tools for designing and manipulating sequence elements in order to design polynucleotides encoding custom genetic constructs. Each sequence element represents an amino acid sequence segment or a nucleic acid sequence segment. A user defines a set of sequence elements. For example, one sequence element could be a promoter, another sequence element could encode a particular protein domain, and another sequence element could be a hexahistidine tag. These sequence elements can be obtained from a library, downloaded from the Internet, or newly constructed by typing in an amino acid sequence or nucleic acid sequence. The user drags each sequence element to be incorporated into the set of sequence elements onto a working pane in a graphical user interface. In the working pane, these sequence elements are represented as icons. In particular, each sequence element in the set of sequence elements is uniquely represented in the working pane by a corresponding icon. The user arranges the order of such icons in a linear or a near linear arrangement. In cases where there are too many icons to be arranged in a single row, multiple rows are formed. Neighboring icons in the linear arrangement represent neighboring sequence elements in the plurality of sequence elements. Each of the respective icons in the plurality of icons depict a directional property for the corresponding sequence element in the set of sequence elements.

Figure 1:
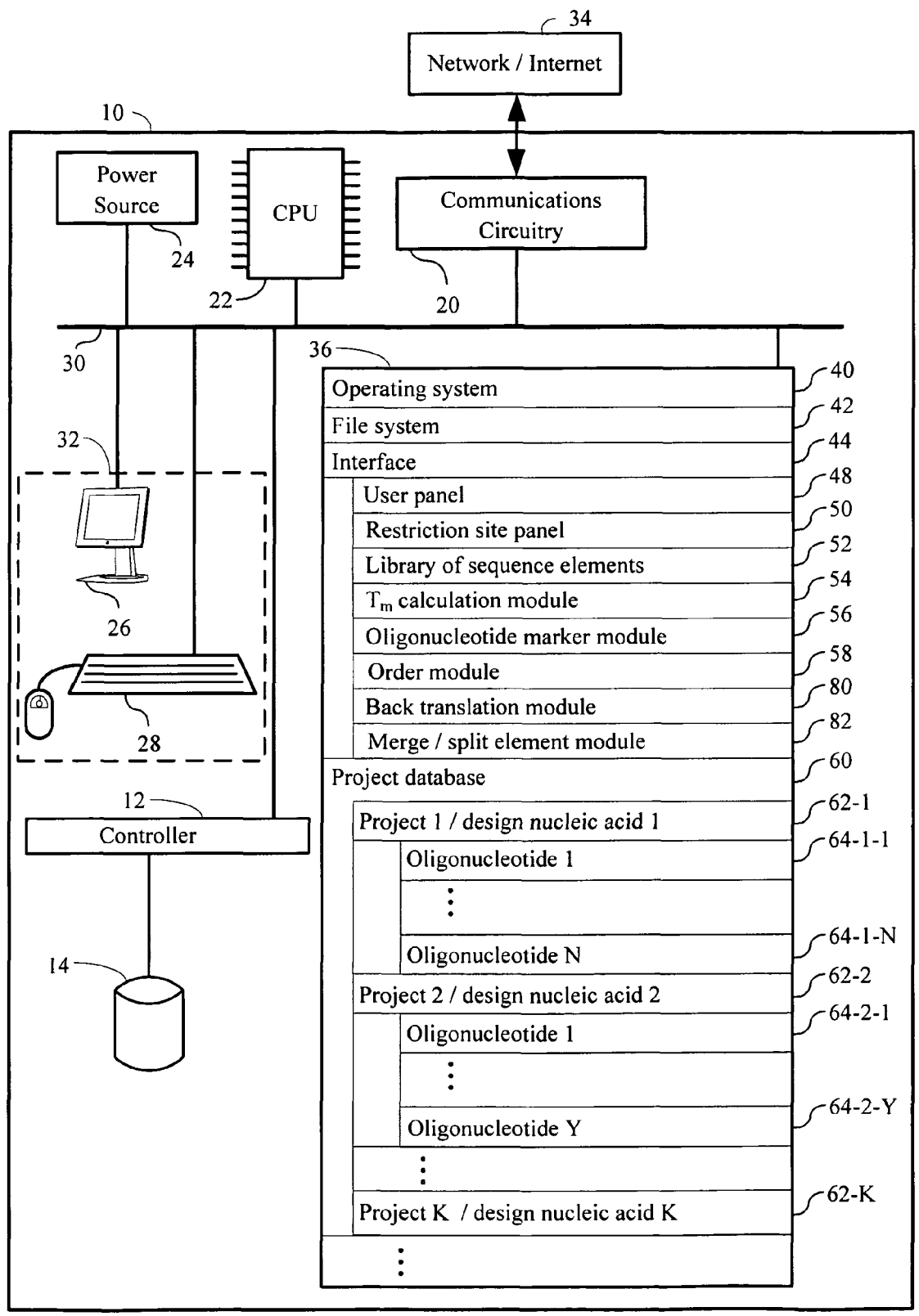
FIG. 1 illustrates a computer system in accordance with one embodiment of the present invention.

FIG. 1 details an exemplary system that supports the functionality described above. The system is preferably a computer system 10 having:
- a central processing unit 22;
- a main non-volatile storage unit 14, for example, a hard disk drive, for storing software and data, the storage unit 14 controlled by controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28) and a display 26 or other output device;
- a network interface card 20 or other communication circuitry for connecting to any wired or wireless communication network 34 (e.g., the Internet or any other wide area network);
- an internal bus 30 for interconnecting the aforementioned elements of the system; and
- a power source 24 to power the aforementioned elements.

Operation of computer 10 is controlled primarily by operating system 40, which is executed by central processing unit 22. Operating system 40 can be stored in system memory 36. In addition to operating system 40, in a typical implementation, system memory 36 can include one or more of the following:
- file system 42 for controlling access to the various files and data structures used by the present invention;
- an interface module 44 for identifying a set of sequence elements that collectively represent a design nucleic acid sequence; and
- a project database 60 for storing oligonucleotides associated with a plurality of projects 62.

In some embodiments, interface 44 includes a user panel 48 in which a plurality of icons are arranged in linear or near linear format. Each icon represents a sequence element in a set of sequence elements. A user drags sequence elements into the user panel 48 thereby adding the sequence elements to the set of sequence elements in a given project 62. Interface 44 further includes a restriction site panel 50 in which a plurality restriction enzymes and their corresponding recognition sequences are listed. A user can select individual restriction enzymes in order to either ensure that the corresponding recognition sequences are either incorporated or avoided in a design nucleic acid sequence. A user can create multiple instances of a user panel 48, each different instance associated with a different project 62 in project database 60. In preferred embodiments, each project 62 is stored as a separate file and the project database 60 is simply the directly or collection of directories where such files are located. Each project 62 includes a design nucleic acid that encodes a particular genetic construct.

As further illustrated in FIG. 1, interface 44 can access a library of sequence elements 52. Examples of sequence elements that can be found in library 52 include, but are not limited to, regulatory elements, expressed elements, and cloning elements. Exemplary regulatory elements include, but are not limited to, transcriptional elements (e.g., enhancers, promoters, operators, terminators, polyadenylation signals, etc.) and translational elements (e.g., 5' and 3' untranslated regions, ribosome binding sites, sequence elements that are initiation AUG contexts, termination codons, etc.). Exemplary expressed elements include, but are not limited to, peptide fusion tags, cleavage sites, solubility or fusion tags, and secretion signals. Exemplary cloning elements include, but are not limited to, restriction sites, recombinase recognition sequences and recombination sites. In some embodiments, the library of sequence elements is hierarchically divided, for example, by regulatory elements, expressed elements, and cloning elements. In some embodiments, the library of sequence elements is further divided according to organism of origin.

For each project 62, there is a corresponding design nucleic acid sequence that is collectively represented by a set of sequence elements. Advantageously, in the present invention, a user can select an arbitrary start and stop point in the design nucleic acid sequence and compute the $T_m$ of the oligonucleotide defined by these start and stop points using oligonucleotide marker module 56. Once a suitable design nucleic acid sequence has been constructed, the oligonucleotides 64 that form the design nucleic acid sequence, and more typically, the complete design nucleic acid sequence can be ordered over the Internet using order module 58.

The present invention provides various tools for constructing a design nucleic acid sequence from a given set of sequence elements. In typical embodiments, each sequence element in the set of sequence elements of a project corresponds to a portion of the design nucleic acid sequence. Some of these sequence elements are nucleic acid sequence elements that cannot be further back-translated by definition. However, other possible sequence elements are open reading frame elements and amino acid sequence elements that can be back-translated into the design nucleic acid sequence. A back translation module 80 is provided by interface 44 for this purpose. Back translation module 80 can use any suitable non-contradictory combination of the following criteria to effect the back-translation of an open reading frame element or an amino acid element:

(i) minimization of a repeated nucleic acid sequence in the design nucleic acid sequence;

(ii) avoidance of a predetermined nucleic acid sequence in the design nucleic acid sequence;

(iii) minimization of a secondary structure in the design nucleic acid sequence;

(iv) minimization of sequence identity of the design nucleic acid sequence with respect to a reference sequence or maximization of sequence identity with respect to the reference sequence;

(v) avoidance of an enzyme recognition sequence in the design nucleic acid sequence;

(vi) selection of a codon based on codon frequency specified by a codon table;

(vii) elimination of a methylation site that would inhibit the action of an enzyme in the design nucleic acid sequence; and (viii) avoidance of a first subsequence in the design nucleic acid sequence that has an annealing temperature with a second subsequence in the design nucleic acid sequence that is above a predetermined value.

Sequence elements in a set of sequence elements can be split apart or merged together by merge/split element module 82 of interface 44. In fact, in a spit and merge operation, a user can select all or a portion of one or more contiguous sequence elements, split them from their parent sequence elements and unite them into a new sequence element, whereupon the sequence in the new sequence element is removed from the parent sequence elements. Parent sequence elements that have no remaining sequence after such removal are then removed.

Computer 10 comprises software program modules and data structures. The data structures stored in computer 10 include, for example, the library of sequence elements 52 and projects 62. Each of these data structures can comprise any form of data storage including, but not limited to, a flat ASCII or binary file, an Excel spreadsheet, a relational database (SQL), or an on-line analytical processing (OLAP) database (MDX and/or variants thereof). In some embodiments, each of the aforementioned data structures are stored on or are accessible to system 10 as single data structures. In other embodiments, such data structures, in fact, comprise a plurality of data structures (e.g., databases, files, archives) that may or may not all be hosted by computer 10. For example, in some embodiments, the library of sequence elements 52 is a plurality of structured and/or unstructured data records that are stored either on computer 10 and/or on computers that are addressable by computer 10 across network/Internet 34.

In some embodiments, the library of sequence elements 52 and/or projects 62 are either stored on computer 10 or are distributed across one or more computers that are addressable by computer 10 by network/Internet 34. Thus, in some embodiments, one or more of such data structures is hosted by one or more remote computers (not shown). Such remote computers can be located in a remote location or in the same room or the same building as computer 10. As such, any arrangement of the data structures and software modules illustrated in FIG. 1 on one or more computers is within the scope of the present invention so long as these data structures and software modules are addressable by computer 10 across network/Internet 34 or by other electronic means. Moreover, other systems, application modules and databases not shown in FIG. 1 can be stored in system memory 36. Thus, the present invention fully encompasses a broad array of computer systems.

Figure 2:
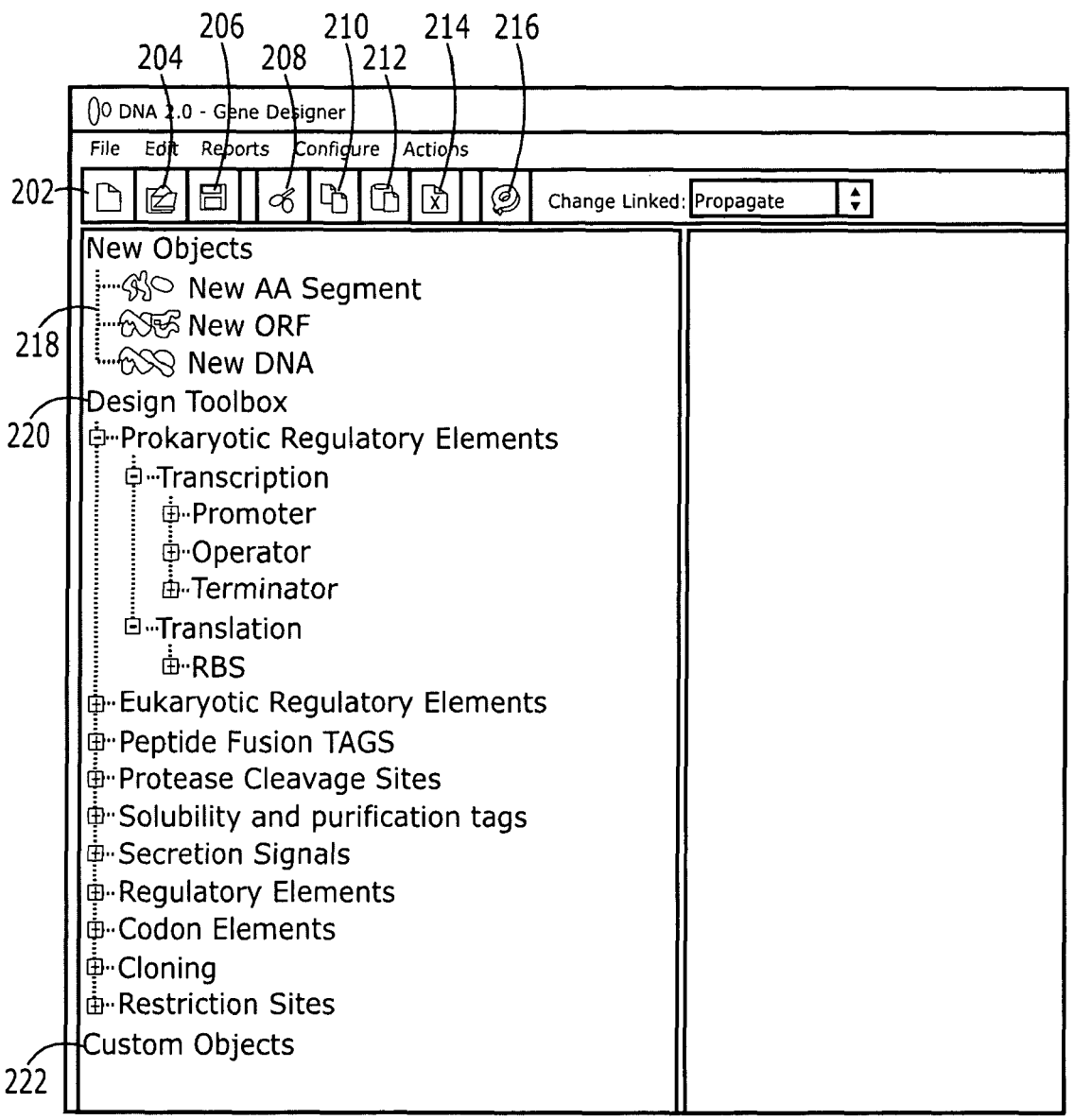
FIG. 2 depicts a top-level overall interface in accordance with one embodiment of the present invention.

FIG. 2 depicts a top-level user interface 44 in accordance with an embodiment of the present invention. A user creates a new design by selecting element 202. Element 204 allows a user to open an existing project. A user can save a project by selecting element 206. At the level depicted in FIG. 2, a user also has many options for manipulating sequence elements. For example, element 208 cuts selected sequences, element 210 copies selected sequences, element 212 pastes selected sequences, and element 214 deletes selected sequences. Option 216 back-translates amino acid sequences to corresponding DNA sequences. Option 218 allows users to add sequence elements into any open design projects.

Figure 5:
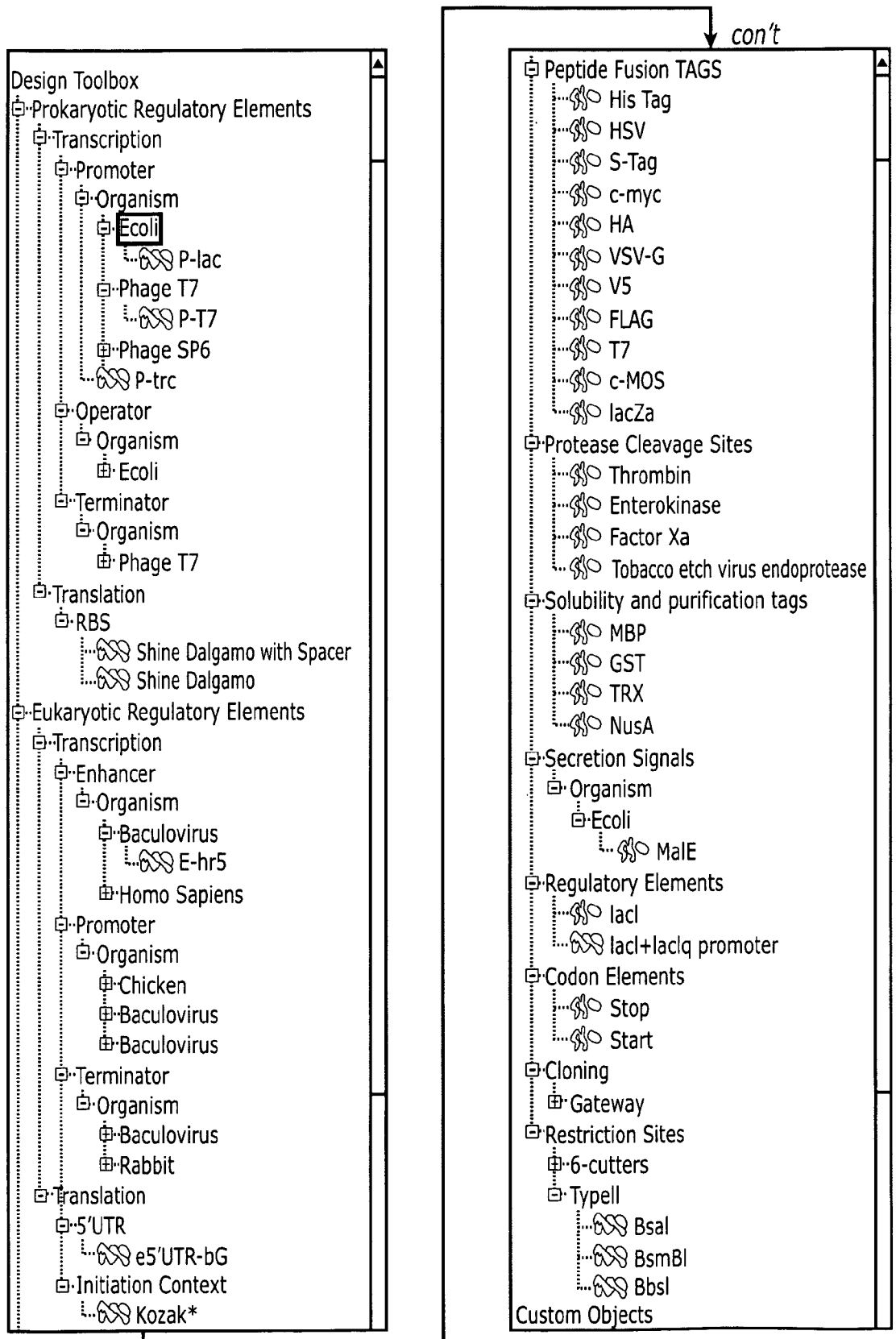
FIG. 5 illustrates sequence elements in a hierarchical tree organization in accordance with an embodiment of the present invention.

Design toolbox 220 provides a comprehensive toolset for pre-designed sequence elements. A user can add a wide variety of sequences elements to any open design projects. Examples include, but are not limited to, known prokaryotic transcriptional regulatory elements (e.g., promoters, operators, terminators, etc.), prokaryotic translational regulatory elements (e.g., ribosome binding sites, etc.), eukaryotic transcriptional regulatory elements (e.g., enhancers, operators, terminators, etc.), eukaryotic translational regulatory elements (e.g., 5N un-translated regions, initiation contexts, etc.), peptide fusion tags (e.g., His-Tag, HSV, S-Tag, c-myc, HA, VSV-G, V5, FLAG, T7, c-MOS, lacZa, etc.), protease cleavage sites (e.g., thrombin, enterokinase, factor Xa, tobacco etch virus endoprotease, etc.), solubility and purification tags (e.g., maltose binding protein, glutathione S-transferase, TRX, NusA, etc.), secretion signals (e.g., *E. coli* MalE to direct expressed protein to the periplasmic space for purification purposes), regulatory elements (e.g., LacI, LacI plus Lacq promoters), standard regulatory elements (e.g., start and stop codons), cloning gateways (e.g., standard 5N and 3N attB1 and attB2 inserts from Invitrogen, Carlsbad, Calif.), and restriction sites (e.g., six cutters, typeII cutters, etc.). The custom objects element 222 provides a comprehensive tool set for custom designed sequence elements. By clicking on the sub-icons within custom object element 222, a user can add custom nucleic acid or amino acid sequences. FIG. 5 illustrates how such sequences elements can be organized in a hierarchical tree.

Figure 3:
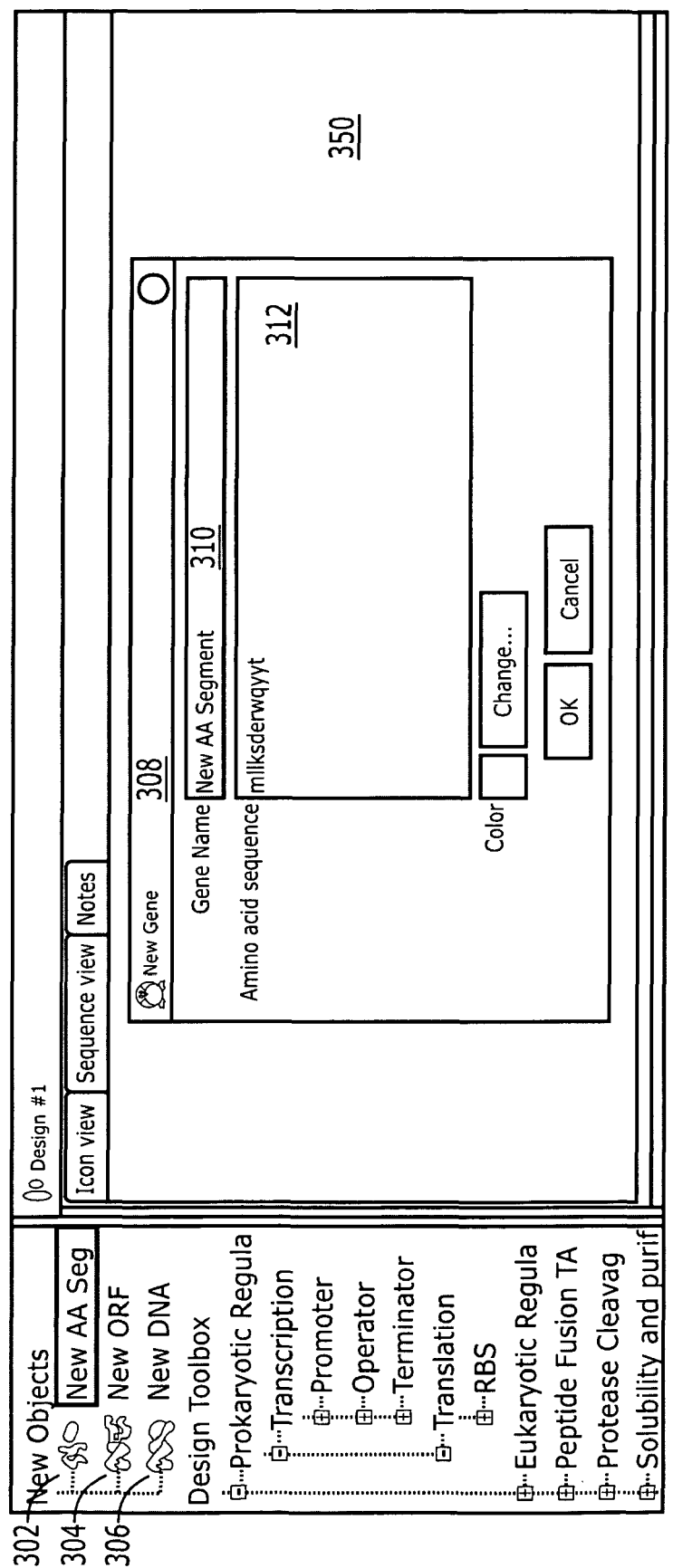
FIG. 3 illustrates the creation of a new amino acid element in accordance with an embodiment of the present invention.

Referring to FIG. 3, once a new design project has been created, a user can select a new sequence element thereby creating a new sequence element window 308 with space for a name 310 and a sequence 312. There are three types of sequence elements, amino acid sequence elements 302, open reading frame sequence elements 304, and nucleic acid sequence elements 306. Amino acid sequence elements 302 are defined by an amino acid sequence and are subject to back-translation, a process in which this amino acid sequence is back-translated using specified design criteria into an optimal nucleic acid sequence. This optimal nucleic acid sequence forms part of the design nucleic acid for a given project. Open reading frame sequence elements 304 are nucleic acid sequence elements that can be subjected to further optimization. Nucleic acid sequence elements are nucleic acid sequences that are fixed and are not subjected to further optimization. Once the user has constructed or selected a sequence element, it is dropped onto user panel 350 (user panel 48 of FIG. 1) and to become part of the project represented by the user panel.

Open reading frame sequence elements are entered as nucleic acid sequences. They are automatically translated to a corresponding amino acid sequence. The nucleic acid sequence can be fixed at the time of entry, in which case it is not affected by subsequent back-translation. If the nucleic acid sequence is not fixed, the amino acid sequence will be back-translated at the back-translation step.

In some embodiments, amino acid sequence elements 302 accept one letter code for each of the naturally occurring twenty amino acids. In some embodiments, open reading frame elements 304 and nucleic acid sequence elements 306 accept one letter code for the four naturally occurring bases and non-standard characters are filtered out.

Figure 4:
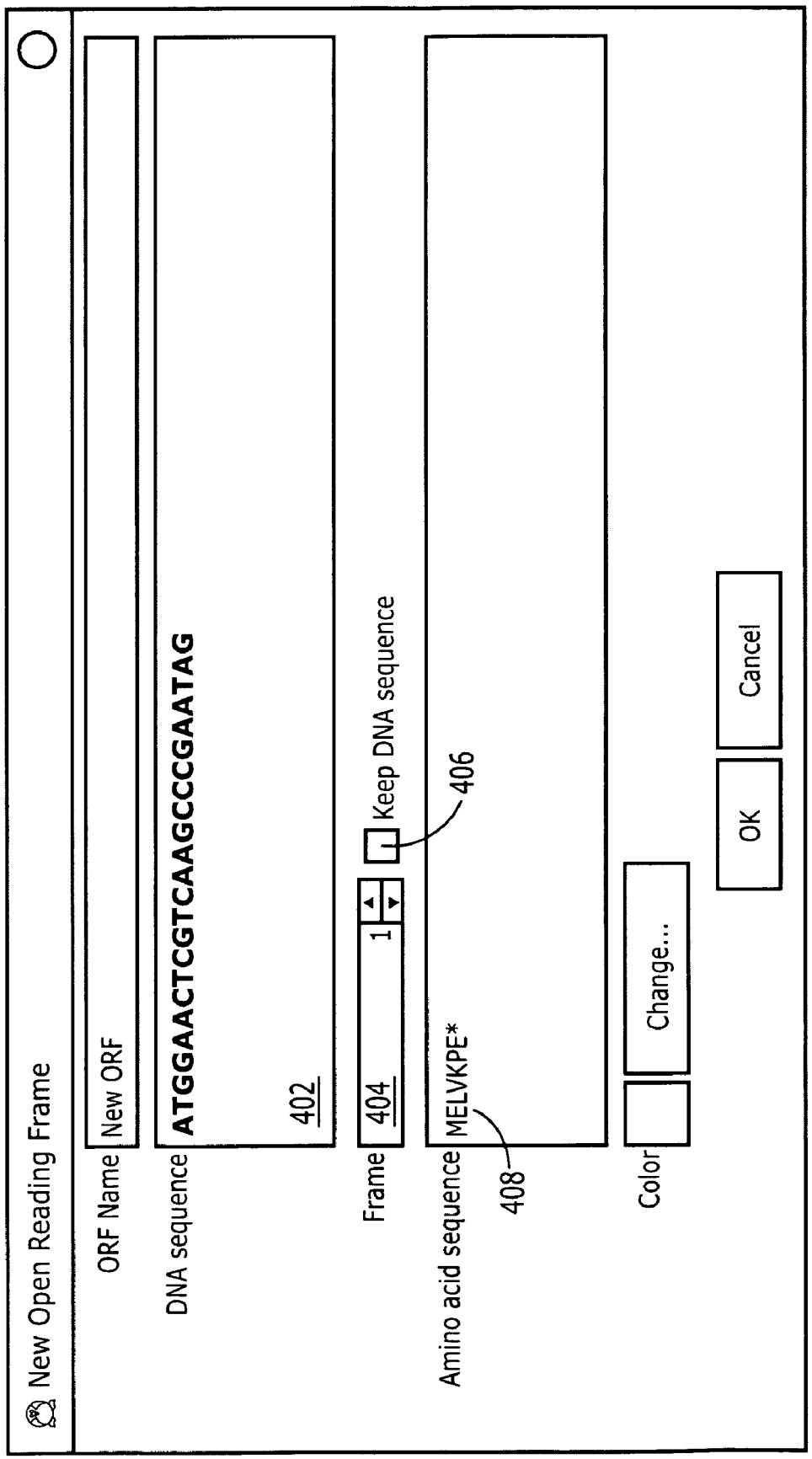
FIG. 4 illustrates the creation of a new open reading frame element in accordance with an embodiment of the present invention.

Referring to FIG. 4, open reading frame sequence elements are entered as a nucleic acid sequence 402. A reading frame for the sequence element can be selected using toggle 404. Toggle 404 defines whether the first codon starts at the first, second or third base. The amino acid sequence that corresponds to nucleic acid sequence 402 is displayed in panel 408. Toggle 406 can be used to toggle between a state in which nucleic acid sequence 402 is fixed and an alternate state in which the nucleic acid sequence can be subjected to optimization by back-translation.

Figure 6:
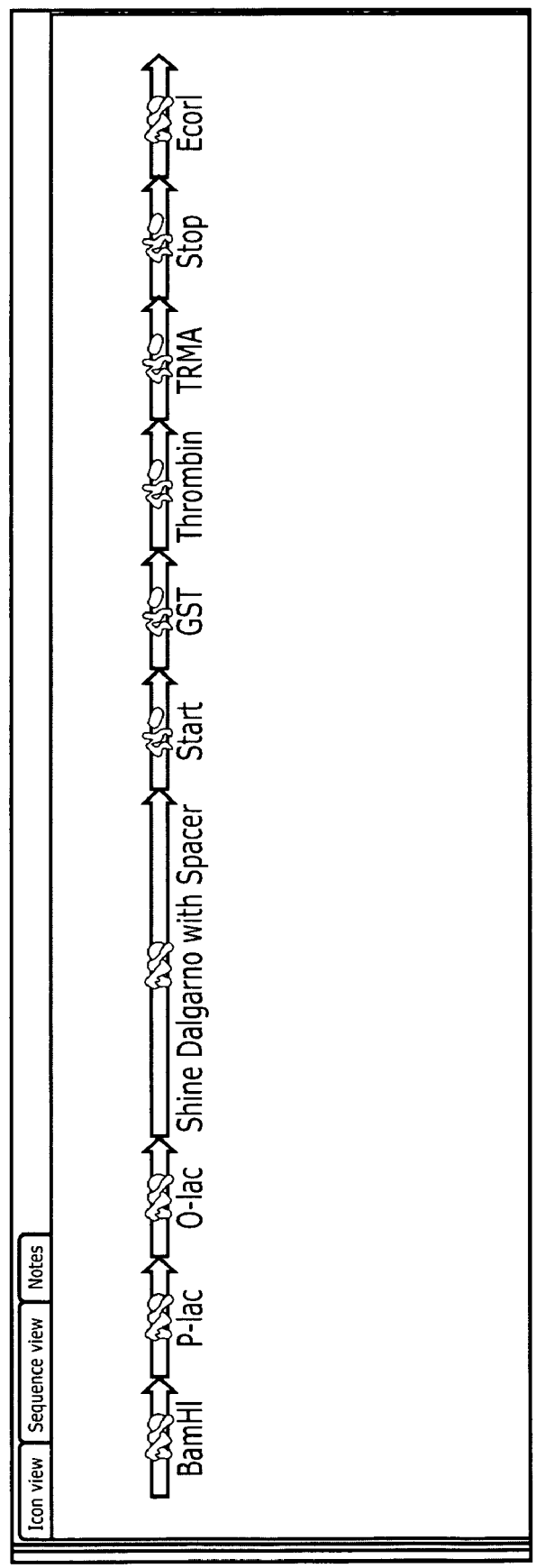
FIG. 6 illustrates a set of sequence elements represented as a corresponding plurality of icons in a linear or near linear arrangement in accordance with an embodiment of the present invention.

In the systems and methods of the present invention, a user creates a project and identifies or creates a set of sequence elements. As noted above, each sequence element is an amino acid sequence element, an open reading frame element, or a nucleic acid sequence element. Each sequence element represents an amino acid sequence segment or a nucleic acid sequence segment. The set of sequence elements are collectively represented by a design nucleic acid sequence. Referring to FIG. 6, a plurality of icons is displayed in a linear or a near linear arrangement. Each respective icon in the plurality of icons uniquely represents a corresponding sequence element in the set of sequence elements defined by the user. Neighboring icons in the plurality of icons represent neighboring sequence elements in the plurality of sequence elements. Each respective icon in the plurality of icons depicts a directional property (e.g., a translation direction or a transcription direction) for the corresponding sequence element in the set of sequence elements.

Icons can be displayed in an icon view or a sequence view. When the icons are displayed in icon view, a graphical depiction of each sequence element represented by the icons is displayed as illustrated in FIG. 6. When icons are displayed in sequence view, a sequence represented by each icon is displayed, as illustrated, for example, in FIG. 7. In icon view, each sequence element can be represented by an icon. The order of the icons can be altered using, for example, mouse drag operations.

Figure 7:
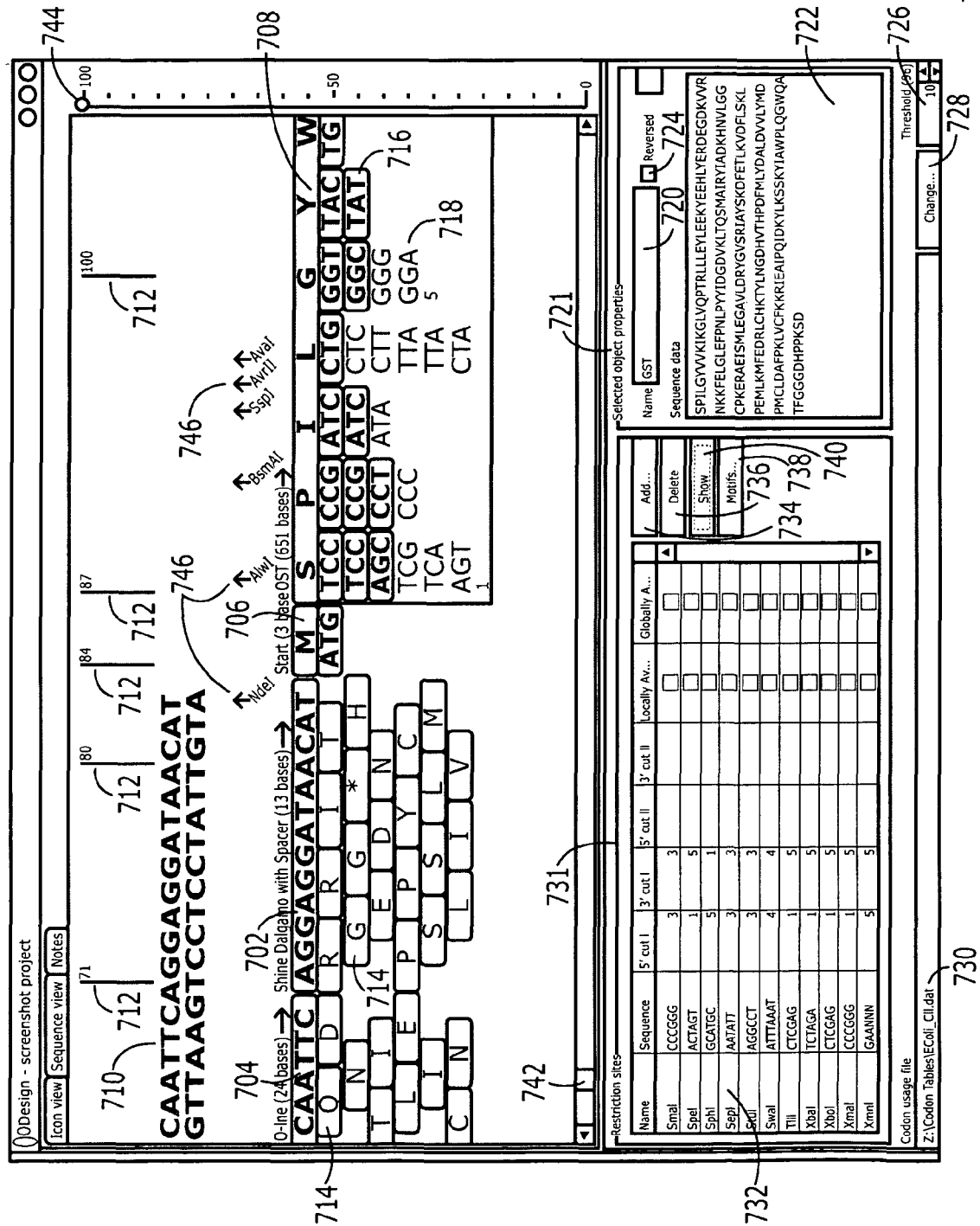
FIG. 7 illustrates sequence elements displayed in sequence view in accordance with an embodiment of the present invention.

Referring to FIG. 7, in sequence view, icons 702 and 704 represent nucleic acid sequence elements and icons 706 and 708 represent amino acid sequence elements. The name of each sequence element is provided above its corresponding icon. There is a design nucleic acid sequence 710 that corresponds to the set of sequence elements. For each icon, the icon's start position and end position within this design nucleic acid sequence is depicted. There is also a marker in the design nucleic acid sequence at uniform intervals (every 20 bases in FIG. 7). These start, end, and interval markers are denoted as elements 712 in FIG. 7. In FIG. 7, the amino acid sequence elements represented by icons 706 and 708 have not been back-translated yet. Accordingly, the design nucleic acid sequence is blank for these sequence elements.

For nucleic acid sequence elements, the amino acid sequence resulting from translation of that sequence is shown in all six reading frames 714. This allows rapid assessment of reading frames when combining amino acid and nucleic acid sequence elements. For each respective amino acid in an amino acid sequence element, each codon corresponding to the respective amino acid is displayed below the respective amino acid. The codons for each amino acid are ranked according to use in a selected expression organism, as specified by a codon bias table. The codon bias table in use is indicated 730 and can be changed 728. A threshold 726 can be set to exclude codons that are used below a certain frequency in the selected organism. For example, in FIG. 7, threshold 726 has been set to ten percent meaning that codons that appear with a frequency of less then ten percent will not be used to construct the portion of the design nucleic acid sequence that corresponds to the amino acid sequence elements.

The codons for each amino acid are also color-coded, with those found at a frequency in the selected codon bias table above the selected threshold depicted in one color 716, and those found at a frequency in the selected codon bias table below the selected threshold in another color 718. A sequence element can be selected. For example, in FIG. 7, sequence 708 has been selected. This displays its characteristics in an editing box 721. Editing box 721 contains the element name 720, sequence 722 and an option that allows the reversal of the element direction 724.

A restriction site analysis box 731 (panel 50 of FIG. 1) displays restriction enzyme recognition sequences 732. The list in restriction analysis box 731 can be modified by additions 734 or deletions 736, and other motifs can be added 738. Furthermore, selected restriction sites can be shown within the sequence 740. Places within amino acid sequence element or open reading frame sequence elements where restriction sites could occur without altering the amino acid sequence are indicated 746 in their corresponding position in the design nucleic acid sequence. The view of the sequences can be altered by scrolling through the sequence 742, or by altering the magnification 744 of the sequence.

Figure 8A:
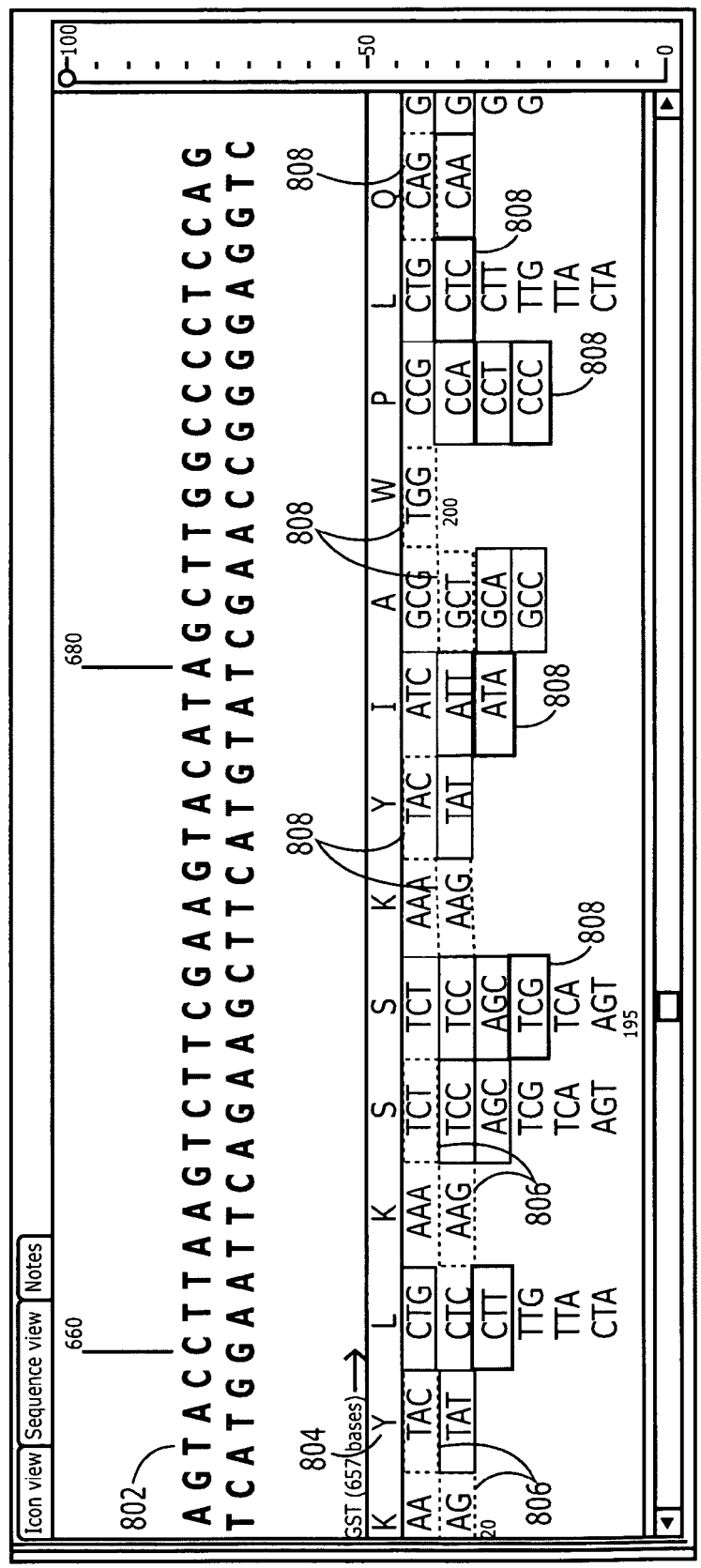
FIG. 8A illustrates the codon choices made for an amino acid sequence element upon back-translation in accordance with an embodiment of the present invention.

Referring to FIG. 8A, a sequence for which both amino acid 804 and nucleic acid 802 sequences are provided, for example an open reading frame sequence element, will display the codons used for each amino acid below the sequence. The codons for each amino acid are color-coded, with those used at a frequency in the selected organism above the selected threshold shown in one color (806, here dashed boxes), and those that occur at a frequency in the selected organism below the selected threshold in another (808, here solid boxes). This allows a rapid assessment of the suitability of a DNA sequence for expression in the selected host organism.

Figure 8B:
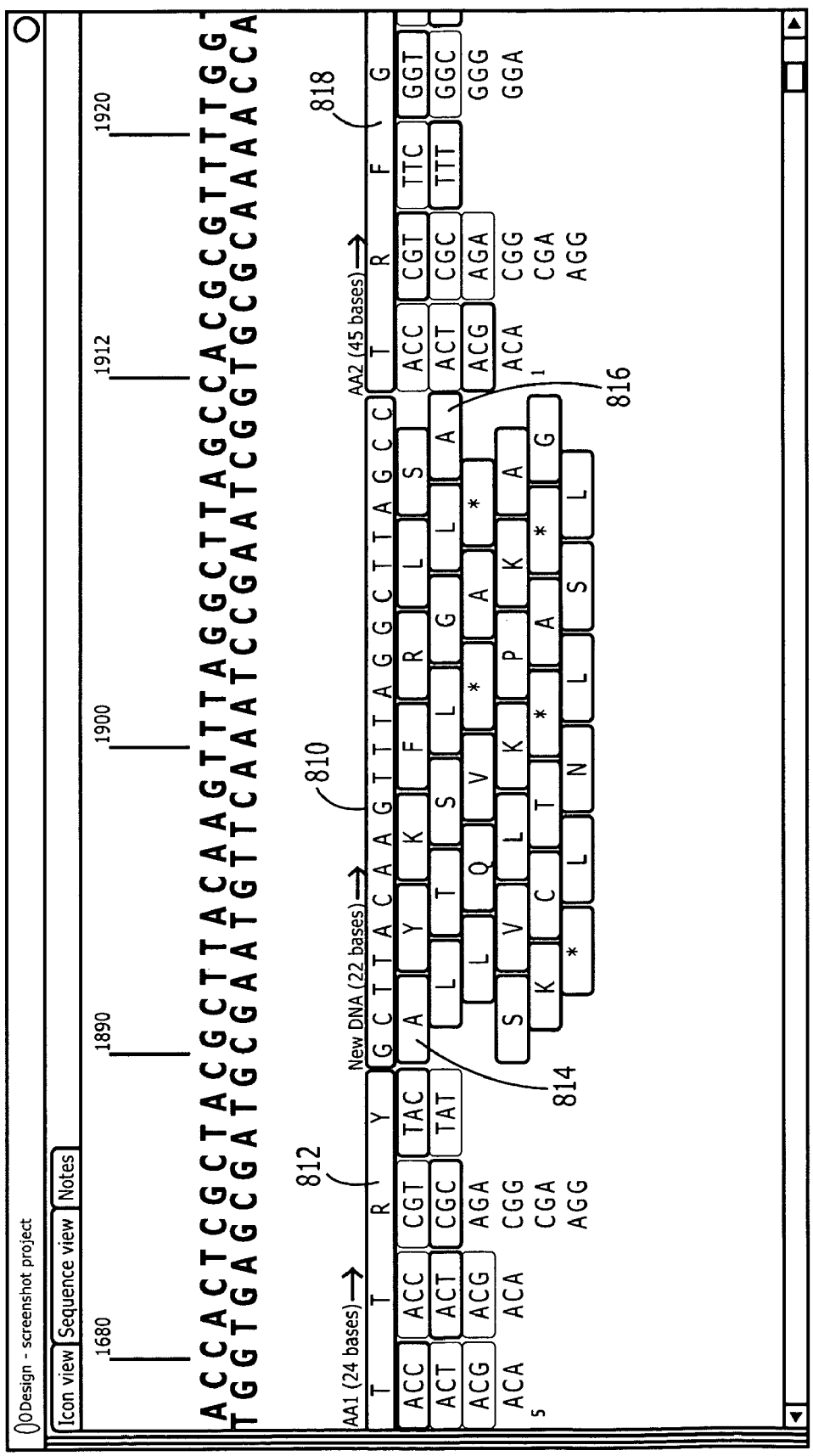
FIG. 8B illustrates the reading frames of an open reading frame element that are in frame with adjacent amino acid elements in accordance with an embodiment of the present invention.

Referring to FIG. 8B, the amino acids encoded by a nucleic acid sequence element 810 are indicated below the first nucleic acid sequence. The amino acid sequences are shown for all six reading frames of the nucleic acid sequence element 810. Reading frames are color coded to show the reading frame 814 that is in the same frame as a preceding amino acid sequence element 812, as well as the reading frame 816 of the amino acid sequence element 816 that is in the same frame with the amino acid sequence element 818 that follows the nucleic acid sequence element.

Figure 9:
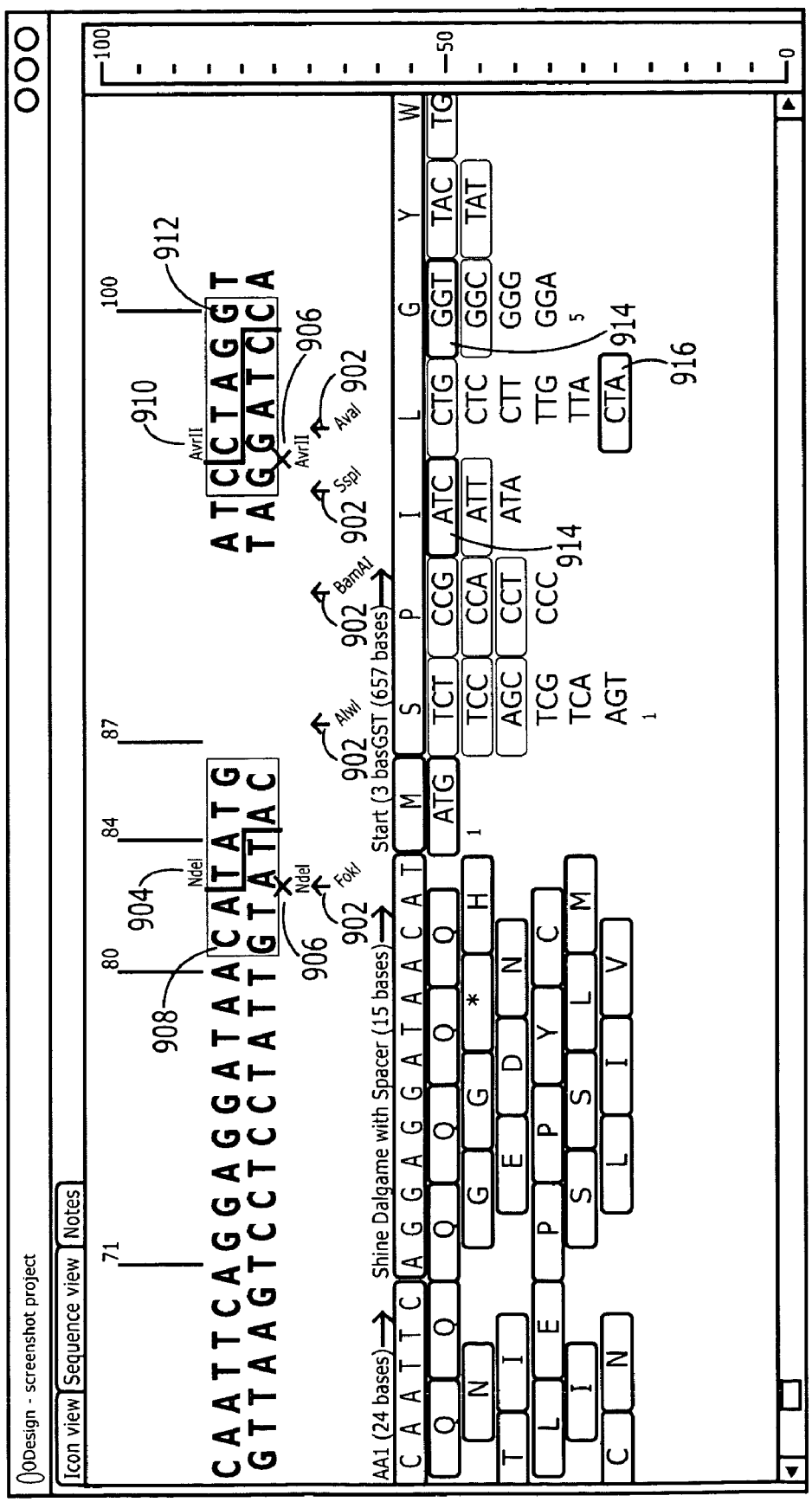
FIG. 9 illustrates the incorporation of restriction sites into a nucleic acid sequence in accordance with an embodiment of the present invention.

Referring to FIG. 9, one or more restriction enzyme recognition sites can be selected from a list (FIG. 7, element 732). By selecting the "show" button 740 (FIG. 7), the locations at which these restriction sites could occur in the amino acid sequence without changing the amino acid sequence are indicated as icons 902. Selection of a particular icon 902 causes the corresponding restriction site to be entered even if it causes a change in the codons used for the corresponding amino acid sequence. Furthermore, when a restriction site is selected by selecting the corresponding icon 902, the recognition sequence (restriction site) is added to the upper sequence panel, which ultimately is the design nucleic acid sequence for the project. In FIG. 9, the restriction site for NdeI and AvrII has been selected. Thus, the restriction site for NdeI (908) and AvrII (912) has been added to the design nucleic acid sequence. Furthermore, the name of these restriction sites has been added at their loci in the design nucleic acid sequence (904/910). The specific point of enzymatic cleavage 906 and the overhangs generated by such cleavage is also indicated in the design nucleic acid sequence. A restriction site can be deselected by deselecting the icon 902 for such a site.

Selection of a restriction recognition site fixes part of the corresponding design nucleic acid sequence. For this reason, the portion of the design nucleic acid sequence that has been fixed will appear in the design nucleic acid sequence above the corresponding amino acid sequence. Below the amino acid sequence, the codons that are needed to incorporate the restriction site are indicated. These codons are indicated in two different ways depending on whether they are above or below the selected threshold 726 (FIG. 7) for the selected codon bias table 730 (FIG. 7). Those codons that are above the selected threshold 726 are shown in a first color 914, and those codons that occur below the selected threshold 726 are shown in a second color 916.

Referring to FIG. 10, more details of the restriction panel 731 of FIG. 7 are provided. Restriction site panel 731 allows selection of one or more restriction sites from a list by name 1002 or recognition sequence 1004. The panel also contains information about the location of cuts made by the enzyme 1006. One or more sites can be avoided in a selected sequence element by selecting the corresponding toggle 1008, or within the entire design nucleic acid sequence by selecting the toggle 1010. Avoided restriction sites will only be eliminated in back-translated regions of the design nucleic acid sequence. Restriction sites present in regions of the design nucleic acid sequence corresponding to nucleic acid sequence elements, or open reading frame sequence elements that have been fixed will not be removed.

Figure 11A:
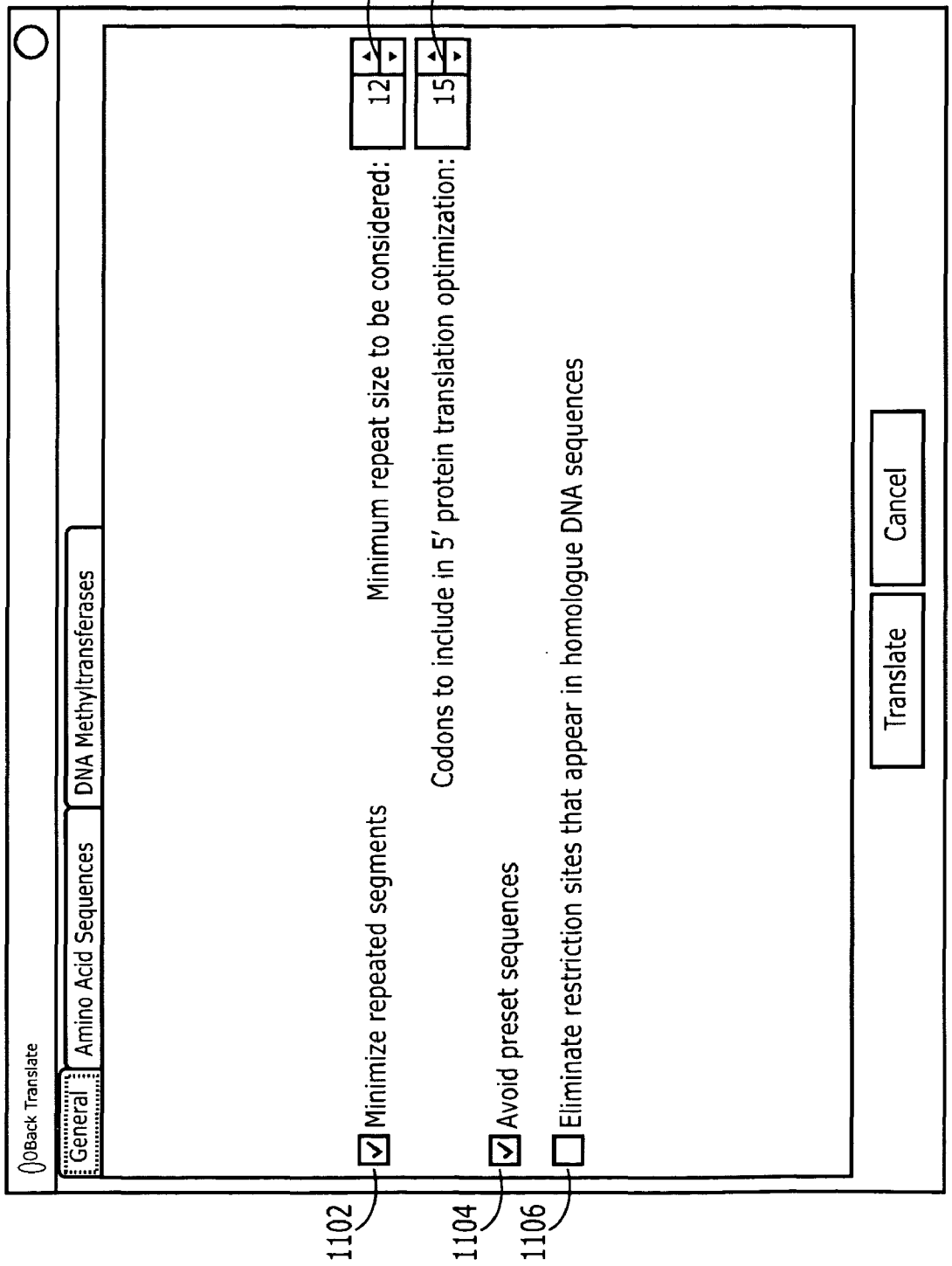
FIG. 11A illustrates a part of the interface for a back-translation module in accordance with an embodiment of the present invention.

Referring to FIG. 11A, the details by which back-translation can be accomplished for amino acid sequence elements and open reading fragment sequence elements that have not been fixed is provided. In some embodiments this back-translation is accomplished using back translation module 82 (FIG. 1). For the case of amino acid sequence elements, back-translation converts amino acids into a corresponding nucleic acid sequence that encodes the amino acids. This corresponding nucleic acid sequence is incorporated into the design nucleic acid sequence. Optional settings for back-translation include minimizing repeat segments 1102, specifying repeat size selection 1108, avoiding pre-set sequences 1104, elimination of restriction sites that appear in homolog nucleic acid sequences 1106, and specifying the number of codons to include in 5N protein translation optimization 1110. Identification and minimization of repeats can be performed using algorithms such as those disclosed in Ukkonen, 1992, "Constructing Suffix Trees On-Line in Linear Time," In *Algorithms, Software, Architecture*, J. v. Leeuwen (ed.), vol# 1 of Information Processing 92, Proc. IFIP 12$^{th}$ World Computer Congress, Madrid, Spain, Elsevier Sci. Publ., pp 484-492; and Ukkonen, 1995, "On-line Construction of Suffix Trees," Algorithmica 14, 249-260, each of which is hereby incorporated by reference in its entirety.

Figure 11B:
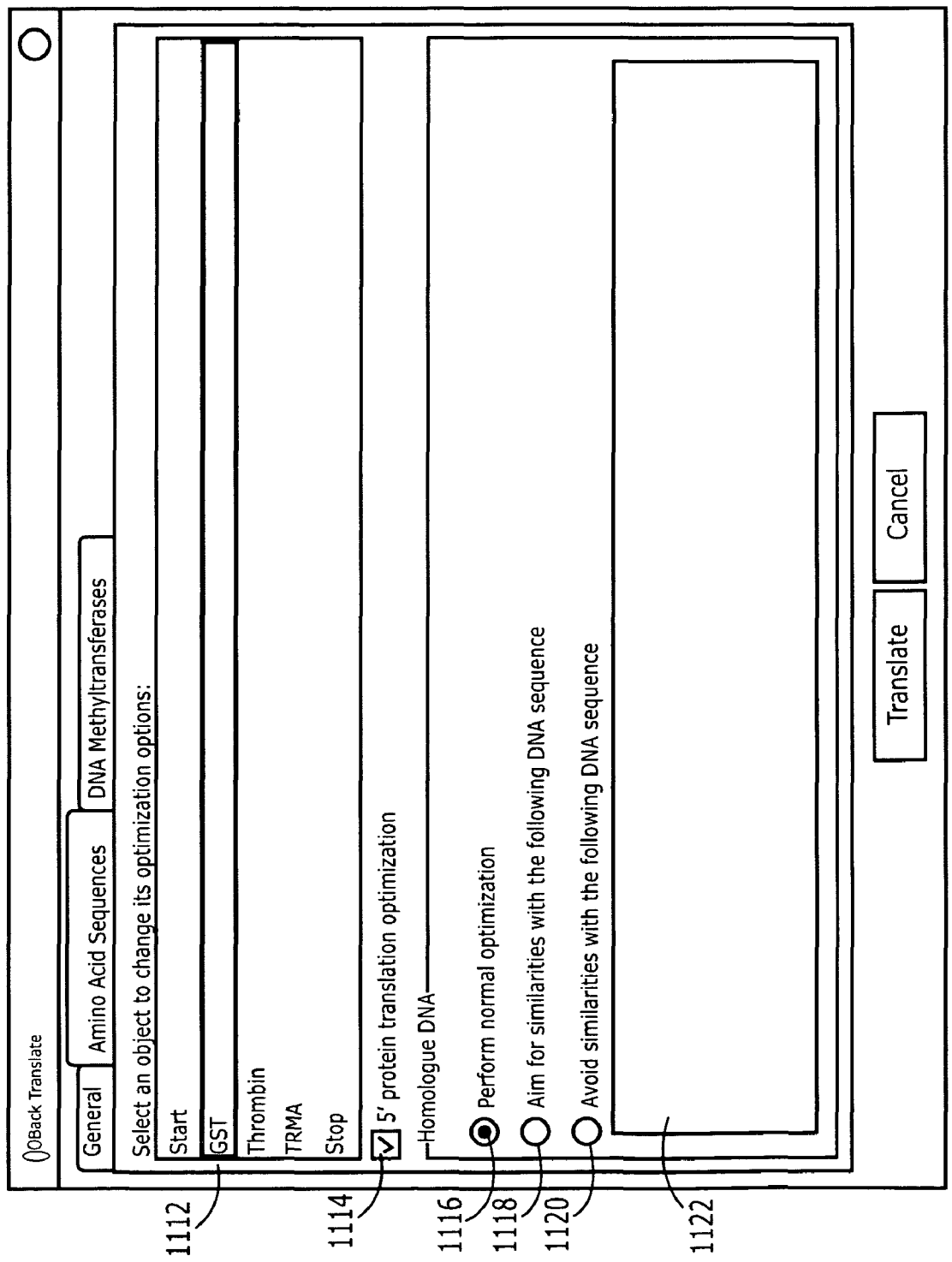
FIG. 11B illustrates a part of the interface for a back-translation module in accordance with an embodiment of the present invention.

Referring to FIG. 11B, each amino acid sequence segment or open reading frame sequence element can also be individually selected 1112 for independent optimization of the beginning of open reading frames for translation initiation 1114. This minimizes secondary structures that could interfere with the initiating ribosome, and allows selection of the length of sequence to be optimized (1110, FIG. 11A).

Each amino acid sequence element or open reading frame sequence element that is not fixed can also be individually selected 1112 and compared with a homologous reference sequence that can be pasted into box 1122. Sequence identity between the selected sequence element 1112 and the entered reference sequence 1122 can be maximized 1118 or minimized 1120, or not taken into account 1116.

In order to minimize or maximize the identity of two sequences, they are first aligned. Alignment algorithms for performing such alignments include, but are not limited to, local alignment algorithms (e.g., Smith Waterman, 1981, "Identification of common molecular subsequences," J Mol Bio. 147:195-7, which is hereby incorporated by reference in its entirety) and global alignment algorithms (e.g., Needleman-Wunsch Algorithm as described in Needleman and Wunsch, 1970, "A general method applicable to the search for similarities in the amino acid sequence of two proteins," 1970, J Mol Biol. 48, 443-53, which is hereby incorporated by reference in its entirety). Once two sequences have been aligned, either using the algorithms described above or other alignment algorithms, a percent identity or percent similarity is computed. Thus, to minimize the identity of the design nucleic acid sequence to a reference sequence, suitable codons (codons above a threshold frequency in the selected codon table) are chosen that decrease the percent identity (or percent similarity) to the reference sequence. To maximize the identity of the design nucleic acid sequence to a reference sequence, suitable codons (codons above a threshold frequency in the selected codon table) are chosen that increase the percent identity (or percent similarity) to the reference sequence. Exemplary metrics that can be used for such purposes include, but are not limited to ungapped identity and gapped identity. Ungapped identity is the number of amino acids (or nucleotides) in an alignment that are identical, divided by the total number of amino acids (or nucleotides) in the alignment. Gapped identity has the same definition with the exception that gaps are considered. Therefore gaps in an alignment will reduce the gapped percent identity.

Referring to FIG. 11C, restriction sites 1126 known to be blocked by overlapping methylation, for example Dam 1128 or Dcm 1130, can be indicated. Option 1124 can be selected to eliminate such restriction sites, if possible, during back-translation. Once all selections have been made, the selected sequences can be backtranslated using the selected codon table 730.

Figure 12:
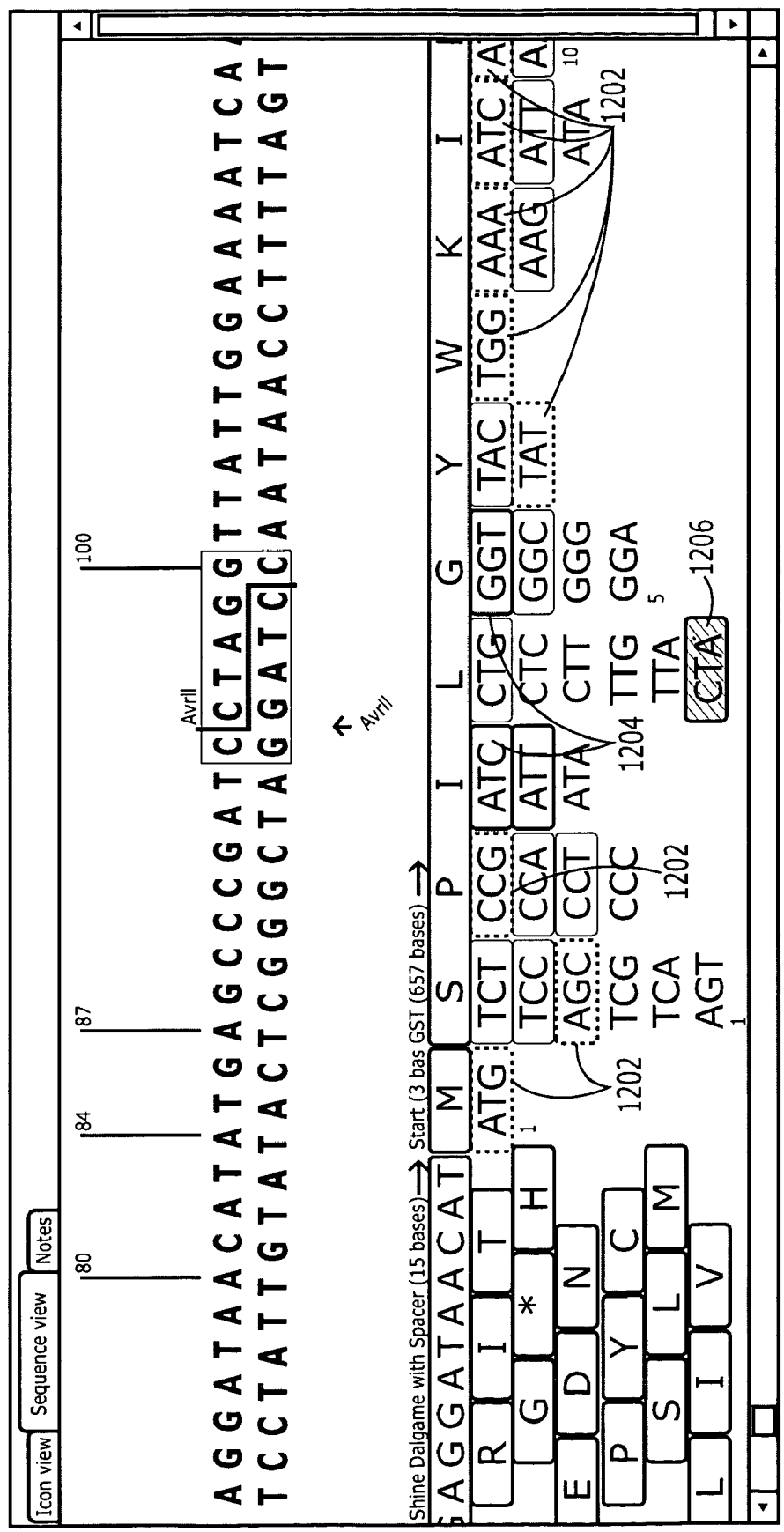
FIG. 12 illustrates a restriction site in a design nucleic acid sequence in accordance with an embodiment of the present invention.

Referring to FIG. 12, after back-translation, codons are differentiated in the sequence view between codons assigned by back-translation 1202 (dashed boxes) and codons selected by the user (1204/1206), for example for inclusion of a restriction site. Codons selected by the user that are above a threshold frequency in the selected codon frequency table are shown in with one attribute (1204, solid boxes) whereas codons that are below the threshold frequency in the selected codon frequency table are shown with another attribute (1206, hashed marks). Suitable attributes that can be used include, but are not limited to, the use of boxes with different characteristics as illustrated in FIG. 12 or the use of different color or shading schemes.

Figure 13:
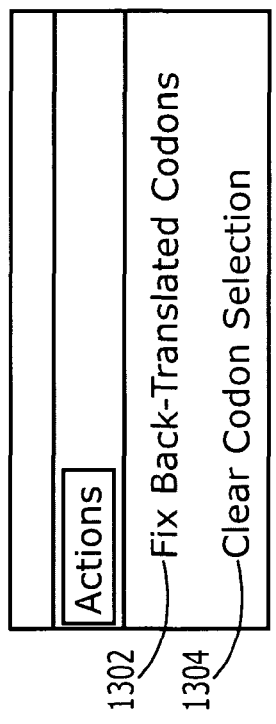
FIG. 13 illustrates actions for clearing a back-translation in accordance with an embodiment of the present invention.

Referring to FIG. 13, after back-translation, codons for one or more sequence elements can be fixed so that they are not altered by subsequent back-translation steps 1302. Alternatively, such codons can be cleared 1304 and, for example, subjected to back-translation using different parameters.

Figure 14A:
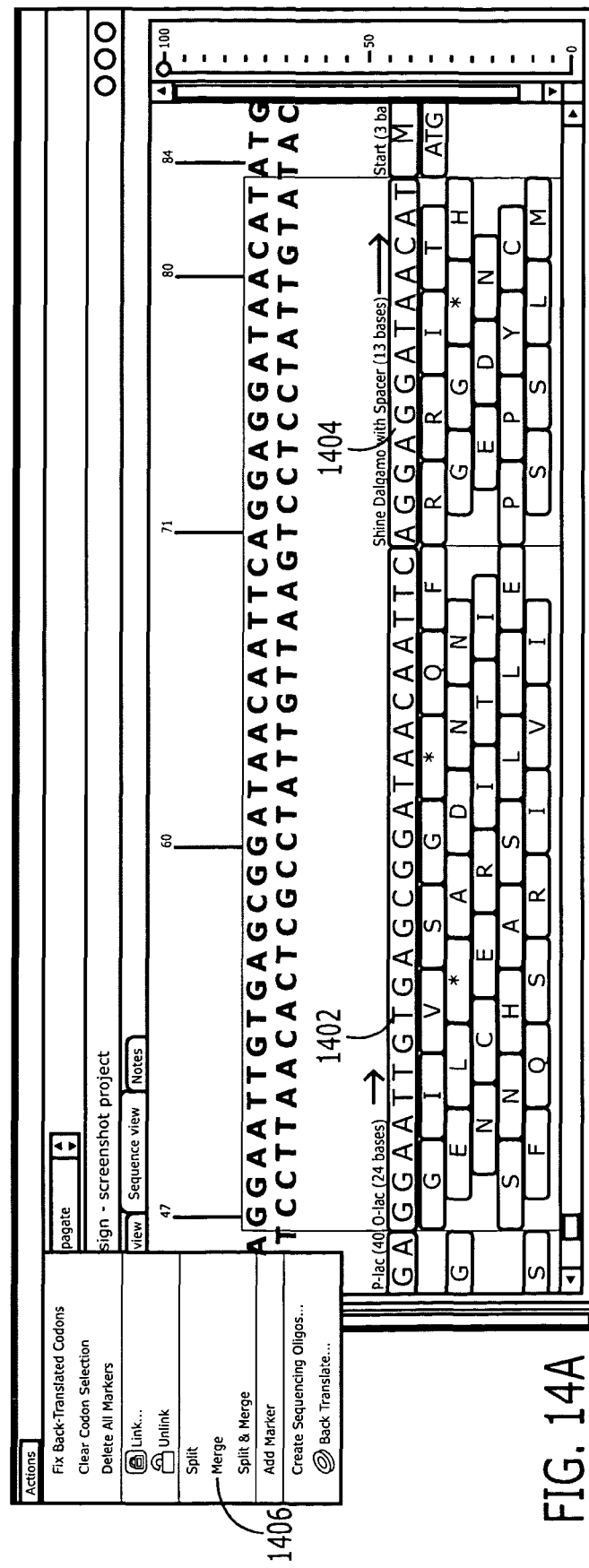
FIG. 14A illustrates two sequences elements in sequence view, prior to a merge element process in accordance with an embodiment of the present invention.
Figure 14B:
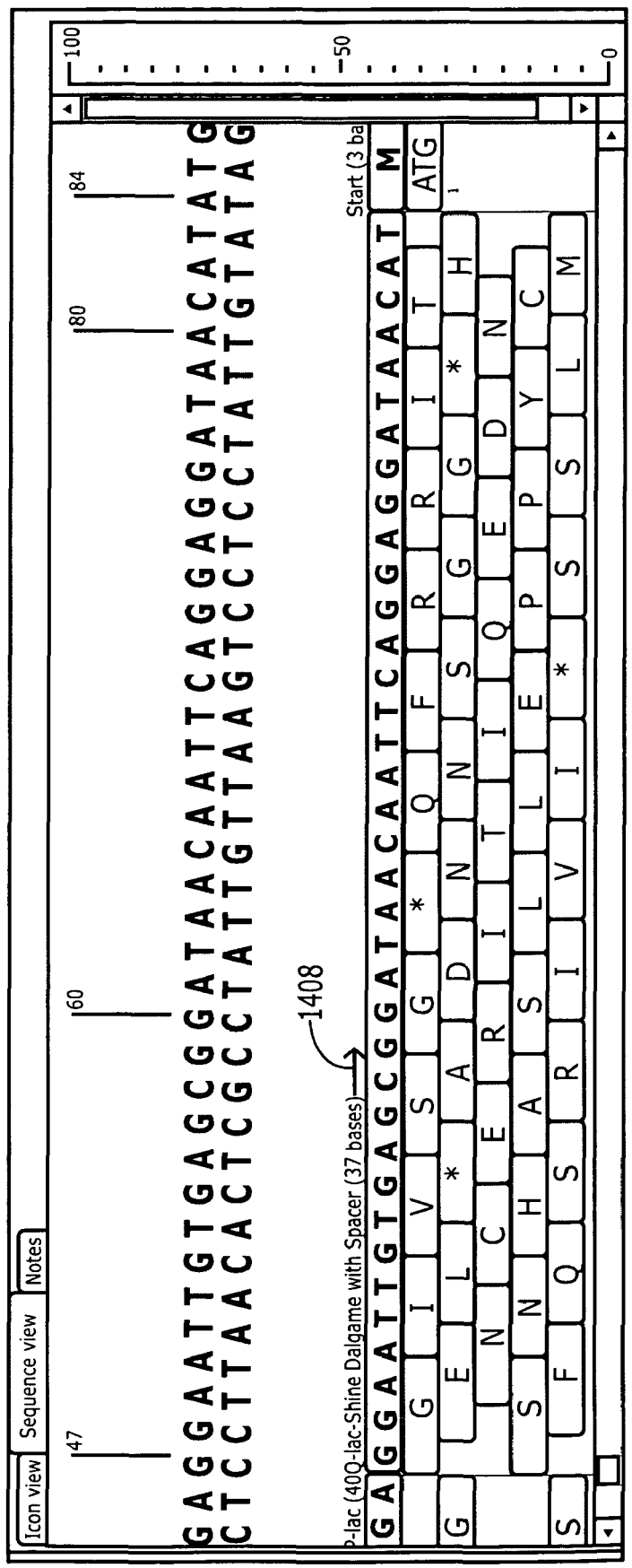
FIG. 14B illustrates a single sequence element upon completion of a merge process in accordance with an embodiment of the present invention.
Figure 14C:
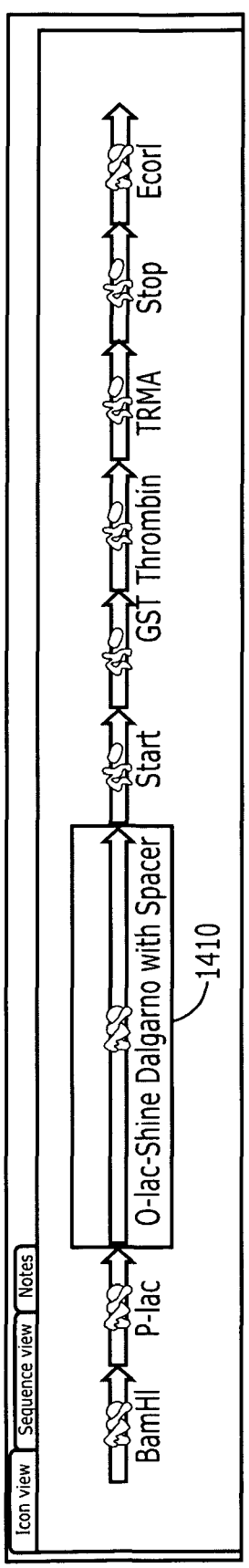
FIG. 14C illustrates a single sequence element resulting from a merge process in icon view in accordance with an embodiment of the present invention.

Referring to FIG. 14A, two or more sequence elements (e.g., 1402 and 1404) can be selected in sequence view. By selecting merge function 1406 (FIG. 14A) of merge/split element module 82 (FIG. 1), the sequence elements are combined into a single sequence element in sequence (1408, FIG. 14B) and icon (1410, FIG. 14C) views. The original sequence elements (1402 and 1404) are discarded in view of the new merged sequence elements. In another words, some embodiments of the present invention provide instructions for merging a first sequence element and a second sequence element in a set of sequence elements thereby forming a single sequence element in the set of sequence elements from the first sequence element and the second sequence element.

Figure 15A:
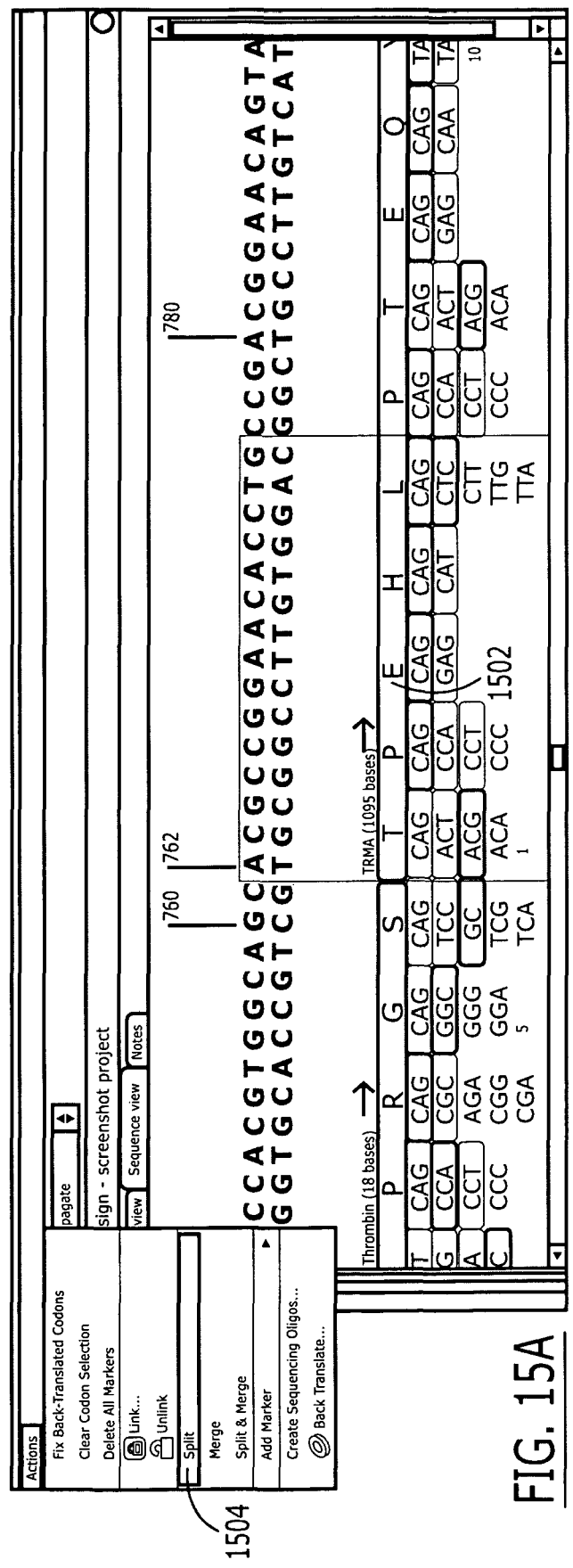
FIG. 15A illustrates a particular sequence element in sequence view, prior to a split element process in accordance with an embodiment of the present invention.
Figure 15B:
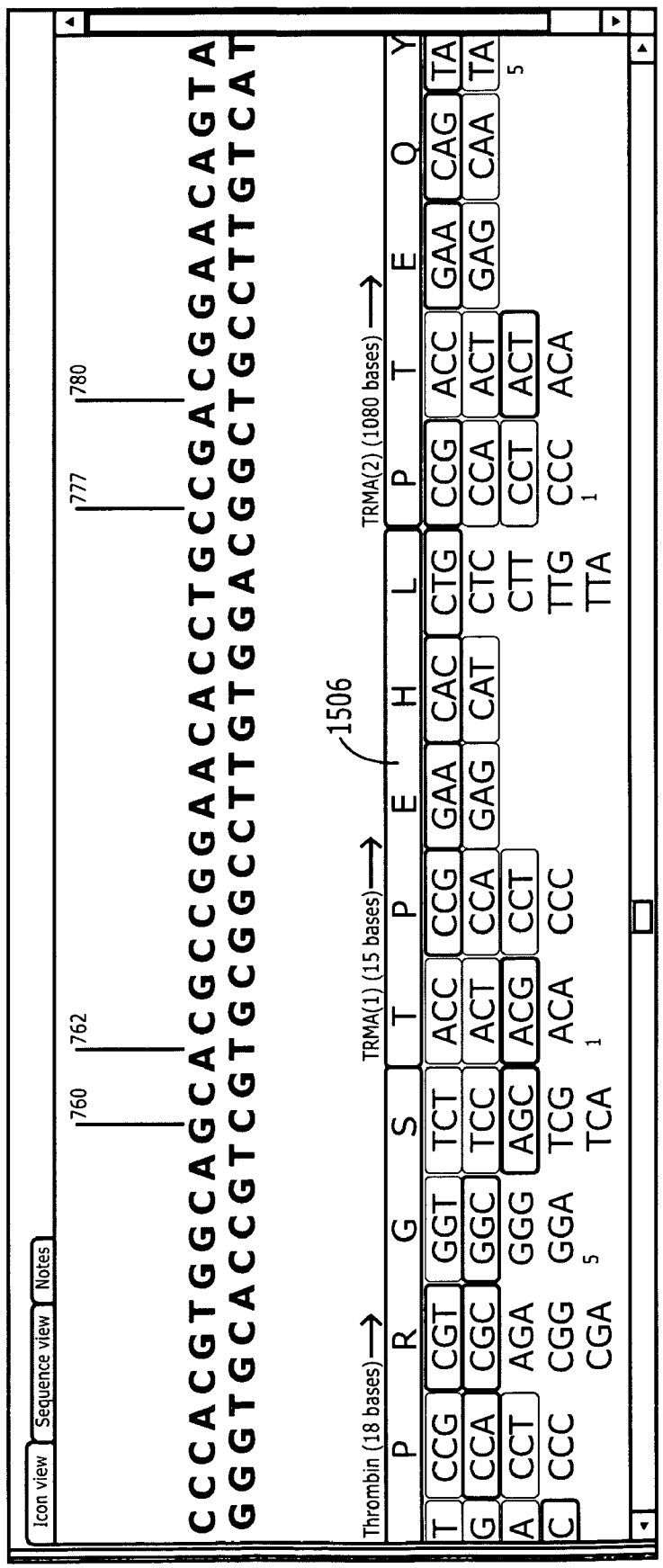
FIG. 15B illustrates the generation of a new sequence element in sequence view upon completion of a split process in accordance with an embodiment of the present invention.
Figure 15C:
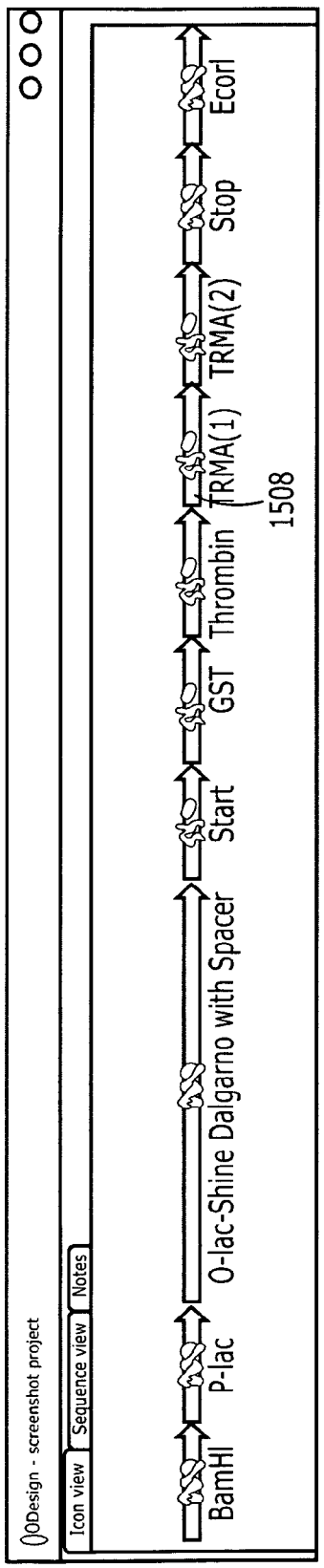
FIG. 15C illustrates the generation of a new sequence element in icon view upon completion of a split process in accordance with an embodiment of the present invention.

Referring to FIG. 15A, a section of a sequence element (1502) can be selected in sequence view. By selecting split function 1504 (FIG. 15A) of merge/split element module 82 (FIG. 1), the selected element is separated into a new sequence element in sequence (1506, FIG. 15B) and icon (1508, FIG. 15C) views. In other words, some embodiments of the present invention provide instructions for selecting a portion of a first sequence element in a set of sequence elements and splitting the portion of the first sequence element into a new second sequence element in the set of sequence elements.

Referring to FIG. 16A, two or more sequence elements that include one or more partial elements (e.g., 1602, 1604) can be selected in sequence view. By selecting split and merge function 1606, the sequence elements are separated from the sequence elements that they were part of and are combined into a single new sequence element in sequence (1608, FIG. 16B) and icon (1610, FIG. 16C) views. In other words, some embodiments of the invention provide (i) instructions for selecting a contiguous sequence where the contiguous sequence is all or a portion of two or more adjacent sequence elements in the linear or near linear arrangement of sequence elements and (ii) instructions for splitting the contiguous sequence into a new sequence element in the set of sequence elements and eliminating the contiguous sequence in the two or more adjacent sequence elements.

Referring to FIG. 17, some embodiments of the present invention provide instructions for saving a set of sequence elements as a first project and instructions for permitting the selection of a project from among a plurality of projects. Each project in the plurality of projects comprises a set of sequence elements. A user can then link a first sequence element in the set of sequence elements in the first project with a corresponding second sequence element in a set of sequence elements in another project in the plurality of projects such that, when changes are made to a nucleic acid sequence associated with the first sequence element, the same changes are made to a nucleic acid sequence associated with the second sequence element. In some embodiments, instructions for removing the link between the first sequence element and the second sequence element are provided. Some embodiments of the present invention provide instructions for locking the nucleic acid sequence associated with the first sequence element and the nucleic acid sequence associated with the second sequence element so that no change is allowed to either nucleic acid sequence.

To illustrate, again referring to FIG. 17, sequence elements can be linked across projects. When this is done, a change made to a sequence element in one project is propagated through all linked sequence elements in other open projects. Referring to FIG. 17A, a sequence element 1704 in a first project is selected and link action 1702 is chosen. Referring to FIG. 17B, such action creates a link dialog box 1750 that specifies the chosen sequence element 1704 from the first project 1708. This sequence element can then be linked to another element 1706 selected from another open project 1712. Any sequence element 1706 in any open project 1712 can be chosen. Once an element has been chosen a link can be created 1716 or the action cancelled 1718. Once sequence elements are linked, this is indicated in icon view with a graphic icon 1720 near each of the linked sequence elements. Referring to FIG. 17C, the user can select options for linked sequence elements. One option is to propagate any change made in the sequence of one linked sequence element to all the other linked sequence elements (1722). Another option is to disallow any changes to the sequence of linked sequence elements (1724). Still another option is to unlink linked sequence elements (1726).

Referring to FIG. 18, a directional property of a sequence element can be reversed by selecting the element (e.g., 1802) and then selecting reverse toggle 1804. The arrow representing direction is then reversed in the icon view (1806). In some embodiments, the direction property is a translation direction or a transcription direction. In the sequence view, a reversed amino acid element is shown with the order of amino acids reversed (compare 1802 of FIG. 18A with 1810 of FIG. 18C). However, the codons for each amino acid are shown as the actual codons in the forward direction (left to right, see, for example, 1812) for ease of manipulation. The DNA sequence of each codon is reversed to show the actual DNA sequence (on the reverse strand) (see, for example, 1808 of FIG. 18C) in the design nucleic acid sequence.

Some embodiments of the present invention provide a $T_m$ calculation module 54 (FIG. 1) that comprises (i) instructions for selecting a start point and an end point in the design nucleic acid sequence, thereby defining an oligonucleotide (ii) instructions for computing a $T_m$ of the oligonucleotide; and (iii) instructions for displaying the $T_m$ of the oligonucleotide. In some embodiments, the $T_m$ is calculated using an algorithm such as that disclosed in Le Novère, 2001, "MELTING, computing the melting temperature of nucleic acid duplex, Bioinformatics Applications Note 17, 1226-1227, which is hereby incorporated by reference. In some embodiments, the instructions for displaying the $T_m$ of the oligonucleotide comprise instructions for displaying the $T_m$ and a numeric representation of the start point and the end point. In some embodiments, the $T_m$ calculation module further comprises instructions for moving the start point and/or the end point and, for each new start point and/or end point specified by the user, repeating the instructions for computing and the instructions for displaying. FIG. 19 illustrates. Referring to FIG. 19A, a sequence region 1902 can be selected in the design nucleic acid and a Tm calculator marker 1906 added using the add marker 1904 drop down menu selection. Referring to FIG. 19B, Tm calculator marker 1906 allows for modification of the start 1908 and end 1910 positions of the marker in the design nucleic acid. The marker can then be created, option 1912, or cancelled, option 1914. Referring to FIG. 19C, the ends 1908 and 1910 of FIG. 19B define an oligonucleotide within the design nucleic acid. In FIG. 19C, a graphic icon is positioned above the design nucleic acid in order to represent the oligonucleotide. The ends 1916 of the graphic representation of the oligonucleotide are marked and represent the start and stop positions of the oligonucleotide. The start and stop positions of the oligonucleotide in the design nucleic acid are provided as label 1918. Also, the Tm of the oligonucleotide is provided as label 1920. Either end 1916 can be moved using mouse and/or keyboard operations, and the graphic representation of the oligonucleotide, including ends 1916, label 1918, and Tm 1920 are automatically updated as the ends are adjusted along the length of the design nucleic acid.

Some embodiments of the present invention provide an oligonucleotide marker module 56 (FIG. 1) that comprises (i) instructions for selecting a start point and an end point in the design nucleic acid sequence, thereby defining an oligonucleotide, (ii) instructions for defining a 5' to 3' direction of the oligonucleotide, and (iii) instructions for displaying the oligonucleotide as a graphic above or below the design nucleic acid sequence. FIG. 20 illustrates. A sequence region 2002 within the design nucleic acid can be selected and an oligo marker 2006 added through the add marker menu 2004 option. Referring to FIG. 20B, modification of the start 2008 and end 2010 positions of the marker in the design nucleic acid is permitted. A corresponding oligonucleotide can be generated in the forward 2012 or reverse 2014 directions. A sequence of the selected oligonucleotide can be generated using the create switch 2016. Alternatively, the operation can be cancelled using the cancel toggle 2018. Referring to FIG. 20C, once an oligonucleotide is created using create switch 2016, the oligonucleotide is represented as a graphic 2024 above the design nucleic acid sequence. The graphic for the oligonucleotide has a 3' end 2020 and a 5' end 2022, both of which can be moved by mouse and/or keyboard operations. The marker also carries information describing its ends 2024.

Advantageously, the systems and methods of the present invention can be used to order a design nucleic acid sequence over a network (e.g., using order module 58 of interface 44).

In other words, some embodiments of the present invention provide instructions for communicating a sequence of the design nucleic acid (or any of the oligonucleotides associated with a project) across a network as part of an order for such a sequence. This network can be, for example, the Internet. In some embodiments such orders are sent in encrypted form in order to ensure privacy of the order.

Referring to FIG. 21, in some embodiments, reports can be generated from report menu 2102. These can be a summary of information from the project (2104), a report describing the oligonucleotides in the project (2106), or a report visualizing the repeats present in the sequence (2108). Referring to FIG. 22, a summary report can be generated to provide the complete DNA sequence of the design nucleic acid sequence for a project (2202), the DNA sequence of each sequence element of a project (2204), general notes for each sequence element (2206), a codon translation map for each sequence element (2208), a restriction site summary for the design nucleic acid sequence of a project (2210), the codon use frequencies in the design nucleic acid sequence (2212), the GC content of the design nucleic acid sequence (2214), and a list of repeats present in the design nucleic acid sequence (2216). Once the desired options have been selected, a report can be generated (2218) or cancelled (2220). A sample report is shown below in the Example section below. Also, FIG. 23 illustrates an oligonucleotide report for a project in accordance with an embodiment of the present invention. The oligonucleotide report displays the sequences of all oligos present in the project (2310). For each oligonucleotide, the start (2302) and end (2304) positions are displayed, together with the orientation, either forward (2306) or reverse (2308), relative to the direction of the sequence.

6. EXAMPLES

What follows is an exemplary report that was generated using the systems and methods of the present invention.

6.1 Complete Design Nucleic Acid Sequence

```
GGATCCGGCTTTACACTTTATGCTTCCGGCTCGTATGTTGTGTGGAGGAATTGTGAGCGGATAACAATT   (SEQ ID NO: 1)
CAGGAGGATAACATATGAGCCCGATCCTAGGTTATTGGAAAATCAAAGGCCTGGTTCAGCCGACGCGTC
TGCTGCTGGAATACCTCGAAGAAAAATACGAAGAACACCTGTACGAACGCGATGAAGGTGATAAATGGC
GCAACAAAAAGTTTGAACTGGGTCTGGAATTTCCGAACCTGCCGTACTATATTGATGGTGATGTAAAAC
TGACCCAATCCATGGCCATCATCCGTTACATTGCCGATAAACATAACATGCTGGGTGGTTGTCCTAAAG
AACGTGCCGAAATTAGCATGCTGGAGGGTGCAGTCCTGGATATCCGTTATGGTGTCAGCCGCATTGCTT
ACTCCAAAGACTTCGAAACCCTGAAGGTCGATTTCCTGTCCAAACTGCCGGAAATGCTGAAAATGTTTG
AGGACCGTCTGTGCCACAAAACGTACCTGAATGGCGACCACGTAACTCATCCGGACTTCATGCTGTATG
ACGCGCTGGACGTAGTTCTGTACATGGACCCGATGTGCCTGGACGCATTCCCGAAACTGGTGTGTTTCA
AAAAGCGTATTGAAGCCATCCCGCAGATCGATAAATACCTGAAATCCAGCAAATACATTGCATGGCCGC
TGCAGGGCTGGCAGGCAACCTTCGGCGGTGGCGATCATCCGCCGAAAAGCGACCTGGTCCCACGTGGCA
GCACGCCGGAACACCTGCCGACGGAACAGTACGAGGCGCAGCTGGCTGAAAAAGTTGTACGTCTGCAAT
CTATGATGGCCCCTTTTTCTGACCTGGTACCGGAAGTCTTCCGTTCTCCGGTGTCCCACTATCGTATGC
GTGCAGAATTCCGTATCTGGCACGACGGTGACGACCTGTACCACATTATCTTCGATCAGCAGACGAAAT
CTCGTATCCGCGTTGACTCTTTCCCAGCTGCGAGCGAACTGATCAACCAGCTGATGACTGCAATGATCG
CAGGTGTACGCAACAACCCAGTGCTGCGTCACAAGCTGTTCCAAATTGATTATCTGACTACTCTGAGCA
```

-continued

```
ACCAGGCTGTGGTATCTCTGCTGTACCACAAGAAACTGGACGACGAATGGCGTCAGGAAGCGGAAGCAC

TGCGTGACGCACTGCGCGCACAGAACCTGAACGTGCACCTGATTGGCCGTGCTACGAAAACCAAAATCG

AACTGGATCAGGATTATATCGACGAACGTCTGCCGGTTGCAGGCAAAGAAATGATCTACCGTCAGGTGG

AGAATTCTTTCACCCAGCCGAACGCAGCAATGAACATCCAGATGCTGGAATGGGCGCTGGACGTTACCA

AAGGTTCTAAAGGCGACCTGCTGGAACTGTACTGCGGCAACGGTAACTTTAGCCTGGCTCTGGCACGTA

ACTTCGACCGCGTTCTGGCCACCGAAATCGCAAAGCCTTCCGTTGCGGCAGCCCAATATAACATTGCGG

CAAACCACATCGATAACGTGCAGATCATTCGCATGGCGGCAGAAGAATTCACCCAGGCGATGAACGGCG

TGCGTGAATTTAACCGTCTGCAGGGCATCGATCTGAAATCCTACCAGTGCGAGACTATTTTCGTTGATC

CGCCGCGTTCCGGTCTGGACTCCGAAACCGAAAAGATGGTTCAGGCGTACCCTCGTATTCTGTATATCA

GCTGCAACCCTGAAACTCTGTGCAAAAACCTGGAAACCCTGAGCCAAACCCATAAAGTCGAGCGTCTGG

CTCTGTTTGATCAGTTCCCGTACACTCACCATATGGAATGTGGTGTACTGCTGACCGCGAAGTAAGAAT

TC
```

6.2 DNA Sequence of Each Sequence Element

```
>BamHI
GGATCC

>P-lac
GGCTTTACACTTTATGCTTCCGGCTCGTATGTTGTGTGGA                       (SEQ ID NO: 2)

>O-lac-Shine Dalgarno with Spacer
GGAATTGTGAGCGGATAACAATTCAGGAGGATAACAT                          (SEQ ID NO: 3)

>Start
ATG

>GST (1)
AGCCCGATCCTAGGTTATTGGAAAATCAAAGGCCTGGTTCAGCCGACGCGTCTGCTGCTGGAATACCTG  (SEQ ID NO: 4)

GAAGAAAAATACGAAGAACACCTGTACGAACGCGATGAAGGTGATAAATGGCGCAACAAAAAGTTTGAA

CTGGGTCTGGAATTTCCGAACCTGCCGTACTATATTGATGGTGATGTAAAACTGACCCAATCCATGGCC

ATCATCCGTTACATTGCCGATAAACATAACATGCTGGGTGGTTGTCCTAAAGAACGTGCCGAAATTAGC

ATGCTGGAGGGTGCAGTCCTGGATATCCGTTATGGTGTCAGCCGCATTGCTTACTCCAAAGACTTCGAA

ACCCTGAAGGTCGATTTCCTGTCCAAACTGCCGGAAATGCTGAAAATGTTTGAGGACCGTCTGTGCCAC

AAAACGTACCTGAATGGCGACCACGTAACTCATCCGGACTTCATGCTGTATGACGCGCTGGACGTAGTT

CTGTACATGGACCCGATGTGCCTGGACGCATTCCCGAAACTGGTGTGTTTCAAAAAGCGTATTGAAGCC

ATCCCGCAGATCGATAAATACCTGAAATCCAGCAAATACATTGCATGGCCGCTGCAGGGCTGGCAGGCA

ACCTTCGGCGGTGGCGATCAT

>GST (2)-Thrombin (1)
CCGCCGAAAAGCGACCTGGTCCCA                                        (SEQ ID NO: 5)

>Thrombin (2)
CGTGGCAGC

>TRMA (1)
ACGCCGGAACACCTG                                                 (SEQ ID NO: 6)

>TRMA (2)
CCGACGGAACAGTACGAGGCGCAGCTGGCTGAAAAAGTTGTACGTCTGCAATCTATGATGGCCCCTTTT  (SEQ ID NO: 7)

TCTGACCTGGTACCGGAAGTCTTCCGTTCTCCGGTGTCCCACTATCGTATGCGTGCAGAATTCCGTATC

TGGCACGACGGTGACGACCTGTACCACATTATCTTCGATCAGCAGACGAAATCTCGTATCCGCGTTGAC
```

```
-continued
TCTTTCCCAGCTGCGAGCGAACTGATCAACCAGCTGATGACTGCAATGATCGCAGGTGTACGCAACAAC

CCAGTGCTGCGTCACAAGCTGTTCCAAATTGATTATCTGACTACTCTGAGCAACCAGGCTGTGGTATCT

CTGCTGTACCACAAGAAACTGGACGACGAATGGCGTCAGGAAGCGGAAGCACTGCGTGACGCACTGCGC

GCACAGAACCTGAACGTGCACCTGATTGGCCGTGCTACGAAAACCAAAATCGAACTGGATCAGGATTAT

ATCGACGAACGTCTGCCGGTTGCAGGCAAAGAAATGATCTACCGTCAGGTGGAGAATTCTTTCACCCAG

CCGAACGCAGCAATGAACATCCAGATGCTGGAATGGGCGCTGGACGTTACCAAAGGTTCTAAAGGCGAC

CTGCTGGAACTGTACTGCGGCAACGGTAACTTTAGCCTGGCTCTGGCACGTAACTTCGACCGCGTTCTG

GCCACCGAAATCGCAAAGCCTTCCGTTGCGGCAGCCCAATATAACATTGCGGCAAACCACATCGATAAC

GTGCAGATCATTCGCATGGCGGCAGAAGAATTCACCCAGGCGATGAACGGCGTGCGTGAATTTAACCGT

CTGCAGGGCATCGATCTGAAATCCTACCAGTGCGAGACTATTTTCGTTGATCCGCCGCGTTCCGCTCTG

GACTCCGAAACCGAAAAGATGGTTCAGGCGTACCCTCGTATTCTGTATATCAGCTGCAACCCTGAAACT

CTGTGCAAAAACCTGGAAACCCTGAGCCAAACCCATAAAGTCGAGCGTCTGGCTCTGTTTGATCAGTTC

CCGTACACTCACCATATGGAATGTGGTGTACTGCTGACCGCGAAG

>Stop
TAA

>EcorI
GAATTC
```

6.3 General Notes for Each Sequence Element

Notes for BamHI
null

Notes for P-lac
Transcriptional promoter from the *E coli* lac operon

Notes for O-lac-Shine Dalgarno with Spacer
Transcription operator from the *E coli* lac operon-Consensus ribosome binding site plus 7 base spacer that places an NdeI site at the initiation AUG Notes for Start
Start Notes for GST(1)
Glutathione S-transferase Notes for GST(2)-Thrombin(1)
Glutathione S-transferase-Cleaves between the arginine and glycine Notes for Thrombin(2)
Cleaves between the arginine and glycine Notes for TRMA(1)
null Notes for TRMA(2)
null Notes for Stop
STOP Notes for EcorI
null

6.4 Translation Map for Each Sequence Element

```
Start
   1 ATG

1 M

GST (1)
   1 AGCCCGATCCTAGGTTATTGGAAAATCAAAGGCCTGGTTCAGCCGACGCGTCTGCTGCTG

1 S  P  I  L  G  Y  W  K  I  K  G  L  V  Q  P  T  R  L  L  L

61 GAATACCTGGAAGAAAAATACGAAGAACACCTGTACGAACGCGATGAAGGTGATAAATGG

21 E  Y  L  E  E  K  Y  E  E  H  L  Y  E  R  D  E  G  D  K  W

121 CGCAACAAAAAGTTTGAACTGGGTCTGGAATTTCCGAACCTGCCGTACTATATTGATGGT

41 R  N  K  K  F  E  L  G  L  E  F  P  N  L  P  Y  Y  I  D  G
```

```
-continued
181 GATGTAAAACTGACCCAATCCATGGCCATCATCCGTTACATTGCCGATAAACATAACATG

61  D   V   K   L   T   Q   S   M   A   I   I   R   Y   I   A   D   K   H   N   M

241 CTGGGTGGTTGTCCTAAAGAACGTGCCGAAATTAGCATGCTGGAGGGTGCAGTCCTGGAT

81  L   G   G   C   P   K   E   R   A   E   I   S   M   L   E   G   A   V   L   D

301 ATCCGTTATGGTGTCAGCCGCATTGCTTACTCCAAAGACTTCGAAACCCTGAAGGTCGAT

101  I   R   Y   G   V   S   R   I   A   Y   S   K   D   F   E   T   L   K   V   D

361 TTCCTGTCCAAACTGCCGGAAATCCTGAAAATGTTTGAGGACCGTCTGTGCCACAAAACG

121  F   L   S   K   L   P   E   M   L   K   M   F   E   D   R   L   C   H   K   T

421 TACCTGAATGCCGACCACGTAACTCATCCGGACTTCATGCTGTATGACGCGCTGGACGTA

141  Y   L   N   G   D   H   V   T   H   P   D   F   M   L   Y   D   A   L   D   V

481 GTTCTGTACATGGACCCGATGTGCCTGGACGCATTCCCGAAACTGGTGTGTTTCAAAAAG

161  V   L   Y   M   D   P   M   C   L   D   A   F   P   K   L   V   C   F   K   K

541 CGTATTGAAGCCATCCCGCAGATCGATAAATACCTCAAATCCAGCAAATACATTGCATGG

181  R   I   E   A   I   P   Q   I   D   K   Y   L   K   S   S   K   Y   I   A   W

601 CCGCTGCAGGGCTGGCAGGCAACCTTCGGCGGTGGCGATCAT                 (SEQ ID NO: 1)

201  P   L   Q   G   W   Q   A   T   F   G   G   G   D   H              (SEQ ID NO: 8)
GST (2) Thrombin (1)
   1 CCGCCGAAAAGCGACCTCGTCCCA                                  (SEQ ID NO: 5)

1  P   P   K   S   D   L   V   P                                   (SEQ ID NO: 9)
Thrombin (2)
   1 CGTGGCAGC 1  R   G   S
TRMA (1)
   1 ACGCCGGAACACCTG                                           (SEQ ID NO: 6)

1  T   P   E   H   L                                              (SEQ ID NO: 10)
TRMA (2)
   1 CCGACGGAACAGTACGAGGCGCAGCTGGCTGAAAAAGTTGTACGTCTGCAATCTATGATG

1  P   T   E   Q   Y   E   A   Q   L   A   E   K   V   V   R   L   Q   S   M   M

61 GCCCCTTTTTCTGACCTGGTACCGGAAGTCTTCCGTTCTCCGGTGTCCCACTATCGTATG

21  A   P   F   S   D   L   V   P   E   V   F   R   S   P   V   S   H   Y   R   M

121 CGTGCAGAATTCCGTATCTGGCACGACGGTGACGACCTGTACCACATTATCTTCGATCAG

41  R   A   E   F   R   I   W   H   D   G   D   D   L   Y   H   I   I   F   D   Q

181 CAGACGAAATCTCGTATCCGCGTTGACTCTTTCCCAGCTGCGAGCGAACTGATCAACCAG

61  Q   T   K   S   R   I   R   V   D   S   F   P   A   A   S   E   L   I   N   Q

241 CTGATGACTGCAATGATCGCAGGTGTACGCAACAACCCAGTGCTGCGTCACAAGCTGTTC

81  L   M   T   A   M   I   A   G   V   R   N   N   P   V   L   R   H   K   L   F

301 CAAATTGATTATCTGACTACTCTGAGCAACCAGGCTGTGGTATCTCTGCTGTACCACAAG

101  Q   I   D   Y   L   T   T   L   S   N   Q   A   V   V   S   L   L   Y   H   K

361 AAACTGGACGACGAATGGCGTCAGGAAGCGGAAGCACTGCGTGACGCACTGCGCGCACAG

121  K   L   D   D   E   W   R   Q   E   A   E   A   L   R   D   A   L   R   A   Q

421 AACCTGAACGTGCACCTGATTGGCCGTGCTACGAAAACCAAAATCGAACTGGATCAGGAT

141  N   L   N   V   H   L   I   G   R   A   T   K   T   K   I   E   L   D   Q   D
```

-continued

```
481 TATATCGACGAACGTCTGCCGGTTGCAGGCAAAGAAATGATCTACCGTCAGGTGGAGAAT
161  Y  I  D  E  R  L  P  V  A  G  K  E  M  I  Y  R  Q  V  E  N

541 TCTTTCACCCAGCCGAACGCAGCAATGAACATCCAGATGCTGGAATGGGCGCTGGACGTT
181  S  F  T  Q  P  N  A  A  M  N  I  Q  M  L  E  W  A  L  D  V

601 ACCAAAGGTTCTAAAGGCGACCTGCTGGAACTGTACTGCGGCAACGGTAACTTTAGCCTG
201  T  K  G  S  K  G  D  L  L  E  L  Y  C  G  N  G  N  F  S  L

661 GCTCTGGCACGTAACTTCGACCGCGTTCTGGCCACCGAAATCGCAAAGCCTTCCGTTGCG
221  A  L  A  R  N  F  D  R  V  L  A  T  E  I  A  K  P  S  V  A

721 GCAGCCCAATATAACATTGCGGCAAACCACATCGATAACGTGCAGATCATTCGCATGGCG
241  A  A  Q  Y  N  I  A  A  N  H  I  D  N  V  Q  I  I  R  M  A

781 GCAGAAGAATTCACCCAGGCGATGAACGGCGTGCGTGAATTTAACCGTCTGCAGGGCATC
261  A  E  E  F  T  Q  A  M  N  G  V  R  E  F  N  R  L  Q  G  I

841 GATCTGAAATCCTACCAGTGCGAGACTATTTTCGTTGATCCGCCGCGTTCCGGTCTGGAC
281  D  L  K  S  Y  Q  C  E  T  I  F  V  D  P  P  R  S  G  L  D

901 TCCGAAACCGAAAAGATGGTTCAGGCGTACCCTCGTATTCTGTATATCAGCTGCAACCCT
301  S  E  T  E  K  M  V  Q  A  Y  P  R  I  L  Y  I  S  C  N  P

961 GAAACTCTGTGCAAAAACCTGGAAACCCTGAGCCAAACCCATAAAGTCGAGCGTCTGGCT
321  E  T  L  C  K  N  L  E  T  L  S  Q  T  H  K  V  E  R  L  A

1021 CTGTTTGATCAGTTCCCGTACACTCACCATATGGAATGTGGTGTACTGCTGACCGCGAAG
341   L  F  D  Q  F  P  Y  T  H  H  M  E  C  G  V  L  L  T  A  K (SEQ ID NO: 7)

(SEQ ID NO: 11)

Stop
   1 TAA

1 *
```

6.5 Restriction Sites for Design Nucleic Acid Sequence

| Name  | Sequence  | Locations |
|-------|-----------|-----------|
| AatI  | AGGCCT    | 115 |
| AccI  | GTMKAC    | none |
| AflII | CTTAAG    | none |
| AgeI  | ACCGGT    | none |
| AlwI  | GGATC     | 0, 1246, 1(c), 91(c), 1652(c) |
| AlwNI | CAGNNNCTG | 1193, 1349 |
| ApaI  | GGGCCC    | none |
| ApaLI | GTGCAC    | 1205 |
| AscI  | GGCGCGCC  | none |
| AseI  | ATTAAT    | none |
| AvaI  | CYCGRG    | none |
| AvaII | GGWCC     | 484, 577, 745 |
| AvrII | CCTAGG    | 94 |
| BamHI | GGATCC    | 0 |
| BbsI  | GAAGAC    | 863(c) |
| BbvI  | GCAGC     | 756, 796, 1334, 1496, 139(c), 688(c), 992(c), 1057(c), 1725(c) |
| BclI  | TGATCA    | 1005, 1801 |
| BglII | AGATCT    | none |
| BlpI  | GCTNAGC   | none |
| BsaI  | GGTCTC    | none |
| BsmAI | GTCTC     | 1637(c) |

-continued

| Name | Sequence | Locations |
|---|---|---|
| BsmBI | CGTCTC | none |
| BstEII | GGTNACC | none |
| ClaI | ATCGAT | 647, 1526, 1613 |
| DraIII | CACNNNGTG | 1170 |
| EagI | CGGCCG | none |
| EarI | CTCTTC | none |
| EcoRI | GAATTC | 902, 1312, 1562, 1859 |
| EcoRV | GATATC | 383 |
| FokI | GGATG | 295(c), 530(c), 637(c), 725(c), 1345(c) |
| FseI | GGCCGGCC | none |
| HindIII | AAGCTT | none |
| KasI | GGCGCC | none |
| KpnI | GGTACC | 853 |
| MluI | ACGCGT | 131 |
| NarI | GGCGCC | none |
| NcoI | CCATGG | 285 |
| NdeI | CATATG | 80, 1823 |
| NheI | GCTAGC | none |
| NotI | GCGGCCGC | none |
| NsiI | ATGCAT | none |
| PacI | TTAATTAA | none |
| PciI | ACATGT | none |
| PmeI | GTTTAAAC | none |
| PstI | CTGCAG | 689, 1604 |
| PvuI | CGATCG | none |
| PvuII | CAGCTG | 797, 990, 1013, 1723 |
| SacI | GAGCTC | none |
| SacII | CCGCGG | none |
| SalI | GTCGAC | none |
| SapI | GCTCTTC | none |
| SgrAI | CRCCGGYG | none |
| SmaI | CCCGGG | none |
| SpeI | ACTAGT | none |
| SphI | GCATGC | 360 |
| SspI | AATATT | none |
| StuI | AGGCCT | 115 |
| SwaI | ATTTAAAT | none |
| TliI | CTCGAG | none |

-continued

| Name | Sequence | Locations |
|---|---|---|
| XbaI | TCTAGA | none |
| XhoI | CTCGAG | none |
| XmaI | CCCGGG | none |
| XmnI | GAANNNNTTC | 1312 |

6.6 Codon Usage Table

| AmAcid | Codon | Number/ | 1000 | Fraction |
|---|---|---|---|---|
| END | TAA | 1 | 1.68 | 1.0 |
| END | TGA | 0 | 0.0 | 0.0 |
| END | TAG | 0 | 0.0 | 0.0 |
| ALA | GCG | 11 | 18.58 | 0.25 |
| ALA | GCT | 7 | 11.82 | 0.16 |
| ALA | GCA | 18 | 30.40 | 0.41 |
| ALA | GCC | 7 | 11.82 | 0.16 |
| CYS | TGC | 6 | 10.13 | 0.66 |
| CYS | TGT | 3 | 5.06 | 0.33 |
| ASP | GAC | 22 | 37.16 | 0.56 |
| ASP | GAT | 17 | 28.71 | 0.43 |
| GLU | GAA | 37 | 62.5 | 0.86 |
| GLU | GAG | 6 | 10.13 | 0.13 |
| PHE | TTC | 16 | 27.02 | 0.69 |
| PHE | TTT | 7 | 11.82 | 0.30 |
| GLY | GGT | 15 | 25.33 | 0.55 |
| GLY | GGC | 12 | 20.27 | 0.44 |
| GLY | GGG | 0 | 0.0 | 0.0 |
| GLY | GGA | 0 | 0.0 | 0.0 |
| HIS | CAC | 12 | 20.27 | 0.70 |
| HIS | CAT | 5 | 8.44 | 0.29 |
| ILE | ATC | 21 | 35.47 | 0.61 |
| ILE | ATT | 13 | 21.95 | 0.38 |
| ILE | ATA | 0 | 0.0 | 0.0 |
| LYS | AAA | 29 | 48.98 | 0.78 |
| LYS | AAG | 8 | 13.51 | 0.21 |
| LEU | CTG | 66 | 111.48 | 0.98 |
| LEU | CTC | 0 | 0.0 | 0.0 |
| LEU | CTT | 0 | 0.0 | 0.0 |
| LEU | TTG | 0 | 0.0 | 0.0 |

| AmAcid | Codon | -continued Number/1000 | Fraction |
|--------|-------|------------------------|----------|
| LEU | TTA | 0 | 0.0 | 0.0 |
| LEU | CTA | 1 | 1.68 | 0.01 |
| MET | ATG | 21 | 35.47 | 1.0 |
| ASN | AAC | 21 | 35.47 | 0.91 |
| ASN | AAT | 2 | 3.37 | 0.08 |
| PRO | CCG | 21 | 35.47 | 0.72 |
| PRO | CCA | 3 | 5.06 | 0.10 |
| PRO | CCT | 5 | 8.44 | 0.17 |
| PRO | CCC | 0 | 0.0 | 0.0 |
| GLN | CAG | 22 | 37.16 | 0.81 |
| GLN | CAA | 5 | 8.44 | 0.18 |
| ARG | CGT | 25 | 42.22 | 0.75 |
| ARG | CGC | 8 | 13.51 | 0.24 |
| ARG | AGA | 0 | 0.0 | 0.0 |
| ARG | CGG | 0 | 0.0 | 0.0 |
| ARG | CGA | 0 | 0.0 | 0.0 |
| ARG | AGG | 0 | 0.0 | 0.0 |
| SER | TCT | 8 | 13.51 | 0.28 |
| SER | TCC | 9 | 15.20 | 0.32 |
| SER | AGC | 11 | 18.58 | 0.39 |
| SER | TCG | 0 | 0.0 | 0.0 |
| SER | TCA | 0 | 0.0 | 0.0 |
| SER | AGT | 0 | 0.0 | 0.0 |
| THR | ACC | 12 | 20.27 | 0.48 |
| THR | ACT | 7 | 11.82 | 0.28 |
| THR | ACG | 6 | 10.13 | 0.24 |
| THR | ACA | 0 | 0.0 | 0.0 |
| VAL | GTT | 10 | 16.89 | 0.31 |
| VAL | GTG | 8 | 13.51 | 0.25 |
| VAL | GTA | 8 | 13.51 | 0.25 |
| VAL | GTC | 6 | 10.13 | 0.18 |
| TRP | TGG | 7 | 11.82 | 1.0 |
| TYR | TAC | 18 | 30.40 | 0.66 |
| TYR | TAT | 9 | 15.20 | 0.33 |

6.7 GC Content of the Design Nucleic Acid Sequence

GC Percentage: 51.20%

6.8 Repeat Analysis

Repeats greater than or equal to 12, in screenshot project None

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Aspects of the present invention can be implemented as a computer program product that comprises a computer program mechanism embedded in a computer readable storage medium. For instance, the computer program product could contain the program modules and/or data structures shown in FIG. 1. These program modules may be stored on a CD-ROM, magnetic disk storage product, digital video disk (DVD) or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A computer program product for use in conjunction with a computer system, the computer program product comprising a tangible computer readable storage medium and a computer program mechanism embedded therein, the computer program mechanism for designing and manipulating a set of sequence elements in order to design a design nucleic acid sequence, the computer program mechanism comprising:

(I) instructions for representing the set of sequence elements on a display, each sequence element representing an amino acid sequence segment or a nucleic acid sequence segment, wherein the set of sequence elements collectively encode the design nucleic acid sequence, wherein said instructions for representing said set of sequence elements comprise instructions for displaying a plurality of icons in a linear or a near linear arrangement on a display, each respective icon in said plurality of icons uniquely representing a corresponding sequence element in said set of sequence elements such that neighboring icons in said plurality of icons represent neighboring sequence elements in said plurality of sequence elements in said design nucleic acid sequence, and each said respective icon in said plurality of icons depicts a directional property for the corresponding sequence element in said set of sequence elements; and (II) instructions for permitting a user to rearrange an order of the icons on a display thereby causing a corresponding change in the nucleic acid sequence of the design nucleic acid sequence.

2. The computer program product of claim 1, wherein said directional property for a corresponding sequence element in said set of sequence elements is a translation direction or a transcription direction.

3. The computer program product of claim 1, wherein said instructions for displaying a set of icons further comprise instructions for displaying an icon in said plurality of icons in an icon view or a sequence view, wherein, when said icon is displayed in the icon view, a graphical depiction of the sequence element represented by said icon is displayed, and when said icon is displayed in the sequence view, a sequence represented by said icon is displayed.

4. The computer program product of claim 3, wherein, when said icon is displayed in said sequence view, a name of the sequence element represented by the icon is displayed above said sequence.

5. The computer program product of claim 3, wherein, when said icon is displayed in said sequence view, a start position and an end position of the sequence element that said icon represents in said design nucleic acid sequence is displayed.

6. The computer program product of claim 3, wherein the sequence represented by said icon is an amino acid sequence and, for each respective amino acid in said amino acid sequence, each codon corresponding to said respective amino acid is displayed below the respective amino acid.

7. The computer program product of claim 3, wherein the sequence represented by said icon is an amino acid sequence.

8. The computer program product of claim 3, wherein the sequence represented by said icon is a nucleic acid sequence.

9. The computer program product of claim 1, the computer program mechanism further comprising:

a library of sequence elements;

instructions for depicting said library of sequence elements; and instructions for permitting a user to drag a copy of a sequence element in said library of sequence elements onto a panel, thereby incorporating said sequence element into said set of sequence elements and thereby changing the nucleic acid sequence of the design nucleic acid sequence.

10. The computer program product of claim 9, the computer program mechanism further comprising:
   instructions for permitting a user to modify a sequence element in said set of sequence elements; and
   instructions for permitting a user to add a sequence element from said set of sequence elements to said library of sequence elements.

11. The computer program product of claim 9, wherein the library of sequence elements are organized in a hierarchical tree that is graphically displayed.

12. The computer program product of claim 9, wherein the library of sequence elements are organized in a hierarchical tree that is graphically displayed, and wherein said hierarchical tree is divided into a first portion representing regulatory elements, a second portion representing expressed elements, and a third portion representing cloning elements.

13. The computer program product of claim 12, wherein the portion of said hierarchical tree representing regulatory elements is further divided into a subportion representing sequence elements that are transcriptional elements and a subportion representing sequence elements that are translational elements.

14. The computer program product of claim 13, wherein the portion of said hierarchical tree representing transcriptional elements is further divided into one or more of the following subportions:
   a subportion representing sequence elements that are enhancers;
   a subportion representing sequence elements that are promoters;
   a subportion representing sequence elements that are operators;
   a subportion representing sequence elements that are terminators; and
   a subportion representing sequence elements that are polyadenylation signals.

15. The computer program product of claim 13, wherein the portion of said hierarchical tree representing translational elements is further divided into one or more of the following subportions:
   a subportion representing sequence elements that are 5' and 3' untranslated regions;
   a subportion representing sequence elements that are ribosome binding sites;
   a subportion representing sequence elements that are initiation AUG contexts; and
   a subportion representing sequence elements that are termination codons.

16. The computer program product of claim 12, wherein the portion of said hierarchical tree representing expressed elements is further divided into one or more of the following subportions:
   a subportion representing sequence elements that are peptide fusion tags;
   a subportion representing sequence elements that are protease cleavage sites;
   a subportion representing sequence elements that are solubility or fusion tags; and
   a subportion representing sequence elements that are secretion signals.

17. The computer program product of claim 16, wherein the portion of said hierarchical tree representing expressed elements is further divided according to organism of origin.

18. The computer program product of claim 12, wherein the portion of said hierarchical tree representing cloning elements is further divided into one or more of the following subportions:
   a subportion representing sequence elements that are recombinase recognition sequences; and
   a subportion representing sequence elements that are restriction enzyme recognition sequences.

19. The computer program product of claim 1, the computer program mechanism further comprising
   instructions for depicting an empty sequence element; and
   instructions for permitting a user to drag a copy of the empty sequence element onto a panel, thereby incorporating said empty sequence element into said set of sequence elements, wherein, when said user drags said copy of the empty sequence element onto said panel said instructions for permitting a user further comprise instructions for prompting said user for an amino acid sequence, a nucleic acid sequence, or an open reading frame.

20. The computer program product of claim 1, wherein each sequence element in said set of sequence elements is an amino acid element, a DNA element, or an open reading frame element.

21. The computer program product of claim 20, the computer program product further comprising instructions for back-translating a sequence element in said set of sequence elements that is an amino acid element or an open reading frame element into said design nucleic acid sequence.

22. The computer program product of claim 21, wherein the sequence element is an amino acid sequence and the instructions for back-translating produce the corresponding nucleic acid sequence as a function of (i) the amino acid sequence and (ii) common codon use in a designated species.

23. The computer program product of claim 21, wherein
   the instructions for back-translating further comprise instructions for avoiding the generation of one or more restriction enzyme recognition sequences in said design nucleic acid sequence; and wherein
   the computer program mechanism further comprises instructions for receiving an identity of the one or more restriction enzyme recognition sequences to be avoided from a user.

24. The computer program product of claim 21, wherein the instructions for back-translating further comprise instructions for considering one or more criteria when back-translating, the one or more criteria selected from the group consisting of:
   (i) minimization of a repeated nucleic acid sequence in the design nucleic acid sequence;
   (ii) avoidance of a predetermined nucleic acid sequence in the design nucleic acid sequence;
   (iii) minimization of a secondary structure in the design nucleic acid sequence;
   (iv) minimization of sequence identity of the design nucleic acid sequence with respect to a reference sequence or maximization of sequence identity with respect to said reference sequence;
   (v) avoidance of an enzyme recognition sequence in the design nucleic acid sequence;
   (vi) selection of a codon based on codon frequency specified by a codon table;
   (vii) elimination of a methylation site that would inhibit the action of an enzyme in the design nucleic acid sequence; and
   (viii) avoidance of a first subsequence in the design nucleic acid sequence that has an annealing temperature with a second subsequence in the design nucleic acid sequence that is above a predetermined value.

25. The computer program product of claim 21, the computer program product further comprising instructions for fixing and unfixing the sequence element, wherein,
   when the sequence element is fixed, it cannot be subjected to back-translation optimization; and
   when the sequence element is unfixed, it can be further subjected to back-translation optimization.

26. The computer program product of claim 20, wherein the computer program mechanism further comprises:
    instructions for independently toggling an open reading frame element in said set of sequence elements between a fixed state and an unfixed state; and
    instructions for back-translating a sequence element in said set of sequence elements that is an open reading frame element in an unfixed state into the design nucleic acid sequence.

27. The computer program product of claim 26, wherein the instructions for back-translating further comprise instructions for avoiding the generation of one or more restriction enzyme recognition sequences in said design nucleic acid sequence; and wherein
    the computer program mechanism further comprises instructions for receiving an identity of the one or more restriction enzyme recognition sequences to be avoided from a user.

28. The computer program product of claim 26, wherein the instructions for back-translating further comprise instructions for considering one or more criteria when back-translating, the one or more criteria selected from the group consisting of:
    (i) minimization of a repeated nucleic acid sequence in the design nucleic acid sequence;
    (ii) avoidance of a predetermined nucleic acid sequence in the design nucleic acid sequence;
    (iii) minimization of a secondary structure in the design nucleic acid sequence;
    (iv) minimization of sequence identity of the design nucleic acid sequence with respect to a reference sequence or maximization of sequence identity with respect to said reference sequence;
    (v) avoidance of an enzyme recognition sequence in the design nucleic acid sequence;
    (vi) selection of a codon based on codon frequency specified by a codon table;
    (vii) elimination of a methylation site that would inhibit the action of an enzyme in the design nucleic acid sequence; and
    (viii) avoidance of a first subsequence in the design nucleic acid sequence that has an annealing temperature with a second subsequence in the design nucleic acid sequence that is above a predetermined value.

29. The computer program product of claim 26, the computer program product further comprising instructions for fixing and unfixing the sequence element, wherein,
    when the sequence element is fixed, it cannot be subjected to further back-translation optimization; and
    when the sequence element is unfixed, it can be further subjected to back-translation optimization.

30. The computer program product of claim 1, wherein said linear or near linear arrangement is broken into a plurality of horizontal rows.

31. The computer program product of claim 1, wherein the computer program mechanism further comprises:
    instructions for permitting a user to change an attribute of an icon in said plurality of icons.

32. The computer program product of claim 31, wherein the attribute is a name of said icon, a color of said icon, a size of said icon, a resolution of said icon, a sequence associated with said icon or a name associated with said icon.

33. The computer program product of claim 1, wherein a sequence element in said set of sequence elements is a DNA element, wherein said instructions for displaying a set of icons further comprise instructions for displaying a first icon in said plurality of icons representing said DNA element in an icon view or a sequence view, wherein,
    when said first icon is displayed in the icon view, a graphical depiction of the sequence element represented by said first icon is displayed, and
    when said first icon is displayed in the sequence view, a nucleic acid sequence represented by said first icon is displayed and all six reading frames of said nucleic acid sequence represented by said icon is displayed.

34. The computer program product of claim 1, wherein a sequence element in said set of sequence elements is an amino acid element, the computer program product further comprising:
    instructions for back-translating said amino acid element to said design nucleic acid sequence; and wherein
    said instructions for displaying a set of icons further comprise instructions for displaying an icon in said plurality of icons representing said amino acid element in an icon view or a sequence view, wherein,
    when said icon is displayed in the icon view, a graphical depiction of the sequence element represented by said icon is displayed, and
    when said icon is displayed in the sequence view, an amino acid sequence represented by said icon is displayed and, for each respective amino acid in said amino acid sequence, each possible codon for said respective amino acid is displayed below the respective amino acid.

35. The computer program product of claim 34, wherein codons for each respective amino acid in said amino acid sequence are ranked in the sequence view in accordance with frequencies found for such codons in a codon bias table.

36. The computer program product of claim 35, the computer program product further comprising instructions for obtaining said codon bias table from among a plurality of codon bias tables, wherein said codon bias table indicates a frequency for each possible codon encoding a naturally occurring amino acid.

37. The computer program product of claim 36, wherein said frequency for each possible codon encoding a naturally occurring amino acid is the frequency of occurrence of each possible codon encoding a naturally occurring amino acid in a species corresponding to said codon bias table.

38. The computer program product of claim 36, wherein said frequency for each possible codon encoding a naturally occurring amino acid is calculated from the frequency of occurrence of each possible codon encoding a naturally occurring amino acid in two or more species corresponding to said codon bias table.

39. The computer program product of claim 35, the computer program product further comprising:
    instructions for setting a back-translation threshold; and wherein
    said instructions for back-translating include instructions for excluding codons in said corresponding nucleic acid sequence that are below said back-translation threshold in a codon bias table.

40. The computer program product of claim 39, the computer program product further comprising:
    instructions for displaying codons that fall below said back-translation threshold in a first color; and
    instructions for displaying codons that are above said back-translation threshold in a second color.

41. The computer program product of claim 1, the computer program product further comprising:
    instructions for displaying a restriction site analysis box comprising a plurality of restrictions site names and, for each restriction site name in the plurality of restriction site names, the corresponding restriction sequence; and instructions for indicating positions of one or more restriction sites in the plurality of restriction sites in said set of sequence elements that are displayed as a plurality of icons in said linear or said near linear arrangement.

42. The computer program product of claim 41, wherein a sequence element in said set of sequence elements comprises an amino acid sequence or an open reading frame and wherein said instructions for indicating positions of one or more restriction sites comprises instructions for indicating a position where a restriction site could occur in said amino acid sequence or said open reading frame without changing said amino acid sequence or said open reading frame.

43. The computer program product of claim 41, the computer program product further comprising:
    instructions for adding or removing a restriction site name to said plurality of restriction site names; and
    instructions for selecting and deselecting a restriction site name in said plurality of restriction site names, wherein, when the restriction site name is selected the position of each restriction site in said set of sequence elements corresponding to said restriction site name is displayed.

44. The computer program product of claim 1, wherein a sequence element in said set of sequence elements is an open reading frame element, the computer program product further comprising:
    instructions for setting a codon usage threshold; and wherein
    said instructions for displaying a set of icons further comprise instructions for displaying a first icon in said plurality of icons representing said open reading frame element in an icon view or a sequence view, wherein,
        when said first icon is displayed in the icon view, a graphical depiction of the sequence element represented by said first icon is displayed, and
        when said first icon is displayed in the sequence view, an amino acid sequence represented by said first icon is displayed and, for each respective amino acid in said amino acid sequence,
            each possible codon for said respective amino acid is displayed;
            the actual codon used by the open reading frame element is indicated in a first color when the actual codon has a frequency in a codon bias table that is above the codon usage threshold; and
            the actual codon used by the open reading frame element is indicated in a second color when the actual codon has a frequency in the codon bias table that is below the codon usage threshold.

45. The computer program product of claim 44, wherein the amino acid sequence represented by the first icon is determined by a (i) nucleic acid sequence represented by the first icon and (ii) a reading frame of a second icon that precedes or follows said first icon in the linear or near linear arrangement, wherein said second icon represents an amino acid element.

46. The computer program product of claim 1, wherein said instructions for displaying a set of icons further comprise instructions for displaying an icon in said plurality of icons in an icon view or a sequence view, wherein,
    when said icon is displayed in said icon view, a graphical depiction of the sequence element represented by said icon is displayed, and
    when said icon is displayed in said sequence view, a first sequence represented by said icon is displayed, wherein said first sequence is a nucleic acid sequence or an amino acid sequence represented by said icon; and
    when said icon is displayed in said sequence view, all or a portion of the design nucleic acid sequence is displayed above said first sequence, wherein said design nucleic acid sequence corresponds to all or a portion of the amino acid sequence segments and/or the nucleic acid sequence segments of said set of sequence elements.

47. The computer program product of claim 46, wherein said first sequence is an amino acid sequence and said computer program mechanism further comprises instructions for back-translating all or a portion of said first sequence thereby constructing a corresponding portion of the design nucleic acid sequence.

48. The computer program product of claim 46, wherein said first sequence is an amino acid sequence and said computer program mechanism further comprises:
    instructions for positioning a graphic icon at a position in said first sequence where a restriction site can be introduced without changing said first sequence; and
    instructions for placing the restriction site recognition sequence in a corresponding position in said second design nucleic acid sequence when a user selects said graphic icon to indicate that the restriction site is desired.

49. The computer program product of claim 48, wherein said computer program mechanism further comprises:
    instructions for graphically displaying overhangs generated by cleavage of the restriction site recognition sequence; and
    instructions for displaying the name of the restriction enzyme that recognizes the restriction site recognition sequence in the vicinity of the restriction site recognition sequence in the design nucleic acid sequence.

50. The computer program product of claim 48, wherein,
    said instructions for displaying further comprise, for each respective amino acid in said first sequence, instructions for displaying each codon corresponding to said respective amino acid sequence below said first sequence; and
    said instructions for placing further comprise instructions for highlighting each codon below said first sequence that is in the restriction site recognition sequence when a user selects said graphic icon to indicate that the restriction site is desired.

51. The computer program product of claim 46, the computer program mechanism further comprising:
    a $T_m$ calculation module, the $T_m$ calculation module comprising:
        instructions for selecting a start point and an end point in said design nucleic acid sequence, thereby defining an oligonucleotide;
        instructions for computing a $T_m$ of the oligonucleotide; and
        instructions for displaying the $T_m$ of the oligonucleotide.

52. The computer program product of claim 51, wherein the instructions for displaying the $T_m$ of the oligonucleotide comprise instructions for displaying the $T_m$ and a numeric representation of the start point and the end point.

53. The computer program product of claim 51, wherein the $T_m$ calculation module further comprises instructions for moving the start point and/or the end point and, for each new start point and/or end point specified by the user, repeating said instructions for computing and said instructions for displaying.

54. The computer program product of claim 46, the computer program mechanism further comprising:
    an oligonucleotide marker module, the oligonucleotide marker module comprising:

instructions for selecting a start point and an end point in said design nucleic acid sequence, thereby defining an oligonucleotide;

instructions for defining a 5' to 3' direction of the oligonucleotide; and instructions for displaying the oligonucleotide as a graphic above or below the design nucleic acid sequence.

55. The computer program product of claim 1, wherein said instructions for displaying a set of icons further comprise instructions for displaying a plurality of icons in an icon view or a sequence view, wherein, when said plurality of icons are displayed in said icon view, a graphical depiction of the set of sequence elements represented by said plurality of icons is displayed, and when said plurality of icons are displayed in said sequence view, a plurality of sequences, each represented by one of said plurality of icons is displayed, wherein each sequence is a nucleic acid sequence or an amino acid sequence; and when said plurality of icons are displayed in sequence view, said design nucleic acid sequence is displayed above said plurality of sequences.

56. The computer program product of claim 1, the computer program mechanism further comprising:

instructions for merging a first sequence element and a second sequence element in said set of sequence elements thereby forming a single sequence element in said set of sequence elements from said first sequence element and said second sequence element.

57. The computer program product of claim 1, the computer program mechanism further comprising:

instructions for selecting a portion of a first sequence element in said set of sequence elements and splitting said portion of said first sequence element into a new second sequence element in said set of sequence elements.

58. The computer program product of claim 1, the computer program mechanism further comprising:

instructions for selecting a contiguous sequence wherein said contiguous sequence is all or a portion of two or more adjacent sequence elements in said linear or near linear arrangement; and instructions for splitting said contiguous sequence into a new sequence element in said set of sequence elements and eliminating said contiguous sequence in said two or more adjacent sequence elements.

59. The computer program product of claim 1, the computer program mechanism further comprising:

instructions for saving said set of sequence elements as a first project;

instructions for permitting the selection of a project from among a plurality of projects; each project in the plurality of projects comprising a set of sequence elements; and instructions for linking a first sequence element in the set of sequence elements in the first project with a corresponding second sequence element in a set of sequence elements in another project in said plurality of projects such that, when changes are made to a nucleic acid sequence associated with said first sequence element, the same changes are made to a nucleic acid sequence associated with the second sequence element.

60. The computer program product of claim 59, the computer program mechanism further comprising:

instructions for removing the link between the first sequence element and the second sequence element.

61. The computer program product of claim 59, the computer program mechanism further comprising:

instructions for locking the nucleic acid sequence associated with said first sequence element and the nucleic acid sequence associated with said second sequence element so that no change is allowed to either nucleic acid sequence.

62. The computer program product of claim 1, the computer program mechanism further comprising:

instructions for altering a directional property of a sequence element in said set of sequence elements.

63. The computer program product of claim 62, wherein the directional property is a translation direction or a transcription direction.

64. The computer program product of claim 1, the computer program product further comprising:

instructions for generating a report, the report comprising any combination of:

(i) the design nucleic acid sequence;

(ii) a nucleic acid sequence associated with each sequence element in said set of sequence elements;

(iii) a codon translation map for the design nucleic acid sequence;

(iv) a restriction site summary for the design nucleic acid sequence;

(v) a codon usage frequency analysis for the design nucleic acid sequence;

(vi) a GC content for the design nucleic acid sequence;

(vii) a list of repeats in the design nucleic acid sequence; and (viii) a list of each oligonucleotide associated with the set of sequence elements.

65. The computer program product of claim 1, wherein a first sequence element in said set of sequence elements is a DNA element and a second sequence element in said set of sequence elements in a first amino acid element, wherein said instructions for displaying a set of icons further comprise instructions for displaying a first icon in said plurality of icons representing said DNA element in an icon view or a sequence view, wherein, when said first icon is displayed in the icon view, a graphical depiction of the sequence element represented by said first icon is displayed, and when said first icon is displayed in the sequence view, all six reading frames of said DNA element is displayed, and wherein a first reading frame in the six reading frames that is in frame with the first amino acid element is highlighted in a first manner.

66. The computer program product of claim 65, wherein a third sequence element in said set of sequence elements is an amino acid element, and wherein when said first icon is displayed in the sequence view, a second frame in the six reading frames that is in frame with the second amino acid element is highlighted in a second manner.

67. The computer program product of claim 1, the computer program product further comprising:

instructions for communicating a sequence of the design nucleic acid sequence across a network as part of an order for said design nucleic acid sequence.

68. The computer program product of claim 67, wherein the network in the Internet.

69. The computer program product of claim 67, wherein the sequence is encrypted.

* * * * *

(12) EX PARTE REEXAMINATION CERTIFICATE (10366th)
United States Patent
Gustafsson et al.

(10) Number: US 7,805,252 C1
(45) Certificate Issued: Oct. 28, 2014

(54) SYSTEMS AND METHODS FOR DESIGNING AND ORDERING POLYNUCLEOTIDES

(75) Inventors: Claes Gustafsson, Belmont, CA (US); Sridhar Govindarajan, Redwood City, CA (US); Jon E. Ness, Redwood City, CA (US); Alan Marco Villalobos, Mountain View, CA (US); Jeremy Minshull, Los Altos, CA (US)

(73) Assignee: DNA Twopointo Inc., Menlo Park, CA (US)

Reexamination Request:
No. 90/013,101, Dec. 20, 2013

Reexamination Certificate for:
Patent No.: 7,805,252
Issued: Sep. 28, 2010
Appl. No.: 11/207,151
Filed: Aug. 16, 2005

(51) Int. Cl.
*G06F 7/00* (2006.01)
(52) U.S. Cl.
USPC .............................................. 702/19; 702/20
(58) Field of Classification Search
None
See application file for complete search history.

(56) References Cited

To view the complete listing of prior art documents cited during the proceeding for Reexamination Control Number 90/013,101, please refer to the USPTO's public Patent Application Information Retrieval (PAIR) system under the Display References tab.

*Primary Examiner* — Shri Ponnaluri

(57) ABSTRACT

Computer systems, computer program products and methods for designing oligonucleotides are provided. A set of sequence elements is defined. Each sequence element represents an amino acid sequence segment or a nucleic acid sequence segment. The set of sequence elements collectively represent a design nucleic acid sequence. The set of sequence elements are displayed as a plurality icons in a linear or a near linear arrangement such that each respective icon in the plurality of icons uniquely represents a corresponding sequence element in the set of sequence elements. In this representation, neighboring icons in the plurality of icons represent neighboring sequence elements in the set of sequence elements. Each respective icon in the plurality of icons depicts a directional property for the corresponding sequence element in the set of sequence elements. An oligonucleotide selection module is used to identify oligonucleotides in the design nucleic acid sequence.

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-69 are determined to be patentable as amended.

New claims 70-74 are added and determined to be patentable.

1. [A computer program product for use in conjunction with a computer system, the computer program product comprising a tangible] *A non-transitory* computer readable storage medium and a computer program mechanism embedded therein, the computer program mechanism for designing and manipulating a set of sequence elements in order to design a design nucleic acid sequence, the computer program mechanism comprising *instructions, executed by one or more processors, for*:
   (I) [instructions for] representing the set of sequence elements on a display, each sequence element representing an amino acid sequence segment or a nucleic acid sequence segment, wherein the set of sequence elements collectively encode the design nucleic acid sequence, wherein said instructions for representing said set of sequence elements comprise instructions for displaying a plurality of icons in a linear or a near linear arrangement on [a] *the* display, *and* each respective icon in said plurality of icons uniquely [representing] *represents* a corresponding sequence element in said set of sequence elements such that neighboring icons in said plurality of icons represent neighboring sequence elements in said plurality of sequence elements in said design nucleic acid sequence[, and
   and each said respective icon in said plurality of icons depicts];
   *(II) providing on the display* a directional property for [the corresponding] *a respective* sequence element in said set of sequence elements; and
   [(II)] *(III)* [instructions for] permitting a user to rearrange an order of the icons on [a] *the* display thereby causing a corresponding change in the nucleic acid sequence of the design nucleic acid sequence.

2. The [computer program product] *non-transitory computer readable storage medium* of claim 1, wherein said directional property [for a corresponding sequence element in said set of sequence elements] is a translation direction or a transcription direction.

3. The [computer program product] *non-transitory computer readable storage medium* of claim 1, wherein said instructions for displaying a set of icons further comprise instructions for displaying an icon in said plurality of icons in an icon view or a sequence view, wherein,
   when said icon is displayed in the icon view, a graphical depiction of the sequence element represented by said icon is displayed, and
   when said icon is displayed in the sequence view, a sequence represented by said icon is displayed.

4. The [computer program product] *non-transitory computer readable storage medium* of claim 3, wherein, when said icon is displayed in said sequence view, a name of the sequence element represented by the icon is displayed above said sequence.

5. The [computer program product] *non-transitory computer readable storage medium* of claim 3, wherein, when said icon is displayed in said sequence view, a start position and an end position of the sequence element that said icon represents in said design nucleic acid sequence is displayed.

6. The [computer program product] *non-transitory computer readable storage medium* of claim 3, wherein the sequence represented by said icon is an amino acid sequence and, for each respective amino acid in said amino acid sequence, each codon corresponding to said respective amino acid is displayed below the respective amino acid.

7. The [computer program product] *non-transitory computer readable storage medium* of claim 3, wherein the sequence represented by said icon is an amino acid sequence.

8. The [computer program product] *non-transitory computer readable storage medium* of claim 3, wherein the sequence represented by said icon is a nucleic acid sequence.

9. The [computer program product] *non-transitory computer readable storage medium* of claim 1, the computer program mechanism further comprising:
   a library of sequence elements;
   instructions for depicting said library of sequence elements; and
   instructions for permitting a user to drag a copy of a sequence element in said library of sequence elements onto a panel, thereby incorporating said sequence element into said set of sequence elements and thereby changing the nucleic acid sequence of the design nucleic acid sequence.

10. The [computer program product] *non-transitory computer readable storage medium* of claim 9, the computer program mechanism further comprising:
   instructions for permitting a user to modify a sequence element in said set of sequence elements; and
   instructions for permitting a user to add a sequence element from said set of sequence elements to said library of sequence elements.

11. The [computer program product] *non-transitory computer readable storage medium* of claim 9, wherein the library of sequence elements are organized in a hierarchical tree that is graphically displayed.

12. The [computer program product] *non-transitory computer readable storage medium* of claim 9, wherein the library of sequence elements are organized in a hierarchical tree that is graphically displayed, and wherein said hierarchical tree is divided into a first portion representing regulatory elements, a second portion representing expressed elements, and a third portion representing cloning elements.

13. The [computer program product] *non-transitory computer readable storage medium* of claim 12, wherein the portion of said hierarchical tree representing regulatory elements is further divided into a subportion representing sequence elements that are transcriptional elements and a subportion representing sequence elements that are translational elements.

14. The [computer program product] *non-transitory computer readable storage medium* of claim 13, wherein the portion of said hierarchical tree representing transcriptional elements is further divided into one or more of the following subportions:

a subportion representing sequence elements that are enhancers;
a subportion representing sequence elements that are promoters;
a subportion representing sequence elements that are operators;
a subportion representing sequence elements that are terminators; and
a subportion representing sequence elements that are polyadenylation signals.

15. The [computer program product] *non-transitory computer readable storage medium* of claim 13, wherein the portion of said hierarchical tree representing translational elements is further divided into one or more of the following subportions:
a subportion representing sequence elements that are 5' and 3' untranslated regions;
a subportion representing sequence elements that are ribosome binding sites;
a subportion representing sequence elements that are initiation AUG contexts; and
a subportion representing sequence elements that are termination codons.

16. The [computer program product] *non-transitory computer readable storage medium* of claim 12, wherein the portion of said hierarchical tree representing expressed elements is further divided into one or more of the following subportions:
a subportion representing sequence elements that are peptide fusion tags;
a subportion representing sequence elements that are protease cleavage sites;
a subportion representing sequence elements that are solubility or fusion tags; and
a subportion representing sequence elements that are secretion signals.

17. The [computer program product] *non-transitory computer readable storage medium* of claim 16, wherein the portion of said hierarchical tree representing expressed elements is further divided according to organism of origin.

18. The [computer program product] *non-transitory computer readable storage medium* of claim 12, wherein the portion of said hierarchical tree representing cloning elements is further divided into one or more of the following subportions:
a subportion representing sequence elements that are recombinase recognition sequences; and
a subportion representing sequence elements that are restriction enzyme recognition sequences.

19. The [computer program product] *non-transitory computer readable storage medium* of claim 1, the computer program mechanism further comprising:
instructions for depicting an empty sequence element; and
instructions for permitting a user to drag a copy of the empty sequence element onto a panel, thereby incorporating said empty sequence element into said set of sequence elements, wherein, when said user drags said copy of the empty sequence element onto said panel said instructions for permitting a user further comprise instructions for prompting said user for an amino acid sequence, a nucleic acid sequence, or an open reading frame.

20. The [computer program product] *non-transitory computer readable storage medium* of claim 1, wherein each sequence element in said set of sequence elements is an amino acid element, a DNA element, or an open reading frame element.

21. The [computer program product] *non-transitory computer readable storage medium* of claim 20, the computer program [product] *mechanism* further comprising instructions for back-translating a sequence element in said set of sequence elements that is an amino acid element or an open reading frame element into said design nucleic acid sequence.

22. The [computer program product] *non-transitory computer readable storage medium* of claim 21, wherein the sequence element is an amino acid sequence and the instructions for back-translating produce the corresponding nucleic acid sequence as a function of (i) the amino acid sequence and (ii) common codon use in a designated species.

23. The [computer program product] *non-transitory computer readable storage medium* of claim 21, wherein the instructions for back-translating further comprise instructions for avoiding the generation of one or more restriction enzyme recognition sequences in said design nucleic acid sequence; and wherein
the computer program mechanism further comprises instructions for receiving an identity of the one or more restriction enzyme recognition sequences to be avoided from a user.

24. The [computer program product] *non-transitory computer readable storage medium* of claim 21, wherein the instructions for back-translating further comprise instructions for considering one or more criteria when back-translating, the one or more criteria selected from the group consisting of:
(i) minimization of a repeated nucleic acid sequence in the design nucleic acid sequence;
(ii) avoidance of a predetermined nucleic acid sequence in the design nucleic acid sequence;
(iii) minimization of a secondary structure in the design nucleic acid sequence;
(iv) minimization of sequence identity of the design nucleic acid sequence with respect to a reference sequence or maximization of sequence identity with respect to said reference sequence;
(v) avoidance of an enzyme recognition sequence in the design nucleic acid sequence;
(vi) selection of a codon based on codon frequency specified by a codon table;
(vii) elimination of a methylation site that would inhibit the action of an enzyme in the design nucleic acid sequence; and
(viii) avoidance of a first subsequence in the design nucleic acid sequence that has an annealing temperature with a second subsequence in the design nucleic acid sequence that is above a predetermined value.

25. The [computer program product] *non-transitory computer readable storage medium* of claim 21, the computer program [product] *mechanism* further comprising instructions for fixing and unfixing the sequence element, wherein,
when the sequence element is fixed, it cannot be subjected to back-translation optimization; and
when the sequence element is unfixed, it can be further subjected to back-translation optimization.

26. The [computer program product] *non-transitory computer readable storage medium* of claim 20, wherein the computer program mechanism further comprises:
instructions for independently toggling an open reading frame element in said set of sequence elements between a fixed state and an unfixed state; and
instructions for back-translating a sequence element in said set of sequence elements that is an open reading frame element in an unfixed state into the design nucleic acid sequence.

27. The [computer program product] *non-transitory computer readable storage medium* of claim 26, wherein
the instructions for back-translating further comprise instructions for avoiding the generation of one or more restriction enzyme recognition sequences in said design nucleic acid sequence; and wherein
the computer program mechanism further comprises instructions for receiving an identity of the one or more restriction enzyme recognition sequences to be avoided from a user.

28. The [computer program product] *non-transitory computer readable storage medium* of claim 26, wherein the instructions for back-translating further comprise instructions for considering one or more criteria when back-translating, the one or more criteria selected from the group consisting of:
(i) minimization of a repeated nucleic acid sequence in the design nucleic acid sequence;
(ii) avoidance of a predetermined nucleic acid sequence in the design nucleic acid sequence;
(iii) minimization of a secondary structure in the design nucleic acid sequence;
(iv) minimization of sequence identity of the design nucleic acid sequence with respect to a reference sequence or maximization of sequence identity with respect to said reference sequence;
(v) avoidance of an enzyme recognition sequence in the design nucleic acid sequence;
(vi) selection of a codon based on codon frequency specified by a codon table;
(vii) elimination of a methylation site that would inhibit the action of an enzyme in the design nucleic acid sequence; and
(viii) avoidance of a first subsequence in the design nucleic acid sequence that has an annealing temperature with a second subsequence in the design nucleic acid sequence that is above a predetermined value.

29. The [computer program product] *non-transitory computer readable storage medium* of claim 26, the computer program [product] *mechanism* further comprising instructions for fixing and unfixing the sequence element, wherein,
when the sequence element is fixed, it cannot be subjected to further back-translation optimization; and
when the sequence element is unfixed, it can be further subjected to back-translation optimization.

30. The [computer program product] *non-transitory computer readable storage medium* of claim 1, wherein said linear or near linear arrangement is broken into a plurality of horizontal rows.

31. The [computer program product] *non-transitory computer readable storage medium* of claim 1, wherein the computer program mechanism further comprises:
instructions for permitting a user to change an attribute of an icon in said plurality of icons.

32. The [computer program product] *non-transitory computer readable storage medium* of claim 31, wherein the attribute is a name of said icon, a color of said icon, a size of said icon, a resolution of said icon, a sequence associated with said icon or a name associated with said icon.

33. The [computer program product] *non-transitory computer readable storage medium* of claim 1, wherein
a sequence element in said set of sequence elements is a DNA element,
[wherein] said instructions for displaying a set of icons further comprise instructions for displaying a first icon in said plurality of icons representing said DNA element in an icon view or a sequence view, *and*
wherein,
when said first icon is displayed in the icon view, a graphical depiction of the sequence element represented by said first icon is displayed, and
when said first icon is displayed in the sequence view, a nucleic acid sequence represented by said first icon is displayed and all six reading frames of said nucleic acid sequence represented by said icon is displayed.

34. The [computer program product] *non-transitory computer readable storage medium* of claim 1, wherein
a sequence element in said set of sequence elements is an amino acid element,
the computer program [product] *mechanism* further comprising:
instructions for back-translating said amino acid element to said design nucleic acid sequence; and
wherein said instructions for displaying a set of icons further comprise instructions for displaying an icon in said plurality of icons representing said amino acid element in an icon view or a sequence view, wherein,
when said icon is displayed in the icon view, a graphical depiction of the sequence element represented by said icon is displayed, and
when said icon is displayed in the sequence view, an amino acid sequence represented by said icon is displayed and, for each respective amino acid in said amino acid sequence, each possible codon for said respective amino acid is displayed below the respective amino acid.

35. The [computer program product] *non-transitory computer readable storage medium* of claim 34, wherein codons for each respective amino acid in said amino acid sequence are ranked in the sequence view in accordance with frequencies found for such codons in a codon bias table.

36. The [computer program product] *non-transitory computer readable storage medium* of claim 35, the computer program [product] *mechanism* further comprising instructions for obtaining said codon bias table from among a plurality of codon bias tables, wherein said codon bias table indicates a frequency for each possible codon encoding a naturally occurring amino acid.

37. The [computer program product] *non-transitory computer readable storage medium* of claim 36, wherein said frequency for each possible codon encoding a naturally occurring amino acid is the frequency of occurrence of each possible codon encoding a naturally occurring amino acid in a species corresponding to said codon bias table.

38. The [computer program product] *non-transitory computer readable storage medium* of claim 36, wherein said frequency for each possible codon encoding a naturally occurring amino acid is calculated from the frequency of occurrence of each possible codon encoding a naturally occurring amino acid in two or more species corresponding to said codon bias table.

39. The [computer program product] *non-transitory computer readable storage medium* of claim 35, the computer program [product] *mechanism* further comprising:
instructions for setting a back-translation threshold; and
wherein
said instructions for back-translating include instructions for excluding codons in said corresponding nucleic acid sequence that are below said back-translation threshold in a codon bias table.

40. The [computer program product] *non-transitory computer readable storage medium* of claim 39, the computer program [product] *mechanism* further comprising:

instructions for displaying codons that fall below said back-translation threshold in a first color; and instructions for displaying codons that are above said back-translation threshold in a second color.

41. The [computer program product] *non-transitory computer readable storage medium* of claim 1, the computer program [product] *mechanism* further comprising:

instructions for displaying a restriction site analysis box comprising a plurality of restrictions site names and, for each restriction site name in the plurality of restriction site names, the corresponding restriction sequence; and instructions for indicating positions of one or more restriction sites in the plurality of restriction sites in said set of sequence elements that are displayed as a plurality of icons in said linear or said near linear arrangement.

42. The [computer program product] *non-transitory computer readable storage medium* of claim 41, wherein a sequence element in said set of sequence elements comprises an amino acid sequence or an open reading frame and wherein said instructions for indicating positions of one or more restriction sites comprises instructions for indicating a position where a restriction site could occur in said amino acid sequence or said open reading frame without changing said amino acid sequence or said open reading frame.

43. The [computer program product] *non-transitory computer readable storage medium* of claim 41, the computer program [product] *mechanism* further comprising:

instructions for adding or removing a restriction site name to said plurality of restriction site names; and instructions for selecting and deselecting a restriction site name in said plurality of restriction site names, wherein, when the restriction site name is selected the position of each restriction site in said set of sequence elements corresponding to said restriction site name is displayed.

44. The [computer program product] *non-transitory computer readable storage medium* of claim 1, wherein a sequence element in said set of sequence elements is an open reading frame element, the computer program [product] *mechanism* further comprising:

instructions for setting a codon usage threshold; and wherein said instructions for displaying a set of icons further comprise instructions for displaying a first icon in said plurality of icons representing said open reading frame element in an icon view or a sequence view, wherein, when said first icon is displayed in the icon view, a graphical depiction of the sequence element represented by said first icon is displayed, and when said first icon is displayed in the sequence view, an amino acid sequence represented by said first icon is displayed and, for each respective amino acid in said amino acid sequence, each possible codon for said respective amino acid is displayed; the actual codon used by the open reading frame element is indicated in a first color when the actual codon has a frequency in a codon bias table that is above the codon usage threshold; and the actual codon used by the open reading frame element is indicated in a second color when the actual codon has a frequency in the codon bias table that is below the codon usage threshold.

45. The [computer program product] *non-transitory computer readable storage medium* of claim 44, wherein the amino acid sequence represented by the first icon is determined by a (i) nucleic acid sequence represented by the first icon and (ii) a reading frame of a second icon that precedes or follows said first icon in the linear or near linear arrangement, wherein said second icon represents an amino acid element.

46. The [computer program product] *non-transitory computer readable storage medium* of claim 1, wherein said instructions for displaying a set of icons further comprise instructions for displaying an icon in said plurality of icons in an icon view or a sequence view, wherein, when said icon is displayed in said icon view, a graphical depiction of the sequence element represented by said icon is displayed, and when said icon is displayed in said sequence view, a first sequence represented by said icon is displayed, wherein said first sequence is a nucleic acid sequence or an amino acid sequence represented by said icon; and when said icon is displayed in said sequence view, all or a portion of the design nucleic acid sequence is displayed above said first sequence, wherein said design nucleic acid sequence corresponds to all or a portion of the amino acid sequence segments and/or the nucleic acid sequence segments of said set of sequence elements.

47. The [computer program product] *non-transitory computer readable storage medium* of claim 46, wherein said first sequence is an amino acid sequence and said computer program mechanism further comprises instructions for back-translating all or a portion of said first sequence thereby constructing a corresponding portion of the design nucleic acid sequence.

48. The [computer program product] *non-transitory computer readable storage medium* of claim 46, wherein said first sequence is an amino acid sequence and said computer program mechanism further comprises: instructions for positioning a graphic icon at a position in said first sequence where a restriction site can be introduced without changing said first sequence; and instructions for placing the restriction site recognition sequence in a corresponding position in said second design nucleic acid sequence when a user selects said graphic icon to indicate that the restriction site is desired.

49. The [computer program product] *non-transitory computer readable storage medium* of claim 48, wherein said computer program mechanism further comprises:

instructions for graphically displaying overhangs generated by cleavage of the restriction site recognition sequence; and instructions for displaying the name of the restriction enzyme that recognizes the restriction site recognition sequence in the vicinity of the restriction site recognition sequence in the design nucleic acid sequence.

50. The [computer program product] *non-transitory computer readable storage medium* of claim 48, wherein, said instructions for displaying further comprise, for each respective amino acid in said first sequence, instructions for displaying each codon corresponding to said respective amino acid sequence below said first sequence; and said instructions for placing further comprise instructions for highlighting each codon below said first sequence that is in the restriction site recognition sequence when a user selects said graphic icon to indicate that the restriction site is desired.

51. The [computer program product] *non-transitory computer readable storage medium* of claim 46, the computer program mechanism further comprising:

[a $T_m$ calculation module, the $T_m$ calculation module comprising:]

instructions for selecting a start point and an end point in said design nucleic acid sequence, thereby defining an oligonucleotide;

instructions for computing a $T_m$ of the oligonucleotide; and instructions for displaying the $T_m$ of the oligonucleotide.

52. The [computer program product] *non-transitory computer readable storage medium* of claim 51, wherein the instructions for displaying the $T_m$ of the oligonucleotide comprise instructions for displaying the $T_m$ and a numeric representation of the start point and the end point.

53. The [computer program product] *non-transitory computer readable storage medium* of claim 51, wherein the $T_m$ calculation module further comprises instructions for moving the start point and/or the end point and, for each new start point and/or end point specified by the user, repeating said instructions for computing and said instructions for displaying.

54. The [computer program product] *non-transitory computer readable storage medium* of claim 46, the computer program mechanism further comprising: an oligonucleotide marker module, the oligonucleotide marker module comprising: instructions for selecting a start point and an end point in said design nucleic acid sequence, thereby defining an oligonucleotide; instructions for defining a 5' to 3' direction of the oligonucleotide; and instructions for displaying the oligonucleotide as a graphic above or below the design nucleic acid sequence.

55. The [computer program product] *non-transitory computer readable storage medium* of claim 1, wherein said instructions for displaying a set of icons further comprise instructions for displaying a plurality of icons in an icon view or a sequence view, wherein, when said plurality of icons are displayed in said icon view, a graphical depiction of the set of sequence elements represented by said plurality of icons is displayed, and when said plurality of icons are displayed in said sequence view, a plurality of sequences, each represented by one of said plurality of icons is displayed, wherein each sequence is a nucleic acid sequence or an amino acid sequence; and when said plurality of icons are displayed in sequence view, said design nucleic acid sequence is displayed above said plurality of sequences.

56. The [computer program product] *non-transitory computer readable storage medium* of claim 1, the computer program mechanism further comprising: instructions for merging a first sequence element and a second sequence element in said set of sequence elements thereby forming a single sequence element in said set of sequence elements from said first sequence element and said second sequence element.

57. The [computer program product] *non-transitory computer readable storage medium* of claim 1, the computer program mechanism further comprising: instructions for selecting a portion of a first sequence element in said set of sequence elements and splitting said portion of said first sequence element into a new second sequence element in said set of sequence elements.

58. The [computer program product] *non-transitory computer readable storage medium* of claim 1, the computer program mechanism further comprising: instructions for selecting a contiguous sequence wherein said contiguous sequence is all or a portion of two or more adjacent sequence elements in said linear or near linear arrangement; and instructions for splitting said contiguous sequence into a new sequence element in said set of sequence elements and eliminating said contiguous sequence in said two or more adjacent sequence elements.

59. The [computer program product] *non-transitory computer readable storage medium* of claim 1, the computer program mechanism further comprising:

instructions for saving said set of sequence elements as a first project;

instructions for permitting the selection of a project from among a plurality of projects; each project in the plurality of projects comprising a set of sequence elements; and instructions for linking a first sequence element in the set of sequence elements in the first project with a corresponding second sequence element in a set of sequence elements in another project in said plurality of projects such that, when changes are made to a nucleic acid sequence associated with said first sequence element, the same changes are made to a nucleic acid sequence associated with the second sequence element.

60. The [computer program product] *non-transitory computer readable storage medium* of claim 59, the computer program mechanism further comprising:

instructions for removing the link between the first sequence element and the second sequence element.

61. The [computer program product] *non-transitory computer readable storage medium* of claim 59, the computer program mechanism further comprising:

instructions for locking the nucleic acid sequence associated with said first sequence element and the nucleic acid sequence associated with said second sequence element so that no change is allowed to either nucleic acid sequence.

62. The [computer program product] *non-transitory computer readable storage medium* of claim 1, the computer program mechanism further comprising:

instructions for altering a directional property of a sequence element in said set of sequence elements.

63. The [computer program product] *non-transitory computer readable storage medium* of claim 62, wherein the directional property is a translation direction or a transcription direction.

64. The [computer program product] *non-transitory computer readable storage medium* of claim 1, the computer program [product] *mechanism* further comprising:

instructions for generating a report, the report comprising any combination of:

(i) the design nucleic acid sequence;
(ii) a nucleic acid sequence associated with each sequence element in said set of sequence elements;
(iii) a codon translation map for the design nucleic acid sequence;
(iv) a restriction site summary for the design nucleic acid sequence;
(v) a codon usage frequency analysis for the design nucleic acid sequence;
(vi) a GC content for the design nucleic acid sequence;
(vii) a list of repeats in the design nucleic acid sequence; and
(viii) a list of each oligonucleotide associated with the set of sequence elements.

65. The [computer program product] *non-transitory computer readable storage medium* of claim 1, wherein a first sequence element in said set of sequence elements is a DNA element and a second sequence element in said set of sequence elements in a first amino acid element, wherein said instructions for displaying a set of icons further comprise instructions for displaying a first icon in said plurality of icons representing said DNA element in an icon view or a sequence view, wherein, when said first icon is displayed in the icon view, a graphical depiction of the sequence element represented by said first icon is displayed, and when said first icon is displayed in the sequence view, all six reading frames of said DNA element is displayed, and wherein a first reading frame in the six reading frames that is in frame with the first amino acid element is highlighted in a first manner.

66. The [computer program product] *non-transitory computer readable storage medium* of claim 65, wherein a third sequence element in said set of sequence elements is an amino acid element, and wherein when said first icon is displayed in the sequence view, a second frame in the six reading frames that is in frame with the second amino acid element is highlighted in a second manner.

67. The [computer program product] *non-transitory computer readable storage medium* of claim 1, the computer program [product] *mechanism* further comprising:
   instructions for communicating a sequence of the design nucleic acid sequence across a network as part of an order for said design nucleic acid sequence.

68. The [computer program product] *non-transitory computer readable storage medium* of claim 67, wherein the network in the Internet.

69. The [computer program product] *non-transitory computer readable storage medium* of claim 67, wherein the sequence is encrypted.

70. *The non-transitory computer readable storage medium of claim 1 wherein a respective directional property is displayed with each corresponding sequence element in said set of sequence elements.*

71. *The non-transitory computer readable storage medium of claim 70, wherein*
   *a first sequence element in said set of sequence elements is displayed in a 5' to 3' orientation, and*
   *a second sequence element in said set of sequence elements is displayed in a 3' to 5' orientation.*

72. *The non-transitory computer readable storage medium of claim 70, wherein*
   *a first sequence element in said set of sequence elements is displayed in first orientation, and*
   *a second sequence element in said set of sequence elements is displayed in a second orientation, other than the first orientation.*

73. *The non-transitory computer readable storage medium of claim 1, the computer program mechanism further comprising:*
   *instructions for providing an order module to receive a request to communicate a sequence of the design nucleic acid sequence across a network as part of an order for the design nucleic acid sequence; and*
   *instructions for communicating the sequence of the design nucleic acid sequence across the network as part of the order for the design nucleic acid sequence when the order module receives the request.*

74. *The non-transitory computer readable storage medium of claim 73, wherein the order for the design nucleic acid sequence is encrypted.*

* * * * *

SEQUENCE LISTING

<160> NUMBER OF SEQ ID NOS: 11

<210> SEQ ID NO 1
<211> LENGTH: 1865
<212> TYPE: DNA
<213> ORGANISM: Artificial Sequence
<220> FEATURE:
<223> OTHER INFORMATION: Oligonucleotide

<400> SEQUENCE: 1
ggatccggct ttacacttta tgcttccggc tcgtatgttg tgtggaggaa ttgtgagcgg    60

-continued

```
ataacaattc aggaggataa catatgagcc cgatcctagg ttattggaaa atcaaaggcc      120
tggttcagcc gacgcgtctg ctgctggaat acctggaaga aaaatacgaa gaacacctgt      180
acgaacgcga tgaaggtgat aaatggcgca acaaaaagtt tgaactgggt ctggaatttc      240
cgaacctgcc gtactatatt gatggtgatg taaaactgac ccaatccatg gccatcatcc      300
gttacattgc cgataaacat aacatgctgg gtggttgtcc taaagaacgt gccgaaatta      360
gcatgctgga gggtgcagtc ctggatatcc gttatggtgt cagccgcatt gcttactcca      420
aagacttcga aaccctgaag gtcgatttcc tgtccaaact gccggaaatg ctgaaaatgt      480
ttgaggaccg tctgtgccac aaaacgtacc tgaatggcga ccacgtaact catccggact      540
tcatgctgta tgacgcgctg gacgtagttc tgtacatgga cccgatgtgc ctggacgcat      600
tcccgaaact ggtgtgtttc aaaaagcgta ttgaagccat cccgcagatc gataaatacc      660
tgaaatccag caaatacatt gcatggccgc tgcagggctg gcaggcaacc ttcggcggtg      720
gcgatcatcc gccgaaaagc gacctggtcc cacgtggcag cacgccggaa cacctgccga      780
cggaacagta cgaggcgcag ctggctgaaa aagttgtacg tctgcaatct atgatggccc      840 cttttttctga cctggtaccg gaagtcttcc gttctccggt gtcccactat cgtatgcgtg      900
cagaattccg tatctggcac gacggtgacg acctgtacca cattatcttc gatcagcaga      960
cgaaatctcg tatccgcgtt gactcttttcc cagctgcgag cgaactgatc aaccagctga     1020
tgactgcaat gatcgcaggt gtacgcaaca cccagtgct gcgtcacaag ctgttccaaa     1080
ttgattatct gactactctg agcaaccagg ctgtggtatc tctgctgtac cacaagaaac     1140
tggacgacga atggcgtcag gaagcggaag cactgcgtga cgcactgcgc gcacagaacc     1200
tgaacgtgca cctgattggc cgtgctacga aaaccaaaat cgaactggat caggattata     1260
tcgacgaacg tctgccggtt gcaggcaaag aaatgatcta ccgtcaggtg gagaattctt     1320
tcacccagcc gaacgcagca atgaacatcc agatgctgga atgggcgctg gacgttacca     1380
aaggttctaa aggcgaccctg ctggaactgt actgcggcaa cggtaacttt agcctggctc     1440
tggcacgtaa cttcgaccgc gttctggcca ccgaaatcgc aaagccttcc gttgcggcag     1500
cccaatataa cattgcggca aaccacatcg ataacgtgca gatcattcgc atggcggcag     1560
aagaattcac ccaggcgatg aacggcgtgc gtgaatttaa ccgtctgcag gcatcgatc     1620 tgaaatccta ccagtgcgag actattttcg ttgatccgcc gcgttccggt ctggactccg     1680
aaaccgaaaa gatggttcag gcgtaccctc gtattctgta tatcagctgc aaccctgaaa     1740
ctctgtgcaa aaacctggaa accctgagcc aaacccataa agtcgagcgt ctggctctgt     1800
ttgatcagtt cccgtacact caccatatgg aatgtggtgt actgctgacc gcgaagtaag     1860
aattc                                                                  1865
```

<210> SEQ ID NO 2
<211> LENGTH: 40
<212> TYPE: DNA
<213> ORGANISM: Artificial Sequence
<220> FEATURE:
<223> OTHER INFORMATION: P-lac Oligonucleotide

<400> SEQUENCE: 2

```
ggctttacac tttatgcttc cggctcgtat gttgtgtgga                              40
```

<210> SEQ ID NO 3
<211> LENGTH: 37
<212> TYPE: DNA

<213> ORGANISM: Artificial Sequence
<220> FEATURE:
<223> OTHER INFORMATION: 0-lac-Shine-Dalgarno with Spacer Polynucleotide

<400> SEQUENCE: 3
ggaattgtga gcggataaca attcaggagg ataacat                              37

<210> SEQ ID NO 4
<211> LENGTH: 642
<212> TYPE: DNA
<213> ORGANISM: Artificial Sequence
<220> FEATURE:
<223> OTHER INFORMATION: GST(1) Polynucleotide

<400> SEQUENCE: 4
agcccgatcc taggttattg gaaaatcaaa ggcctggttc agccgacgcg tctgctgctg     60
gaatacctgg aagaaaaata cgaagaacac ctgtacgaac gcgatgaagg tgataaatgg    120
cgcaacaaaa agtttgaact gggtctggaa tttccgaacc tgccgtacta tattgatggt    180
gatgtaaaac tgacccaatc catggccatc atccgttaca ttgccgataa cataacatg     240 ctgggtggtt gtcctaaaga acgtgccgaa attagcatgc tggagggtgc agtcctggat    300
atccgttatg gtgtcagccg cattgcttac tccaaagact cgaaaccct gaaggtcgat     360 ttcctgtcca aactgccgga aatgctgaaa atgtttgagg accgtctgtg ccacaaaacg    420
tacctgaatg gcgaccacgt aactcatccg gacttcatgc tgtatgacgc gctggacgta    480
gttctgtaca tggacccgat gtgcctggac gcattcccga actggtgtg tttcaaaaag    540 cgtattgaag ccatcccgca gatcgataaa tacctgaaat ccagcaaata cattgcatgg    600
ccgctgcagg gctggcaggc aaccttcggc ggtggcgatc at                       642

<210> SEQ ID NO 5
<211> LENGTH: 24
<212> TYPE: DNA
<213> ORGANISM: Artificial Sequence
<220> FEATURE:
<223> OTHER INFORMATION: GST(2)-Thrombin(1) Polynucleotide

<400> SEQUENCE: 5
ccgccgaaaa gcgacctggt ccca                                            24

<210> SEQ ID NO 6
<211> LENGTH: 15
<212> TYPE: DNA
<213> ORGANISM: Artificial Sequence
<220> FEATURE:
<223> OTHER INFORMATION: TRMA(1) Polynucleotide

<400> SEQUENCE: 6
acgccggaac acctg                                                      15

<210> SEQ ID NO 7
<211> LENGTH: 1080
<212> TYPE: DNA
<213> ORGANISM: Artificial Sequence
<220> FEATURE:
<223> OTHER INFORMATION: TRMA(2) Oligonucleotide

<400> SEQUENCE: 7
ccgacggaac agtacgaggc gcagctggct gaaaaagttg tacgtctgca atctatgatg    60
gccccttttt ctgaccctgg taccggaagtc ttccgttctc cggtgtccca ctatcgtatg   120
cgtgcagaat tccgtatctg gcacgacggt gacgacctgt accacattat cttcgatcag   180

```
cagacgaaat ctcgtatccg cgttgactct ttcccagctg cgagcgaact gatcaaccag    240
ctgatgactg caatgatcgc aggtgtacgc aacaacccag tgctgcgtca caagctgttc    300
caaattgatt atctgactac tctgagcaac caggctgtgg tatctctgct gtaccacaag    360
aaactggacg acgaatggcg tcaggaagcg aaagcactgc gtgacgcact gcgcgcacag    420
aacctgaacg tgcacctgat tggccgtgct acgaaaacca aaatcgaact ggatcaggat    480
tatatcgacg aacgtctgcc ggttgcaggc aaagaaatga tctaccgtca ggtggagaat    540
tctttcaccc agccgaacgc agcaatgaac atccagatgc tggaatgggc gctggacgtt    600
accaaaggtt ctaaaggcga cctgctggaa ctgtactgcg gcaacggtaa ctttagcctg    660
gctctggcac gtaacttcga ccgcgttctg gccaccgaaa tcgcaaagcc ttccgttgcg    720
gcagcccaat ataacattgc ggcaaaccac atcgataacg tgcagatcat tcgcatggcg    780
gcagaagaat tcacccaggc gatgaacggc gtgcgtgaat taaccgtctg cagggcatc    840 gatctgaaat cctaccagtg cgagactatt ttcgttgatc cgccgcgttc cggtctggac    900
tccgaaaccg aaaagatggt tcaggcgtac cctcgtattc tgtatatcag ctgcaaccct    960
gaaactctgt gcaaaaacct ggaaaccctg agccaaaccc ataaagtcga gcgtctggct    1020
ctgtttgatc agttcccgta cactcaccat atggaatgtg tgtactgct gaccgcgaag    1080
```

```
<210> SEQ ID NO 8
<211> LENGTH: 214
<212> TYPE: PRT
<213> ORGANISM: Artificial Sequence
<220> FEATURE:
<223> OTHER INFORMATION: GST(1) Polypeptide

<400> SEQUENCE: 8

Ser Pro Ile Leu Gly Tyr Trp Lys Ile Lys Gly Leu Val Gln Pro Thr
 1               5                  10                  15

Arg Leu Leu Leu Glu Tyr Leu Glu Glu Lys Tyr Glu Glu His Leu Tyr
                20                  25                  30

Glu Arg Asp Glu Gly Asp Lys Trp Arg Asn Lys Lys Phe Glu Leu Gly
            35                  40                  45

Leu Glu Phe Pro Asn Leu Pro Tyr Tyr Ile Asp Gly Asp Val Lys Leu
        50                  55                  60

Thr Gln Ser Met Ala Ile Ile Arg Tyr Ile Ala Asp Lys His Asn Met
65                  70                  75                  80

Leu Gly Gly Cys Pro Lys Glu Arg Ala Glu Ile Ser Met Leu Glu Gly
                85                  90                  95

Ala Val Leu Asp Ile Arg Tyr Gly Val Ser Arg Ile Ala Tyr Ser Lys
            100                 105                 110

Asp Phe Glu Thr Leu Lys Val Asp Phe Leu Ser Lys Leu Pro Glu Met
        115                 120                 125

Leu Lys Met Phe Glu Asp Arg Leu Cys His Lys Thr Tyr Leu Asn Gly
    130                 135                 140

Asp His Val Thr His Pro Asp Phe Met Leu Tyr Asp Ala Leu Asp Val
145                 150                 155                 160

Val Leu Tyr Met Asp Pro Met Cys Leu Asp Ala Phe Pro Lys Leu Val
                165                 170                 175

Cys Phe Lys Lys Arg Ile Glu Ala Ile Pro Gln Ile Asp Lys Tyr Leu
            180                 185                 190

Lys Ser Ser Lys Tyr Ile Ala Trp Pro Leu Gln Gly Trp Gln Ala Thr
        195                 200                 205
```

```
Phe Gly Gly Gly Asp His
    210

<210> SEQ ID NO 9
<211> LENGTH: 8
<212> TYPE: PRT
<213> ORGANISM: Artificial Sequence
<220> FEATURE:
<223> OTHER INFORMATION: GST(2)-Thrombin(1) Peptide

<400> SEQUENCE: 9

Pro Pro Lys Ser Asp Leu Val Pro
1               5

<210> SEQ ID NO 10
<211> LENGTH: 5
<212> TYPE: PRT
<213> ORGANISM: Artificial Sequence
<220> FEATURE:
<223> OTHER INFORMATION: TRMA(1) Peptide

<400> SEQUENCE: 10

Thr Pro Glu His Leu
1               5

<210> SEQ ID NO 11
<211> LENGTH: 360
<212> TYPE: PRT
<213> ORGANISM: Artificial Sequence
<220> FEATURE:
<223> OTHER INFORMATION: TRMA (2) Polypeptide

<400> SEQUENCE: 11

Pro Thr Glu Gln Tyr Glu Ala Gln Leu Ala Glu Lys Val Val Arg Leu
1               5                   10                  15

Gln Ser Met Met Ala Pro Phe Ser Asp Leu Val Pro Glu Val Phe Arg
            20                  25                  30

Ser Pro Val Ser His Tyr Arg Met Arg Ala Glu Phe Arg Ile Trp His
        35                  40                  45

Asp Gly Asp Asp Leu Tyr His Ile Ile Phe Asp Gln Gln Thr Lys Ser
    50                  55                  60

Arg Ile Arg Val Asp Ser Phe Pro Ala Ala Ser Glu Leu Ile Asn Gln
65                  70                  75                  80

Leu Met Thr Ala Met Ile Ala Gly Val Arg Asn Asn Pro Val Leu Arg
                85                  90                  95

His Lys Leu Phe Gln Ile Asp Tyr Leu Thr Thr Leu Ser Asn Gln Ala
            100                 105                 110

Val Val Ser Leu Leu Tyr His Lys Lys Leu Asp Asp Glu Trp Arg Gln
        115                 120                 125

Glu Ala Glu Ala Leu Arg Asp Ala Leu Arg Ala Gln Asn Leu Asn Val
    130                 135                 140

His Leu Ile Gly Arg Ala Thr Lys Thr Lys Ile Glu Leu Asp Gln Asp
145                 150                 155                 160

Tyr Ile Asp Glu Arg Leu Pro Val Ala Gly Lys Glu Met Ile Tyr Arg
                165                 170                 175

Gln Val Glu Asn Ser Phe Thr Gln Pro Asn Ala Ala Met Asn Ile Gln
            180                 185                 190

Met Leu Glu Trp Ala Leu Asp Val Thr Lys Gly Ser Lys Gly Asp Leu
        195                 200                 205
```

-continued

```
Leu Glu Leu Tyr Cys Gly Asn Gly Asn Phe Ser Leu Ala Leu Ala Arg
    210                 215                 220

Asn Phe Asp Arg Val Leu Ala Thr Glu Ile Ala Lys Pro Ser Val Ala
225                 230                 235                 240

Ala Ala Gln Tyr Asn Ile Ala Ala Asn His Ile Asp Asn Val Gln Ile
            245                 250                 255

Ile Arg Met Ala Ala Glu Glu Phe Thr Gln Ala Met Asn Gly Val Arg
            260                 265                 270

Glu Phe Asn Arg Leu Gln Gly Ile Asp Leu Lys Ser Tyr Gln Cys Glu
        275                 280                 285

Thr Ile Phe Val Asp Pro Pro Arg Ser Gly Leu Asp Ser Glu Thr Glu
    290                 295                 300

Lys Met Val Gln Ala Tyr Pro Arg Ile Leu Tyr Ile Ser Cys Asn Pro
305                 310                 315                 320

Glu Thr Leu Cys Lys Asn Leu Glu Thr Leu Ser Gln Thr His Lys Val
            325                 330                 335

Glu Arg Leu Ala Leu Phe Asp Gln Phe Pro Tyr Thr His His Met Glu
            340                 345                 350

Cys Gly Val Leu Leu Thr Ala Lys
            355                 360
```